(12) United States Patent
Sakita et al.

(10) Patent No.: US 8,728,708 B2
(45) Date of Patent: May 20, 2014

(54) PHOTOSENSITIVE RESIN COMPOSITION, OXIME SULFONATE COMPOUND, METHOD FOR FORMING CURED FILM, CURED FILM, ORGANIC EL DISPLAY DEVICE, AND LIQUID CRYSTAL DISPLAY DEVICE

(71) Applicant: Fujifilm Corporation, Tokyo (JP)

(72) Inventors: Kyouhei Sakita, Haibara-gun (JP); Wataru Kikuchi, Haibara-gun (JP); Masatoshi Yumoto, Haibara-gun (JP); Masanori Hikita, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/779,419

(22) Filed: Feb. 27, 2013

(65) Prior Publication Data

US 2013/0171415 A1 Jul. 4, 2013

Related U.S. Application Data

(63) Continuation of application No. PCT/JP2011/069561, filed on Aug. 30, 2011.

(30) Foreign Application Priority Data

| Aug. 30, 2010 | (JP) | 2010-192666 |
| Aug. 30, 2010 | (JP) | 2010-192674 |
| Jan. 7, 2011 | (JP) | 2011-001869 |
| Jul. 22, 2011 | (JP) | 2011-161197 |

(51) Int. Cl.
| G03F 7/00 | (2006.01) |
| G03F 7/004 | (2006.01) |
| G03F 7/029 | (2006.01) |
| C07D 495/00 | (2006.01) |
| C07D 307/92 | (2006.01) |

(52) U.S. Cl.
USPC ........ 430/270.1; 430/280.1; 430/322; 430/325; 430/330; 549/23; 549/26; 549/458; 549/467

(58) Field of Classification Search
USPC ........ 430/270.1, 280.1, 913, 322, 330, 325; 428/141; 549/23, 26
See application file for complete search history.

(56) References Cited

U.S. PATENT DOCUMENTS

| 4,305,954 | A * | 12/1981 | Finizio | 514/393 |
| 5,849,755 | A | 12/1998 | Englert et al. | |
| 7,022,456 | B2 * | 4/2006 | Momota | 430/270.1 |
| 7,582,406 | B2 * | 9/2009 | Nakagawa et al. | 430/270.1 |
| 8,241,833 | B2 * | 8/2012 | Kanda et al. | 430/270.1 |
| 8,329,388 | B2 * | 12/2012 | Brady et al. | 435/2 |
| 2010/0112474 | A1 * | 5/2010 | Iwasaki et al. | 430/270.1 |
| 2010/0173246 | A1 * | 7/2010 | Takita | 430/280.1 |
| 2012/0045616 | A1 * | 2/2012 | Ishiji et al. | 428/156 |
| 2012/0107563 | A1 * | 5/2012 | Yonezawa et al. | 428/156 |
| 2013/0071787 | A1 * | 3/2013 | Takita | 430/280.1 |
| 2013/0308219 | A1 * | 11/2013 | Kunimoto et al. | 359/891 |

FOREIGN PATENT DOCUMENTS

| GB | 1022745 A | | 3/1966 |
| JP | 57-163384 A | | 10/1982 |
| JP | 10-139775 A | | 5/1998 |
| JP | 2008-247780 A | | 10/2008 |
| JP | 2009-98616 A | | 5/2009 |
| JP | 2010231074 A | * | 10/2010 |
| WO | WO 2012029758 A1 | * | 3/2012 |

OTHER PUBLICATIONS

Machine translation of JP 2008-247780 (no date).*
Machine translation if JP 2010-231074 (no date).*
D. Huckle, et al., "3-Amino-4-chromanone Hydrochlorides", Journal of Medicinal Chemistry, Mar. 1969, pp. 277-279, vol. 12, No. 2.
C. O'Brien, et al., "The Synthesis of 3-Aminoflavanones", Tetrahedron, 1963, pp. 373-377, vol. 19.

Akira Kasahara, "3-Aminoflavanone no Rittai Kagaku", Journal of the Chemical Society of Japan, 1959, pp. 416-419, vol. 80, No. 4.
Rezso Bognar, et al., "Flavonoids and thiaflavonoids with N-containing groups in the heteroring", Justus Liebigs Annalen der Chemie, May 1966, pp. 225-232, vol. 693.

* cited by examiner

*Primary Examiner* — Amanda C. Walke
(74) *Attorney, Agent, or Firm* — Sughrue Mion, PLLC

(57) ABSTRACT

Disclosed is a photosensitive resin composition comprising: (Component A) an oxime sulfonate compound represented by Formula (1); (Component B) a resin comprising a constituent unit having an acid-decomposable group that is decomposed by an acid to form a carboxyl group or a phenolic hydroxy group; and (Component C) a solvent

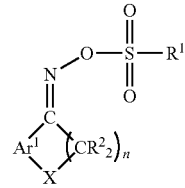

wherein in Formula (1) $R^1$ denotes an alkyl group, an aryl group, or a heteroaryl group, each $R^2$ independently denotes a hydrogen atom, an alkyl group, an aryl group, or a halogen atom, $Ar^1$ denotes an o-arylene group or an o-heteroarylene group, X denotes O or S, and n denotes 1 or 2, provided that of two or more $R^2$s present in the compound, at least one denotes an alkyl group, an aryl group, or a halogen atom.

21 Claims, 2 Drawing Sheets

PHOTOSENSITIVE RESIN COMPOSITION, OXIME SULFONATE COMPOUND, METHOD FOR FORMING CURED FILM, CURED FILM, ORGANIC EL DISPLAY DEVICE, AND LIQUID CRYSTAL DISPLAY DEVICE

TECHNICAL FIELD

The present invention relates to a photosensitive resin composition, an oxime sulfonate compound, a method for forming cured film, a cured film, an organic EL display device, and a liquid crystal display device.

BACKGROUND ART

Organic EL display devices, liquid crystal display devices, etc. are equipped with a patterned interlayer insulating film. In forming this interlayer insulating film a photosensitive resin composition is widely employed since the number of steps required for obtaining a pattern shape is small and, moreover, it gives sufficient flatness.

There is a desire for the interlayer insulating film in the display device to have high transparency in addition to cured film physical properties such as excellent insulation, solvent resistance, heat resistance, hardness, and indium tin oxide (ITO) sputtering suitability. Because of this, attempts have been made to use an acrylic resin having excellent transparency as a film-forming component.

Furthermore, with regard to a light source used for exposing a photosensitive resin composition to light, various light sources such as a mixed g-line and h-line light source with the i-line cut as well as a conventional g-line, h-line, and i-line mixed light source and a direct drawing method employing exposure to laser light at 355 nm have been used in pattern formation.

As such a photosensitive resin composition, for example, JP-A-2009-98616 (JP-A denotes a Japanese unexamined patent application publication) proposes a positive-working photosensitive resin composition that comprises at least (A) a resin that contains an acid-dissociable group-containing constituent unit represented by general Formula (1) below and a constituent unit having a functional group able to form a covalent bond by reacting with a carboxyl group, that is insoluble or sparingly soluble in alkali, and that becomes soluble in alkali when the acid-dissociable group dissociates and (B) a compound that generates an acid in response to irradiation with actinic radiation or radioactive rays.

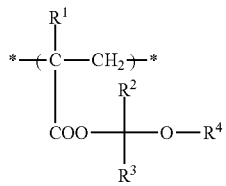

(1)

In general Formula (1), $R^1$ denotes a hydrogen atom, a methyl group, a halogen atom, or a cyano group. $R^2$ and $R^3$ independently denote a hydrogen atom, a straight-chain or branched alkyl group, or a cycloalkyl group. Here, at least one of $R^2$ and $R^3$ denotes a straight-chain or branched alkyl group or a cycloalkyl group. $R^4$ denotes a straight-chain or branched alkyl group, a cycloalkyl group, or an aralkyl group, these groups optionally having a substituent. $R^2$ or $R^3$ and $R^4$ may be bonded to form a cyclic ether.

Furthermore, as an acid generator, JP-A-2008-247780 discloses an oxime sulfonic acid compound represented by general Formula (1) below.

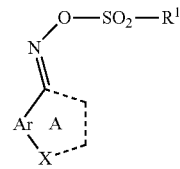

General Formula (1)

In general Formula (1) above, $R^1$ denotes any one of an alkyl group, an aryl group, and a heteroaromatic group, these groups optionally having a substituent, Ar denotes an optionally substituted aromatic ring or heteroaromatic ring, and X denotes either O or S. A denotes either a 5- or 6-membered ring.

SUMMARY OF INVENTION

It is an object of the present invention to provide a photosensitive resin composition having high sensitivity and wide development latitude and giving a cured film having excellent transparency, and a method for forming a cured film employing same. Furthermore, it is another object of the present invention to provide a photosensitive resin composition having excellent storage stability, and a method for forming a cured film employing same.

It is another object of the present invention to provide an oxime sulfonate compound having high sensitivity and wide development latitude and giving a cured film, formed by polymerization of a polymerizable compound, having excellent transparency, and having excellent storage stability even when it is mixed with another component to form a composition.

The object of the present invention has been attained by means described in <1>, <9>, <13>, <17>, <18>, <20>, or <21>. They are described below together with <2> to <8>, <10> to <12>, <14> to <16>, and <19>, which are preferred embodiments.

<1> A photosensitive resin composition comprising (Component A) an oxime sulfonate compound represented by Formula (1), (Component B) a resin comprising a constituent unit having an acid-decomposable group that is decomposed by an acid to form a carboxyl group or a phenolic hydroxy group, and (Component C) a solvent

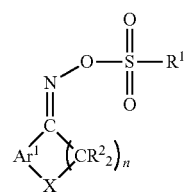

(1)

(in Formula (1), $R^1$ denotes an alkyl group, an aryl group, or a heteroaryl group, each $R^2$ independently denotes a hydrogen atom, an alkyl group, an aryl group, or a halogen atom, $Ar^1$ denotes an o-arylene group or an o-heteroarylene group, X denotes O or S, and n denotes 1 or 2, provided that of two or more $R^2$s present in the compound, at least one denotes an alkyl group, an aryl group, or a halogen atom), <2> the photosensitive resin composition according to <1> above, wherein Component B above further comprises a constituent unit derived from at least one compound selected from the group consisting of a styrene derivative, a maleimide derivative, (meth)acrylic acid, and a hydroxy group-containing (meth)acrylate compound, <3> the photosensitive resin composition according to <1> or <2> above, wherein Component B above further comprises a constituent unit having a functional group that can react with a carboxyl group or a phenolic hydroxy group to form a covalent bond, <4> the photosensitive resin composition according to any one of <1> to <3> above, wherein the acid-decomposable group is a group represented by Formula (Ia), Formula (Ib), Formula (IIa), or Formula (IIb)

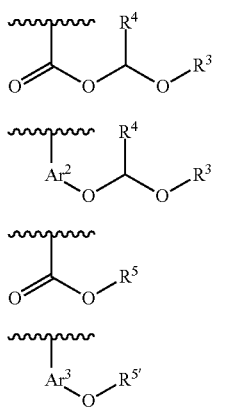

(in the Formulae, $R^3$ denotes an alkyl group or a cycloalkyl group, $R^4$ denotes an alkyl group, $R^3$ and $R^4$ may form a ring, $R^5$ denotes a tertiary alkyl group, $R^{5'}$ denotes a tertiary alkyl group or a tert-butoxycarbonyl group, $Ar^2$ and $Ar^3$ independently denote a divalent aromatic group, and a wavy line portion denotes the position of bonding to another structure), <5> the photosensitive resin composition according to any one of <1> to <4> above, wherein Component A above is an oxime sulfonate compound represented by Formula (2), Formula (3), or Formula (4)

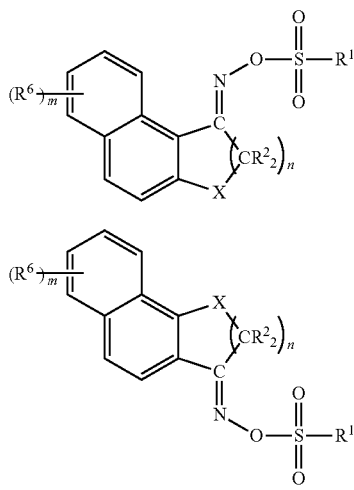

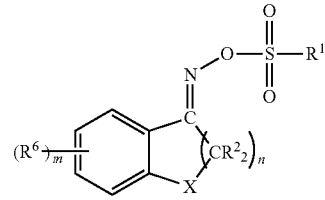

(in Formula (2) to Formula (4), $R^1$ denotes an alkyl group, an aryl group, or a heteroaryl group, each $R^2$ independently denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6, provided that of two or more $R^2$s present in the compound, at least one is an alkyl group, an aryl group, or a halogen atom), <6> the photosensitive resin composition according to any one of <1> to <5> above, wherein Component A above is an oxime sulfonate compound represented by any one of Formulae (5) to (10) below

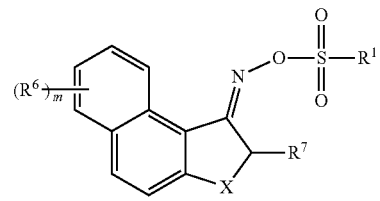

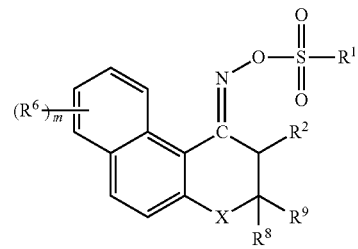

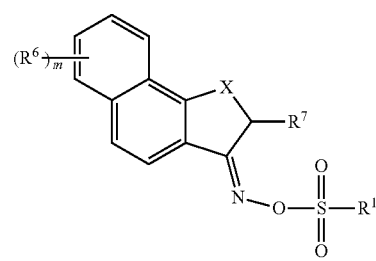

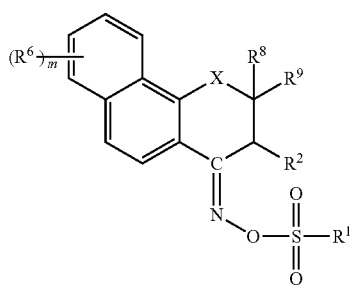

(8)

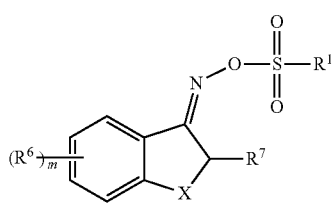

(9)

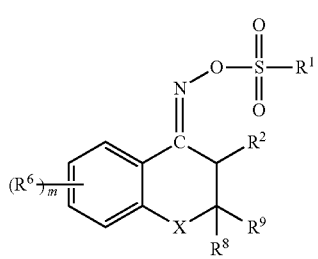

(10)

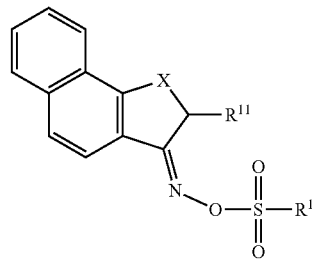

(12)

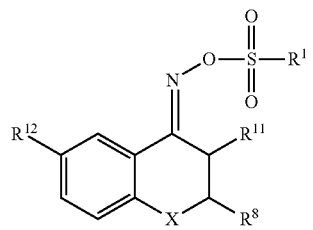

(13)

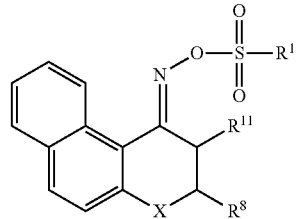

(14)

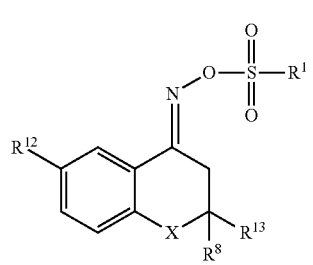

(15)

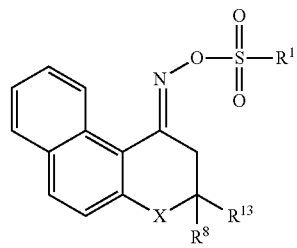

(16)

(in Formulae (5) to (10), $R^1$ denotes an alkyl group, an aryl group, or a heteroaryl group, $R^2$ denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, $R^7$ denotes an alkyl group, an aryl group, or a halogen atom, $R^8$ denotes a hydrogen atom or a methyl group, $R^9$ denotes a hydrogen atom, an alkyl group, or an aryl group, X denotes O or S, and m denotes an integer of 0 to 6, provided that in Formula (6), Formula (8), and Formula (10), not all of $R^2$, $R^8$, and $R^9$ are hydrogen atoms), <7> the photosensitive resin composition according to any one of <1> to <6> above, wherein Component A above is an oxime sulfonate compound represented by any one of Formulae (11) to (16) below

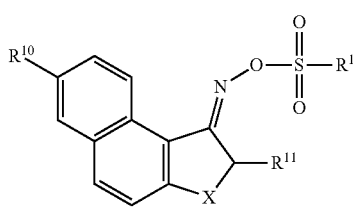

(11)

(in Formulae (11) to (16), $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, $R^{13}$ denotes an unsubstituted alkyl group having 1 to 8 carbons, a chloromethyl group, a bromomethyl group, a bromoethyl group, a methoxymethyl group, a phenyl group, or a chlorophenyl group, and X denotes O or S), <8> the photosensitive resin composition according to any one of <1> to <7> above, wherein Component A above is an oxime sulfonate compound represented by any one of Formulae (17) to (22) below

(17)
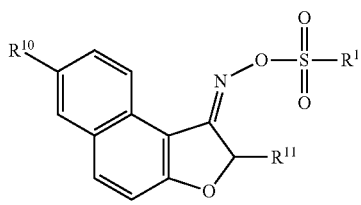

(18)
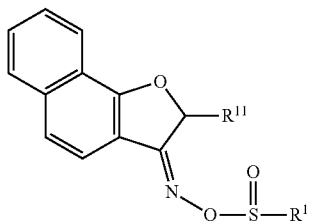

(19)
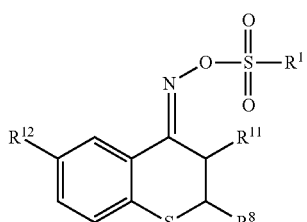

(20)
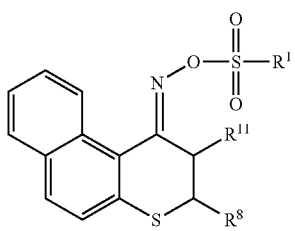

(21)
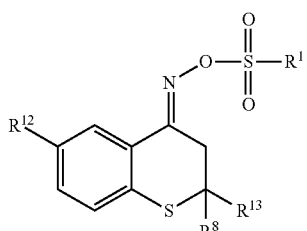

(22)
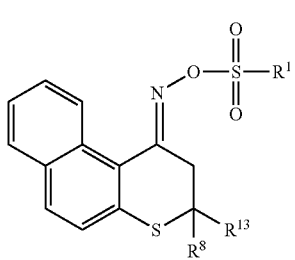

(in Formulae (17) to (22), $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, and $R^{13}$ denotes an unsubstituted alkyl group having 1 to 8 carbons, a chloromethyl group, a bromomethyl group, a bromoethyl group, a methoxymethyl group, a phenyl group, or a chlorophenyl group), <9> an oxime sulfonate compound represented by Formula (2), Formula (3), or Formula (4) below (2)
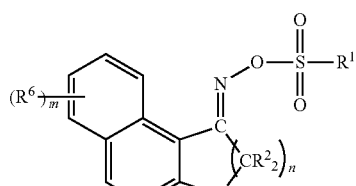

(3)
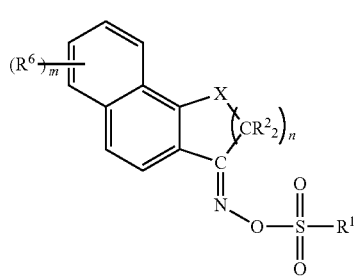

(4)
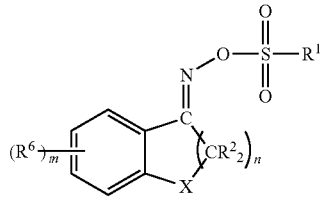

(in Formula (2) to Formula (4), $R^1$ denotes an alkyl group, an aryl group, or a heteroaryl group, each $R^2$ independently denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6, provided that of two or more $R^2$s present in the compound, at least one is an alkyl group, an aryl group, or a halogen atom), <10> the oxime sulfonate compound according to <9> above, wherein it is represented by any one of Formulae (5) to (10) below (5)
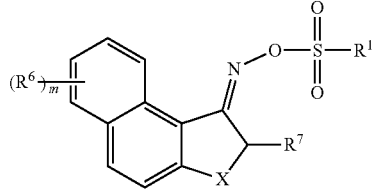

-continued (6)
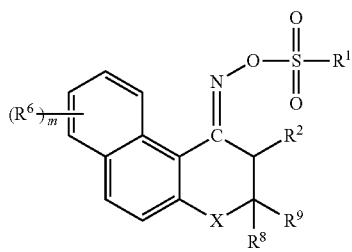

(7)
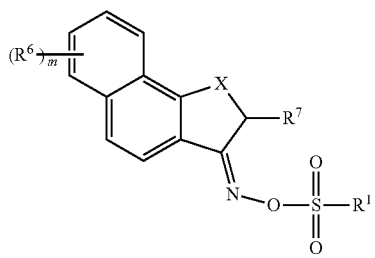

(8)
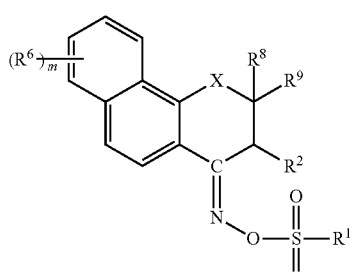

(9)
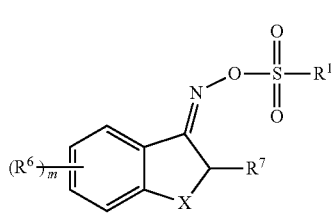

(10)
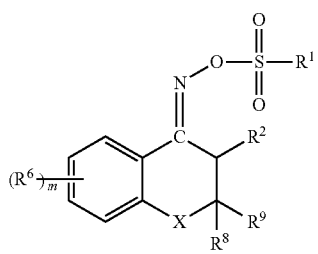

(in Formulae (5) to (10), $R^1$ denotes an alkyl group, an aryl group, or a heteroaryl group, $R^2$ denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, $R^7$ denotes an alkyl group, an aryl group, or a halogen atom, $R^8$ denotes a hydrogen atom or a methyl group, $R^9$ denotes a hydrogen atom, an alkyl group, or an aryl group, X denotes O or S, and m denotes an integer of 0 to 6, provided that in Formula (6), Formula (8), and Formula (10) not all of $R^2$, $R^8$, and $R^9$ are hydrogen atoms), <11> the oxime sulfonate compound according to <10> above, wherein it is represented by any one of Formulae (11) to (16) below

(11)
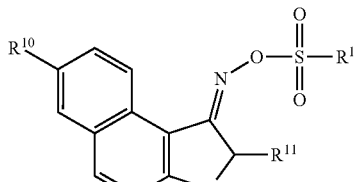

(12)
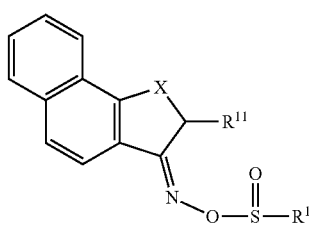

(13)
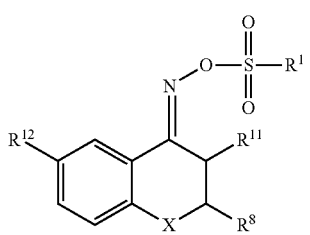

(14)
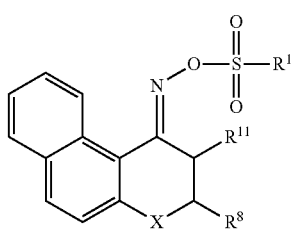

(15)
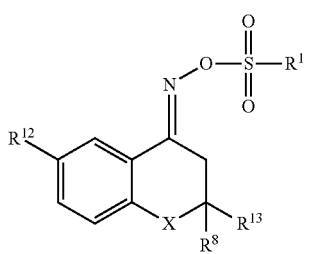

(16)
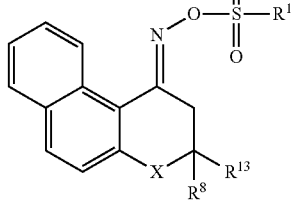

(in Formulae (11) to (16), $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, $R^{13}$ denotes an unsubstituted alkyl group having 1 to 8 carbons, a chloromethyl group, a bromomethyl group, a bromoethyl group, a methoxymethyl group, a phenyl group, or a chlorophenyl group, and X denotes O or S), <12> the oxime sulfonate compound according to <11> above, wherein it is represented by any one of Formulae (17) to (22) below

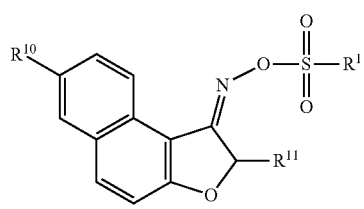
(17)

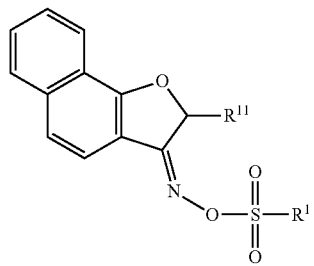
(18)

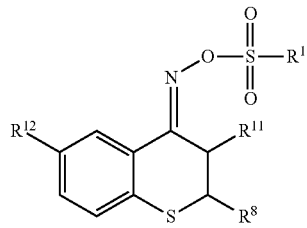
(19)

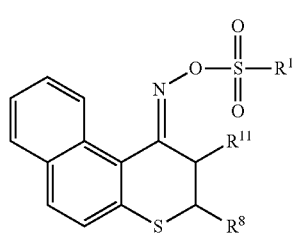
(20)

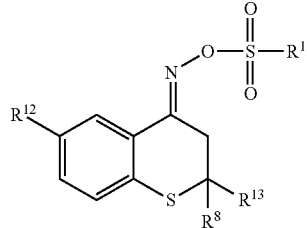
(21)

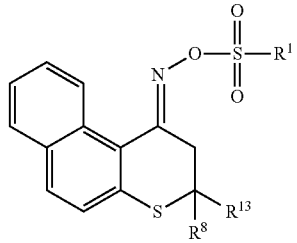
(22)

(in Formulae (17) to (22), $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, and $R^{13}$ denotes an unsubstituted alkyl group having 1 to 8 carbons, a chloromethyl group, a bromomethyl group, a bromoethyl group, a methoxymethyl group, a phenyl group, or a chlorophenyl group), <13> a photosensitive resin composition comprising (Component A') an oxime sulfonate compound represented by Formula (1'), (Component B') a (meth)acrylic copolymer comprising a constituent unit having an acid-decomposable group that is decomposed by an acid to form a carboxyl group, and (Component C) a solvent

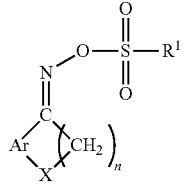
(1')

(in Formula (1'), $R^1$ denotes an alkyl group, an aryl group, or a heteroaryl group, Ar denotes an o-arylene group or an o-heteroarylene group, X denotes O or S, and n denotes 1 or 2), <14> the photosensitive resin composition according to <13>, wherein Component B' above is a (meth)acrylic copolymer comprising a constituent unit having a carboxyl group that is protected by an acetal group, <15> the photosensitive resin composition according to <13> or <14>, wherein Component A' above is an oxime sulfonate compound represented by Formula (2'), Formula (3'), or Formula (4')

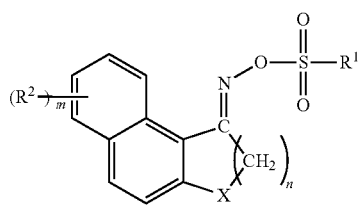
(2')

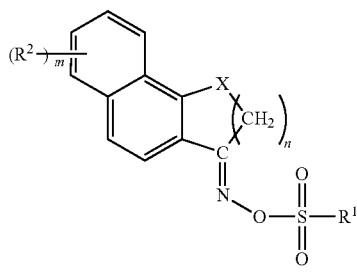

(3')

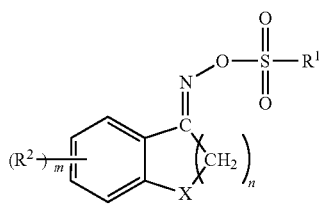

(4')

(in Formula (2') to Formula (4'), $R^1$ denotes an alkyl group, an aryl group, or a heteroaryl group, each $R^2$ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6), <16> the photosensitive resin composition according to any one of <13> to <15>, wherein Component B' above further comprises a constituent unit having a functional group that can react with a carboxyl group to form a covalent bond, <17> a method for forming a cured film, the method comprising (1) an application step of applying the photosensitive resin composition according to any one of <1> to <8> and <13> to <16> onto a substrate, (2) a solvent removal step of removing the solvent from the photosensitive resin composition that has been applied, (3) an exposure step of exposing to actinic radiation the photosensitive resin composition that has been applied, (4) a development step of developing the exposed photosensitive resin composition by means of an aqueous developer, and (5) a post-baking step of thermally curing the developed photosensitive resin composition, <18> a cured film formed by applying at least one of light and heat to the photosensitive resin composition according to any one of <1> to <8> and <13> to <16>, <19> the cured film according to <18>, wherein it is an interlayer insulating film, <20> an organic EL display device comprising the cured film according to <18> or <19>, and <21> a liquid crystal display device comprising the cured film according to <18> or <19>.

DESCRIPTION OF EMBODIMENTS (Photosensitive Resin Composition)

Figure 1:
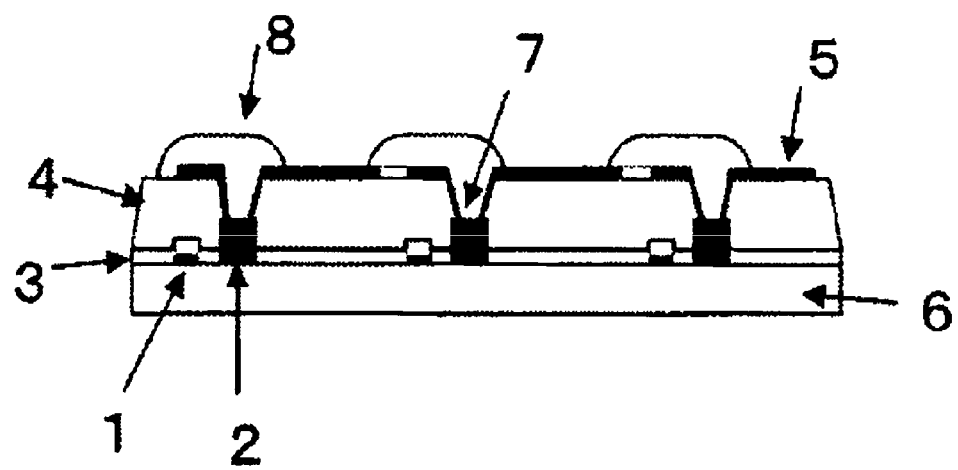
FIG. 1 is a schematic diagram of the constitution of one example of an organic EL display device, showing a schematic sectional view of a substrate in a bottom emission type organic EL display device, the substrate having a planarization film 4.

The photosensitive resin composition of the present invention is explained in detail below.

A first photosensitive resin composition of the present invention (hereinafter, also called simply a 'resin composition') comprises (Component A) an oxime sulfonate compound represented by Formula (1), (Component B) a resin comprising a constituent unit having an acid-decomposable group that is decomposed by an acid to form a carboxyl group or a phenolic hydroxy group, and (Component C) a solvent.

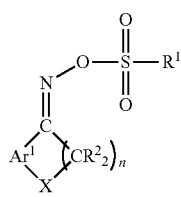

(1)

(In Formula (1), $R^1$ denotes an alkyl group, an aryl group, or a heteroaryl group, each $R^2$ independently denotes a hydrogen atom, an alkyl group, an aryl group, or a halogen atom, $Ar^1$ denotes an o-arylene group or an o-heteroarylene group, X denotes O or S, and n denotes 1 or 2. Here, of two or more $R^2$s present in the compound, at least one denotes an alkyl group, an aryl group, or a halogen atom.)

A second photosensitive resin composition (hereinafter, also called simply a 'resin composition') of the present invention comprises (Component A') an oxime sulfonate compound represented by Formula (1'), (Component B') a (meth)acrylic copolymer comprising a constituent unit having a carboxyl group that is protected by an acid-decomposable group, and (Component C) a solvent.

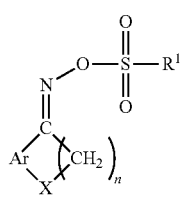

(1')

(In Formula (1'), $R^1$ denotes an alkyl group, an aryl group, or a heteroaryl group, Ar denotes an o-arylene group or an o-heteroarylene group, X denotes O or S, and n denotes 1 or 2.)

The first photosensitive resin composition and the second photosensitive resin composition of the present invention (hereinafter, the first photosensitive resin composition and the second photosensitive composition of the present invention are also called collectively 'the photosensitive resin composition of the present invention') are preferably positive-working photosensitive resin compositions.

Furthermore, the photosensitive resin composition of the present invention is preferably a chemically amplified type positive-working photosensitive resin composition (chemically amplified positive-working photosensitive resin composition).

The photosensitive resin composition of the present invention preferably does not contain a 1,2-quinone diazide compound as an actinic radiation-sensitive photo-acid generator. A 1,2-quinone diazide compound forms a carboxyl group by a sequential photochemical reaction, and the quantum yield is never greater than 1.

On the other hand, with regard to (Component A) the oxime sulfonate compound represented by Formula (1) or the oxime sulfonate compound represented by Formula (1') used in the present invention, since the acid formed in response to actinic radiation functions as a catalyst in deprotection of a protected acidic group, the acid formed by the action of one photon contributes to a large number of deprotection reactions, the quantum yield exceeds 1 and is, for example, a large number such as several orders of magnitude, and high sensitivity is obtained as a result of the so-called chemical amplification.

The 'actinic radiation' referred to here includes light that can provide energy that generates an acid in a photosensitive resin composition when exposed thereto, and examples thereof include α-rays, γ-rays, X-rays, UV, visible light, and an electronic beam. Among them, UV is preferable.

Hereinafter, the components denoted by (Component A), etc. are also expressed as 'Component A', etc.

(Component A) Oxime Sulfonate Compound Represented by Formula (1)

The first photosensitive resin composition of the present invention comprises (Component A) an oxime sulfonate compound represented by Formula (1).

The oxime sulfonate compound represented by Formula (1) (Component A) is a photo-acid generator, which generates an acid in response to actinic radiation.

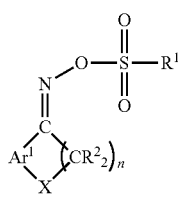

(1)

(In Formula (1), $R^1$ denotes an alkyl group, an aryl group, or a heteroaryl group, each $R^2$ independently denotes a hydrogen atom, an alkyl group, an aryl group, or a halogen atom, $Ar^1$ denotes an o-arylene group or an o-heteroarylene group, X denotes O or S, and n denotes 1 or 2. Here, of two or more $R^2$s present in the compound, at least one denotes an alkyl group, an aryl group, or a halogen atom.)

Furthermore, Component A is preferably an oxime sulfonate compound represented by Formula (2), Formula (3), or Formula (4).

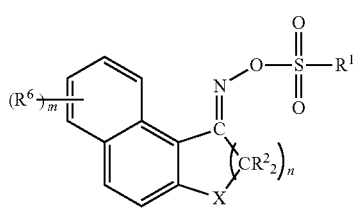

(2)

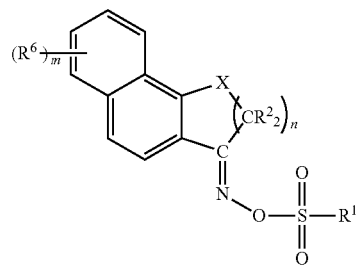

(3)

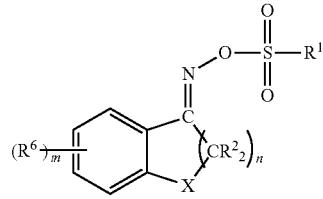

(4)

(In Formula (2) to Formula (4), $R^1$ denotes an alkyl group, an aryl group, or a heteroaryl group, each $R^2$ independently denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6. Here, of two or more $R^2$s present in the compound, at least one denotes an alkyl group, an aryl group, or a halogen atom.)

The alkyl group, aryl group, and heteroaryl group denoted by $R^1$ in the Formulae (1) to (4) optionally have a substituent.

The alkyl group denoted by $R^1$ in Formulae (1) to (4) is preferably an optionally substituted alkyl group having 1 to 30 carbons in total.

Examples of the substituent that the alkyl group denoted by $R^1$ may have include a halogen atom, an alkyloxy group, an aryloxy group, an alkylthio group, an arylthio group, an alkyloxycarbonyl group, an aryloxycarbonyl group, and an aminocarbonyl group.

Examples of the alkyl group denoted by $R^1$ include a methyl group, an ethyl group, an n-propyl group, an i-propyl group, an n-butyl group, an s-butyl group, a t-butyl group, an n-pentyl group, an n-hexyl group, an n-octyl group, an n-decyl group, an n-dodecyl group, a trifluoromethyl group, a perfluoropropyl group, a perfluorohexyl group, a benzyl group, a phenoxyethyl group, a methylthioethyl group, a phenylthioethyl group, an ethoxycarbonylethyl group, a phenoxycarbonylethyl group, and a dimethylaminocarbonylethyl group.

Among them, a methyl group, an ethyl group, an n-propyl group, an i-propyl group, an n-butyl group, an s-butyl group, a t-butyl group, an n-pentyl group, an n-hexyl group, an n-octyl group, an n-decyl group, an n-dodecyl group, a trifluoromethyl group, a perfluoropropyl group, a perfluorohexyl group, and a benzyl group are preferable.

Furthermore, in Formulae (1) to (4) above, the aryl group denoted by $R^1$ is preferably an optionally substituted aryl group having 6 to 30 carbons in total.

Examples of the substituent that the aryl group denoted by $R^1$ may have include a halogen atom, an alkyl group, an alkyloxy group, an aryloxy group, an alkylthio group, an arylthio group, an alkyloxycarbonyl group, an aryloxycarbonyl group, an aminocarbonyl group, a sulfonic acid group, an aminosulfonyl group, and an alkoxysulfonyl group.

Examples of the aryl group denoted by $R^1$ include a phenyl group, a p-methylphenyl group, a p-chlorophenyl group, a pentachlorophenyl group, a pentafluorophenyl group, an o-methoxyphenyl group, a p-phenoxyphenyl group, a p-methylthiophenyl group, a p-phenylthiophenyl group, a p-ethoxycarbonylphenyl group, a p-phenoxycarbonylphenyl group, a p-dimethylaminocarbonylphenyl group, an o-methylphenyl group, an o-nitrophenyl group, a p-nitrophenyl group, a 2,4,6-trimethylphenyl group, a 2,4,6-triisopropylphenyl group, and a 2,4-di(trifluoromethyl)phenyl group.

Among them, a phenyl group, a p-methylphenyl group, a p-chlorophenyl group, a pentachlorophenyl group, a pentafluorophenyl group, an o-methoxyphenyl group, and a p-phenoxyphenyl group are preferable.

Furthermore, in Formulae (1) to (4) above, the heteroaryl group denoted by $R^1$ is preferably an optionally substituted heteroaryl group having 4 to 30 carbons in total.

Examples of the substituent that the heteroaryl group denoted by $R^1$ may have include a halogen atom, an alkyl group, an alkyloxy group, an aryloxy group, an alkylthio group, an arylthio group, an alkyloxycarbonyl group, an aryloxycarbonyl group, an aminocarbonyl group, a sulfonic acid group, an aminosulfonyl group, and an alkoxysulfonyl group.

In Formulae (1) to (4) above, with regard to the heteroaryl group denoted by $R^1$, at least one ring may be a heteroaromatic ring, and for example a heteroaromatic ring and a benzene ring may form a fused ring.

Examples of the heteroaryl group denoted by $R^1$ include a group formed by removing one hydrogen atom from a ring selected from the group consisting of a thiophene ring, a pyrrole ring, a thiazole ring, an imidazole ring, a furan ring, a benzothiophene ring, a benzothiazole ring, and a benzimidazole ring, these rings optionally having a substituent.

In Formulae (1) to (4) above, $R^2$ is preferably a hydrogen atom, an alkyl group, or an aryl group, and more preferably a hydrogen atom or an alkyl group.

In Formulae (1) to (4) above, of two or more $R^2$s present in the compound, it is preferable that one or two are an alkyl group, an aryl group, or a halogen atom, it is more preferable that one is an alkyl group, an aryl group, or a halogen atom, and it is particularly preferable that one is an alkyl group and the rest are hydrogen atoms.

In Formulae (1) to (4) above, the alkyl group or aryl group denoted by $R^2$ optionally has a substituent.

Examples of the substituent that the alkyl group or aryl group denoted by $R^2$ may have include the same groups cited as examples for the substituent that the alkyl group or aryl group denoted by $R^1$ may have.

The alkyl group denoted by $R^2$ is preferably an optionally substituted alkyl group having 1 to 12 carbons in total, and more preferably an optionally substituted alkyl group having 1 to 6 carbons in total.

Specific examples of the alkyl group denoted by $R^2$ include a methyl group, an ethyl group, an n-propyl group, an i-propyl group, an n-butyl group, an i-butyl group, an s-butyl group, a t-butyl group, an allyl group, an n-pentyl group, an n-hexyl group, an n-octyl group, an n-decyl group, an n-dodecyl group, a perfluorohexyl group, a chloromethyl group, a bromomethyl group, a methoxymethyl group, a benzyl group, a phenoxyethyl group, a methylthioethyl group, a phenylthioethyl group, an ethoxycarbonylethyl group, a phenoxycarbonylethyl group, and a dimethylaminocarbonylethyl group.

Among them, a methyl group, an ethyl group, an n-propyl group, an i-propyl group, an n-butyl group, an i-butyl group, an s-butyl group, an n-hexyl group, an allyl group, a chloromethyl group, a bromomethyl group, a methoxymethyl group, and a benzyl group are preferable, a methyl group, an ethyl group, an n-propyl group, an i-propyl group, an n-butyl group, an i-butyl group, an s-butyl group, and an n-hexyl group are more preferable, a methyl group, an ethyl group, an n-propyl group, an n-butyl group, and an n-hexyl group are yet more preferable, and a methyl group is particularly preferable.

The aryl group denoted by $R^2$ is preferably an optionally substituted aryl group having 6 to 30 carbons in total.

Specific examples of the aryl group denoted by $R^2$ include a phenyl group, a p-methylphenyl group, an o-chlorophenyl group, a p-chlorophenyl group, an o-methoxyphenyl group, a p-phenoxyphenyl group, a p-methylthiophenyl group, a p-phenylthiophenyl group, a p-ethoxycarbonylphenyl group, a p-phenoxycarbonylphenyl group, and a p-dimethylaminocarbonylphenyl group.

Among them, a phenyl group, a p-methylphenyl group, an o-chlorophenyl group, a p-chlorophenyl group, an o-methoxyphenyl group, and a p-phenoxyphenyl group are preferable.

Examples of the halogen atom denoted by $R^2$ include a fluorine atom, a chlorine atom, a bromine atom, and an iodine atom.

Among them, a chlorine atom and a bromine atom are preferable.

In Formula (1) above, $Ar^1$ denotes an o-arylene group or an o-heteroarylene group. The o-arylene group and o-heteroarylene group denoted by $Ar^1$ optionally have a substituent.

Examples of the substituent include a halogen atom, an alkyl group, and an alkyloxy group, and they optionally further have a substituent. Preferred examples of the substituent that the o-arylene group and the o-heteroarylene group may have include $R^2$, which is described later.

Specific examples of the o-arylene group and o-heteroarylene group denoted by $Ar^1$ include a 1,2-phenylene group, a 1,2-naphthalenediyl group, a 2,3-naphthalenediyl group, a 2,3-furandiyl group, a 2,3-thiophenediyl group, a 2,3-quinolinediyl group, a 6,7-quinolinediyl group, and a 7,8-quinolinediyl group, these groups optionally having a substituent.

Among them, $Ar^1$ is preferably an o-arylene group, more preferably a 1,2-phenylene group or a 1,2-naphthalenediyl group, and particularly preferably a 1,2-naphthalenediyl group.

In Formulae (1) to (4) above, X denotes O or S.

In Formula (1), X, $Ar^1$, the carbon atom of the oxime group, and —$(CR_2)_n$— are bonded to form a 5-membered ring or a 6-membered ring.

Similarly, in Formulae (2) to (4), the ring containing X as a ring member is a 5-membered ring or a 6-membered ring.

In Formulae (1) to (4) above, n denotes 1 or 2, and when X is O, n is preferably 1, and when X is S, n is preferably 2.

In Formulae (2) to (4) above, the alkyl group and alkyloxy group denoted by $R^6$ optionally have a substituent.

In Formulae (2) to (4) above, the alkyl group denoted by $R^6$ is preferably an optionally substituted alkyl group having 1 to 30 carbons in total.

Examples of the substituent that the alkyl group denoted by $R^6$ may have include a halogen atom, an alkyloxy group, an aryloxy group, an alkylthio group, an arylthio group, an alkyloxycarbonyl group, an aryloxycarbonyl group, and an aminocarbonyl group.

Examples of the alkyl group denoted by $R^6$ include a methyl group, an ethyl group, an n-propyl group, an i-propyl group, an n-butyl group, an s-butyl group, a t-butyl group, an n-pentyl group, an n-hexyl group, an n-octyl group, an n-decyl group, an n-dodecyl group, a trifluoromethyl group, a perfluoropropyl group, a perfluorohexyl group, a benzyl group, a phenoxyethyl group, a methylthioethyl group, a phenylthioethyl group, an ethoxycarbonylethyl group, a phenoxycarbonylethyl group, and a dimethylaminocarbonylethyl group.

Among them, a methyl group, an ethyl group, an n-propyl group, an i-propyl group, an n-butyl group, an s-butyl group, a t-butyl group, an n-pentyl group, an n-hexyl group, an n-octyl group, an n-decyl group, an n-dodecyl group, a trifluoromethyl group, a perfluoropropyl group, a perfluorohexyl group, and a benzyl group are preferable.

In Formulae (2) to (4) above, the alkyloxy group denoted by $R^6$ is preferably an optionally substituted alkyloxy group having 1 to 30 carbons in total.

Examples of the substituent that the alkyloxy group denoted by $R^6$ may have include a halogen atom, an alkyloxy group, an aryloxy group, an alkylthio group, an arylthio group, an alkyloxycarbonyl group, an aryloxycarbonyl group, and an aminocarbonyl group.

Examples of the alkyloxy group denoted by $R^6$ include a methyloxy group, an ethyloxy group, a butyloxy group, a hexyloxy group, a phenoxyethyloxy group, a trichloromethyloxy group, an ethoxyethyloxy group, a methylthioethyloxy group, a phenylthioethyloxy group, an ethoxycarbonylethyloxy group, a phenoxycarbonylethyloxy group, and a dimethylaminocarbonylethyloxy group.

Among them, a methyloxy group, an ethyloxy group, a butyloxy group, a hexyloxy group, a phenoxyethyloxy group, a trichloromethyloxy group, and an ethoxyethyloxy group are preferable.

In Formulae (2) to (4) above, examples of the aminosulfonyl group denoted by $R^6$ include a methylaminosulfonyl group, a dimethylaminosulfonyl group, a phenylaminosulfonyl group, a methylphenylaminosulfonyl group, and an aminosulfonyl group.

In Formulae (2) to (4) above, examples of the alkoxysulfonyl group denoted by $R^6$ include a methoxysulfonyl group, an ethoxysulfonyl group, a propyloxysulfonyl group, and a butyloxysulfonyl group.

Furthermore, in Formulae (2) to (4) above, m denotes an integer of 0 to 6, preferably an integer of 0 to 2, more preferably 0 or 1, and particularly preferably 0.

Moreover, it is more preferable that Component A above is an oxime sulfonate compound represented by any one of Formulae (5) to (10) below.

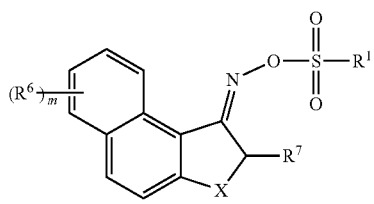

(5)

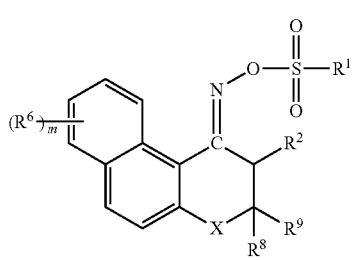

(6)

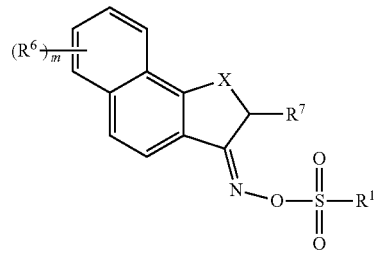

(7)

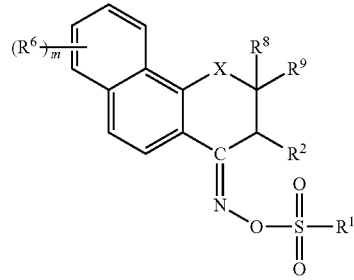

(8)

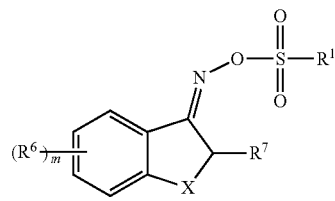

(9)

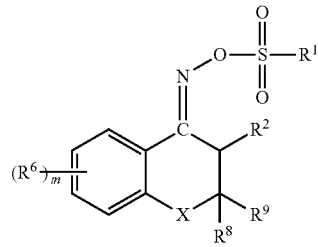

(10)

(In Formulae (5) to (10), $R^1$ denotes an alkyl group, an aryl group, or a heteroaryl group, $R^2$ denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, $R^7$ denotes an alkyl group, an aryl group, or a halogen atom, $R^8$ denotes a hydrogen atom or a methyl group, $R^9$ denotes a hydrogen atom, an alkyl group, or an aryl group, X denotes O or S, and m denotes an integer of 0 to 6. Here, in Formula (6), Formula (8), and Formula (10), not all of $R^2$, $R^8$, and $R^9$ are hydrogen atoms.)

$R^1$, $R^2$, $R^6$, X, and m in Formulae (5) to (10) have the same meanings as $R^1$, $R^2$, $R^6$, X, and m in Formulae (1) to (4) above, and preferred embodiments are also the same.

$R^7$ in Formulae (5), (7) and (9) denotes an alkyl group, an aryl group, or a halogen atom and is preferably an alkyl group or an aryl group, and more preferably an alkyl group.

$R^8$ in Formulae (6), (8) and (10) denotes a hydrogen atom or a methyl group and is more preferably a hydrogen atom.

$R^9$ in Formulae (6), (8) and (10) denotes a hydrogen atom, an alkyl group, or an aryl group and is preferably a hydrogen atom or an alkyl group.

In Formula (6), Formula (8), and Formula (10), not all of $R^2$, $R^8$, and $R^9$ are hydrogen atoms, and it is particularly preferable that two of $R^2$, $R^8$, and $R^9$ are hydrogen atoms.

Furthermore, Component A above is yet more preferably an oxime sulfonate compound represented by any one of Formulae (11) to (16) below.

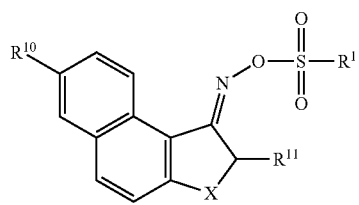 (11)

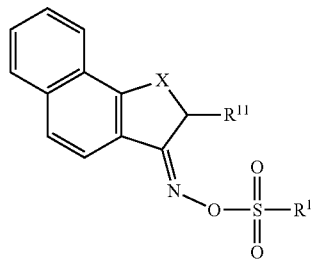 (12)

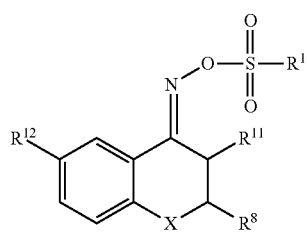 (13)

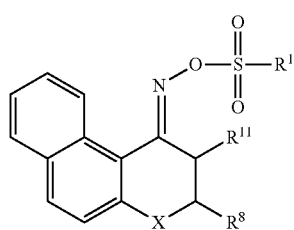 (14)

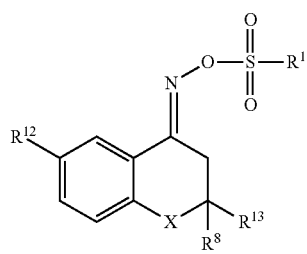 (15)

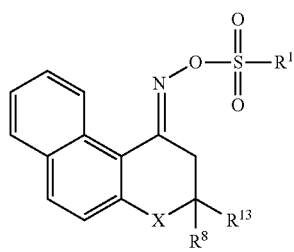 (16)

(In Formulae (11) to (16), $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, $R^{13}$ denotes an unsubstituted alkyl group having 1 to 8 carbons, a chloromethyl group, a bromomethyl group, a bromoethyl group, a methoxymethyl group, a phenyl group, or a chlorophenyl group, and X denotes O or S.)

$R^1$ and X in Formulae (11) to (16) have the same meanings as $R^1$ and X in Formulae (1) to (4) above, and preferred embodiments are also the same.

$R^8$ in Formulae (13) to (16) has the same meaning as $R^8$ in Formulae (6), (8) and (10) above, and preferred embodiments are also the same.

$R^{10}$ in Formula (11) denotes a hydrogen atom or a bromine atom and is preferably a hydrogen atom.

$R^{11}$ in Formulae (11) to (14) denotes an unsubstituted alkyl group having 1 to 8 carbons, a halogen atom, a chloromethyl group, a bromomethyl group, a bromoethyl group, a methoxymethyl group, a phenyl group, or a chlorophenyl group and is preferably an unsubstituted alkyl group having 1 to 8 carbons, a halogen atom, or a phenyl group, more preferably an unsubstituted alkyl group having 1 to 8 carbons, yet more preferably an unsubstituted alkyl group having 1 to 6 carbons, and particularly preferably a methyl group.

$R^{12}$ in Formula (13) and Formula (15) denotes a hydrogen atom, a halogen atom, a methyl group, or a methoxy group, and is preferably a hydrogen atom.

$R^{13}$ in Formula (15) and Formula (16) denotes an unsubstituted alkyl group having 1 to 8 carbons, a chloromethyl group, a bromomethyl group, a bromoethyl group, a methoxymethyl group, a phenyl group, or a chlorophenyl group and is preferably an unsubstituted alkyl group having 1 to 8 carbons, a halogen atom, or a phenyl group, more preferably an unsubstituted alkyl group having 1 to 8 carbons, yet more preferably an unsubstituted alkyl group having 1 to 6 carbons, and particularly preferably a methyl group.

Furthermore, Component A above is particularly preferably an oxime sulfonate compound represented by any one of Formulae (17) to (22) below.

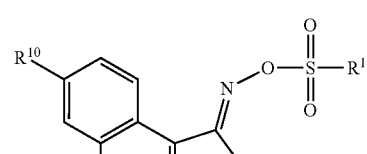 (17)

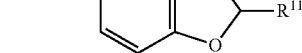 (18)

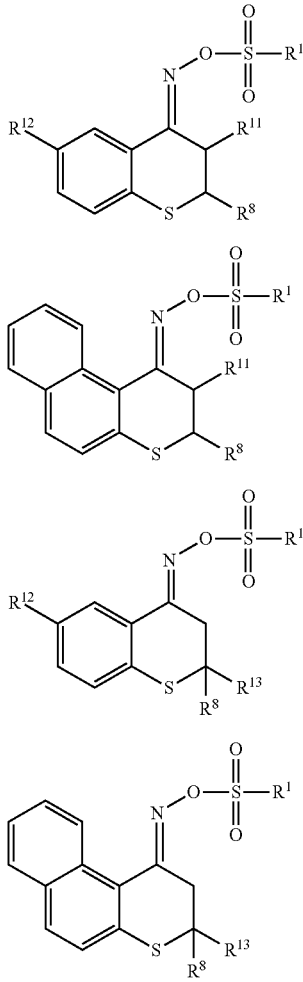

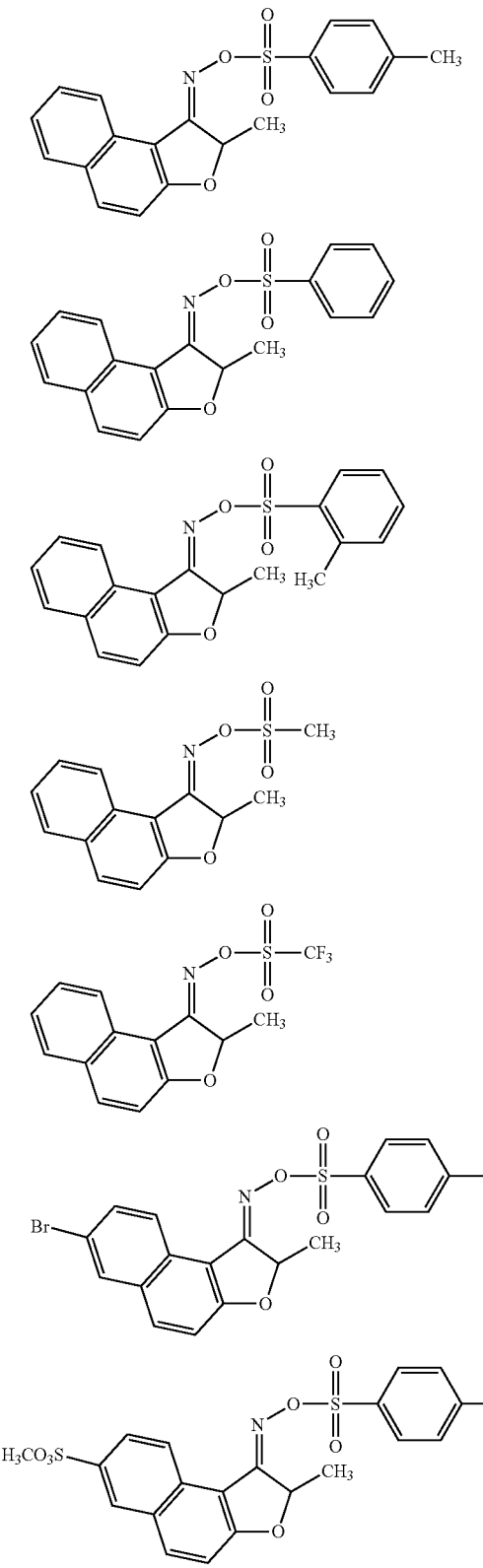

(In Formulae (17) to (22), $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, and $R^{13}$ denotes an unsubstituted alkyl group having 1 to 8 carbons, a chloromethyl group, a bromomethyl group, a bromoethyl group, a methoxymethyl group, a phenyl group, or a chlorophenyl group.)

$R^{10}$ in Formula (17) has the same meaning as $R^{10}$ in Formula (11) above, and preferred embodiments are also the same.

$R^{11}$ in Formulae (17) to (20) has the same meaning as $R^{11}$ in Formulae (11) to (14) above, and preferred embodiments are also the same.

$R^{12}$ in Formula (19) and Formula (21) has the same meaning as $R^{12}$ in Formula (13) and Formula (15) above, and preferred embodiments are also the same.

$R^{13}$ in Formula (21) and Formula (22) has the same meaning as $R^{13}$ in Formula (15) and Formula (16) above, and preferred embodiments are also the same.

Furthermore, with regard to the oxime sulfonate compound, the oxime may have either conformation (E, Z), or it may be a mixture thereof.

Specific examples of the oxime sulfonate compound represented by Formula (1) above include the compound examples illustrated below, but the present invention is not limited thereby.

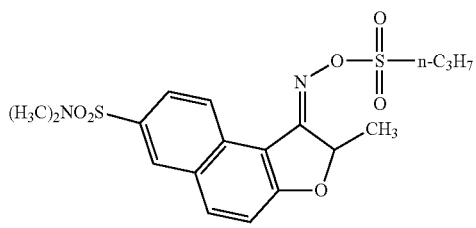
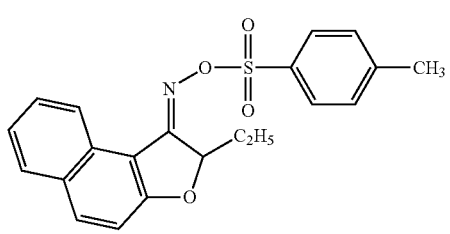
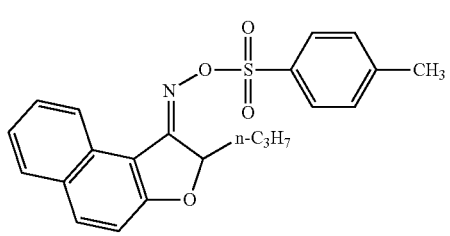
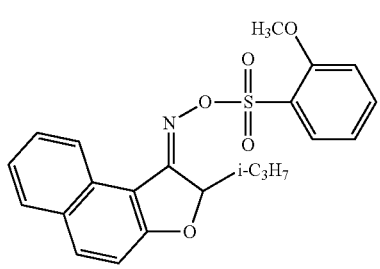
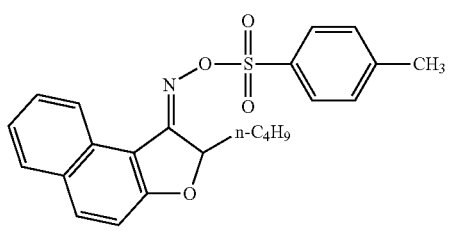
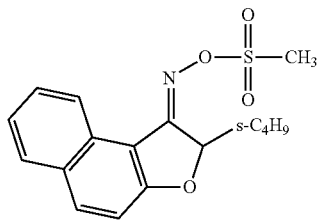
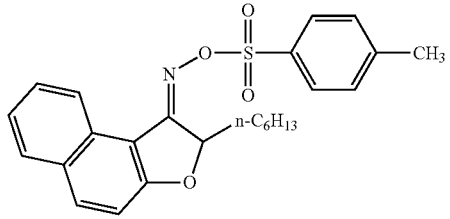
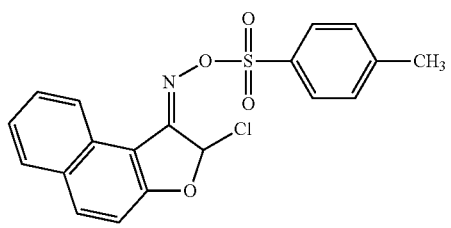
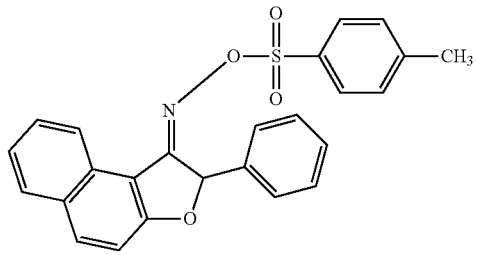
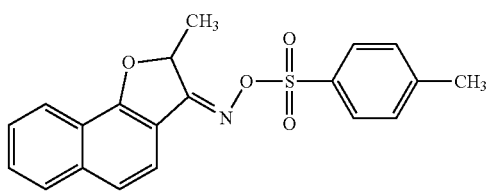
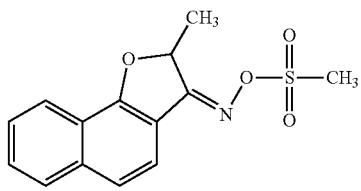
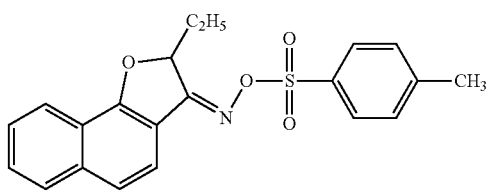
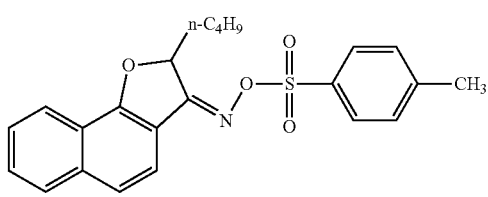
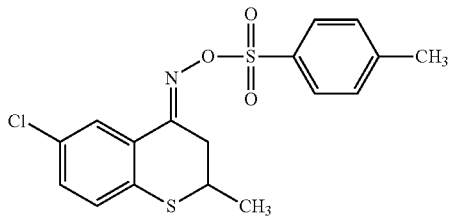
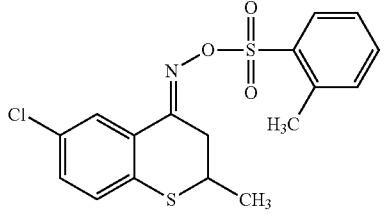

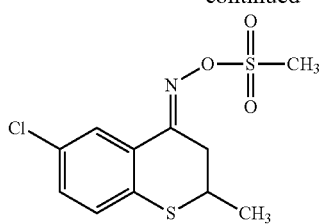
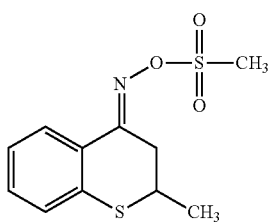
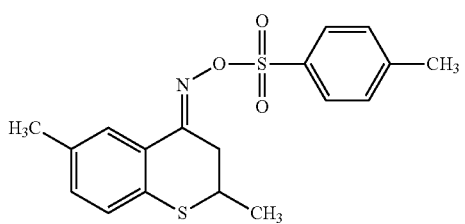
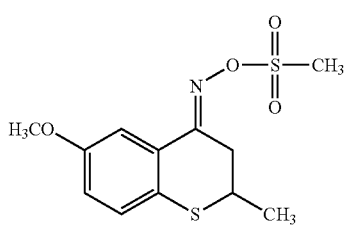
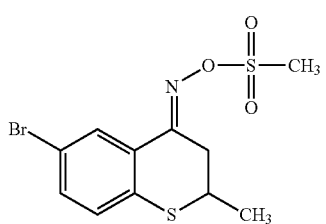
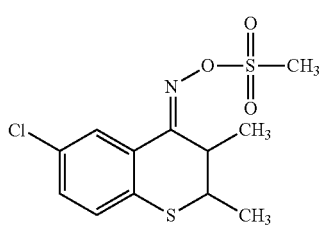
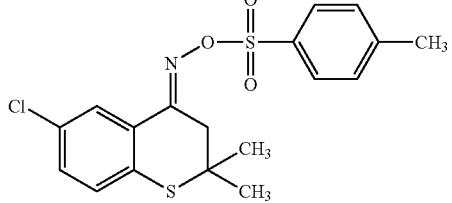
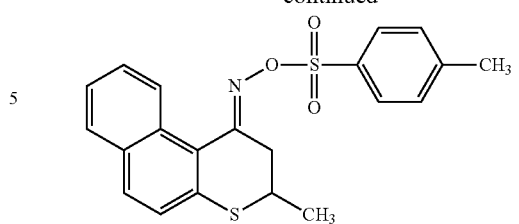
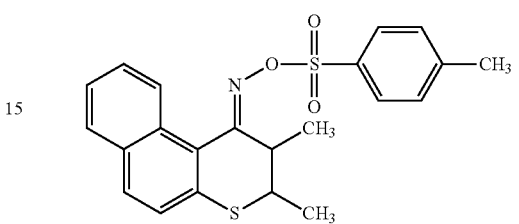
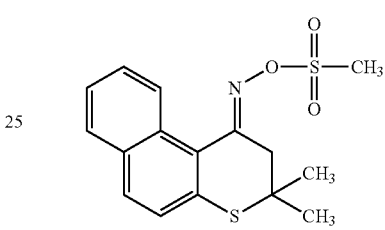
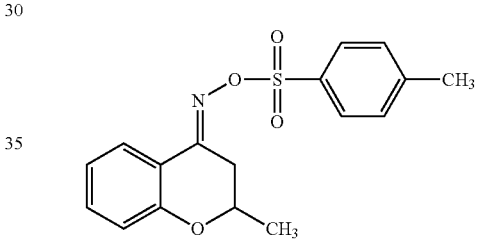
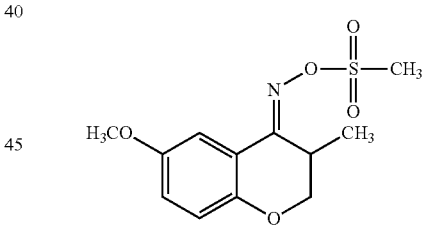
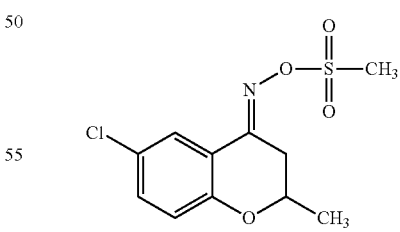
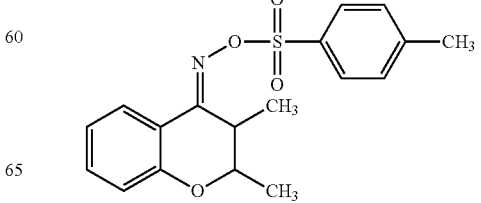

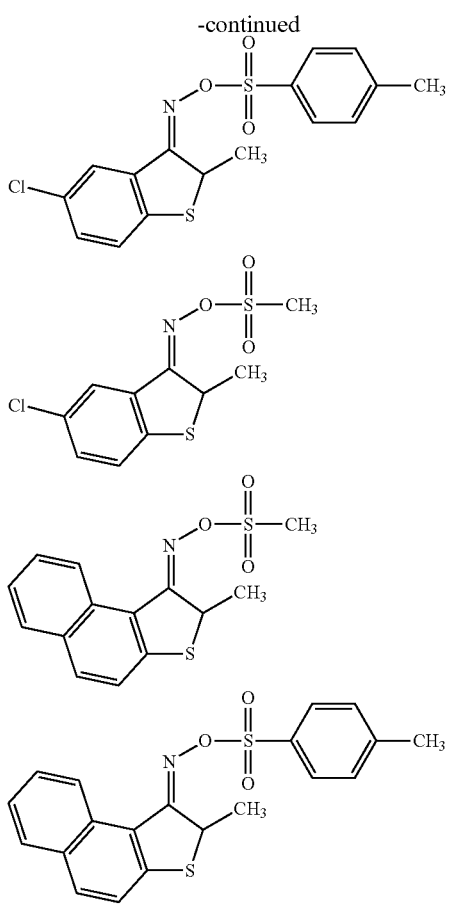

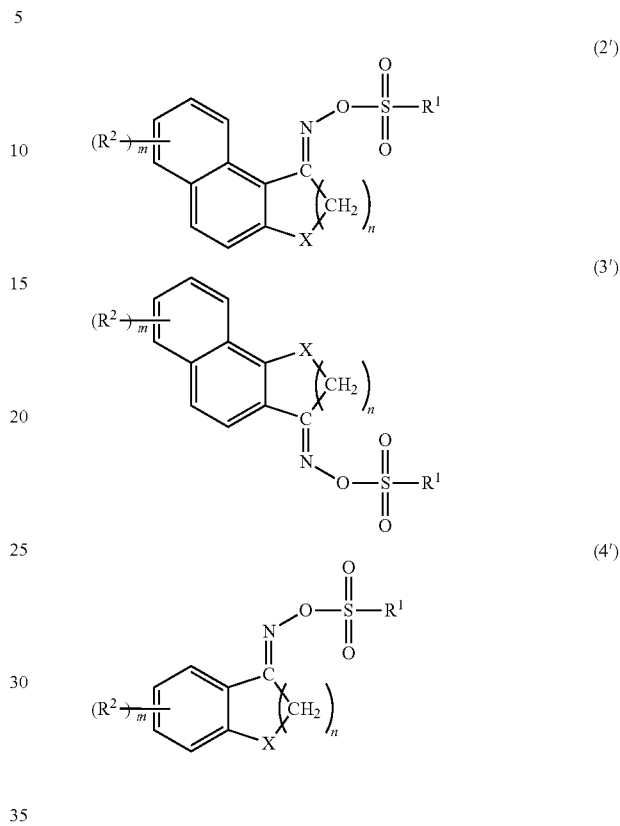

The content of Component A in the first photosensitive resin composition of the present invention is preferably 0.1 to 10 parts by weight relative to 100 parts by weight of Component B, and more preferably 0.5 to 10 parts by weight. When the content of Component A is at least 0.1 parts by weight, it is easy to obtain a desired sensitivity, and when it is no greater than 10 parts by weight, it is easy to obtain a coated film that is transparent. (Component A') Oxime sulfonate compound represented by Formula (1')

The second photosensitive resin composition of the present invention comprises (Component A') an oxime sulfonate compound represented by Formula (1').

The oxime sulfonate compound represented by Formula (1') (Component A') is a photo-acid generator that generates an acid in response to actinic radiation.

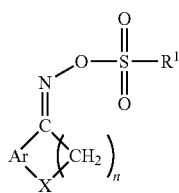

(In Formula (1'), $R^1$ denotes an alkyl group, an aryl group, or a heteroaryl group, Ar denotes an o-arylene group or an o-heteroarylene group, X denotes O or S, and n denotes 1 or 2.)

Furthermore, Component A' is more preferably a compound represented by Formula (2'), Formula (3'), or Formula (4').

(In Formula (2') to Formula (4'), $R^1$ denotes an alkyl group, an aryl group, or a heteroaryl group, each $R^2$ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6.)

In Formulae (1') to (4') above, $R^1$ has the same meaning as $R^1$ in Formulae (1) to (4) above, and preferred embodiments are also the same.

In Formula (1') above, Ar has the same meaning as $Ar^1$ in Formula (1) above, and preferred embodiments are also the same.

In Formulae (1') to (4') above, X denotes O or S.

In Formula (1'), X, Ar, the carbon atom of the oxime group, and —$(CH_2)_n$— are bonded to form a 5-membered ring or a 6-membered ring.

Furthermore, similarly, in Formulae (2') to (4'), the ring containing X as a ring member is a 5-membered ring or a 6-membered ring.

In Formulae (1') to (4') above, n denotes 1 or 2 and is preferably 1.

In Formulae (2') to (4') above, $R^2$ has the same meaning as $R^6$ in Formulae (2) to (4) above, and preferred embodiments are also the same.

Furthermore, in Formulae (2') to (4') above, m denotes an integer of 0 to 6 and is preferably an integer of 0 to 2, more preferably 0 or 1, and particularly preferably 0.

Moreover, with regard to the oxime sulfonate compound, the oxime may have either conformation (E, Z), or it may be a mixture thereof.

Specific examples of the oxime sulfonate compound represented by Formula (1') above include the compounds shown by compound examples A'-1 to A'-10 below, but the present invention is not limited thereby.

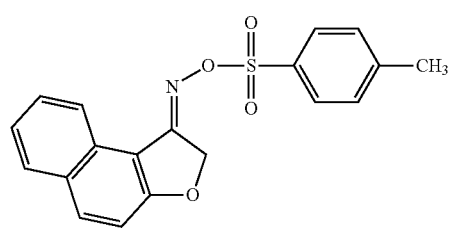
A'-1

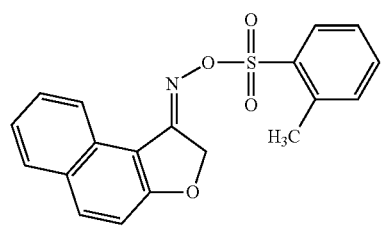
A'-2

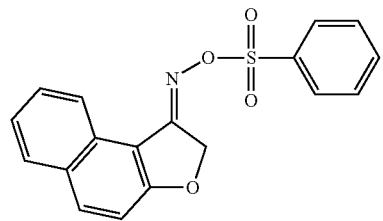
A'-3

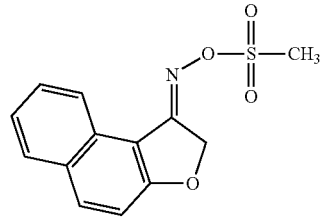
A'-4

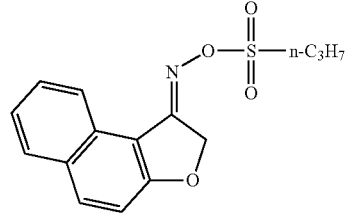
A'-5

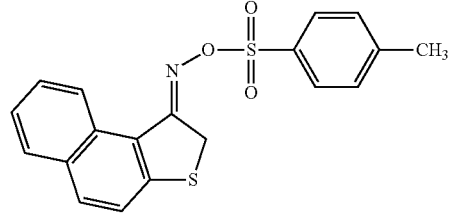
A'-6

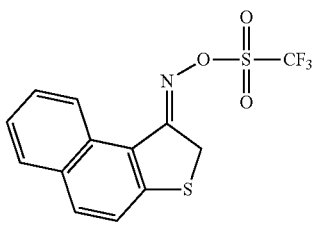
A'-7

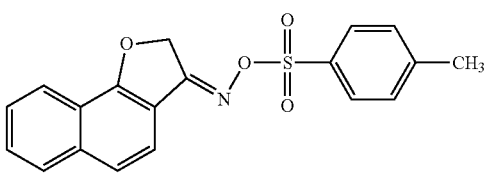
A'-8

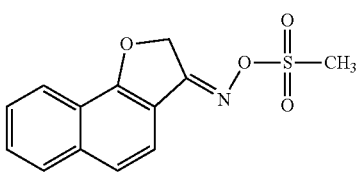
A'-9

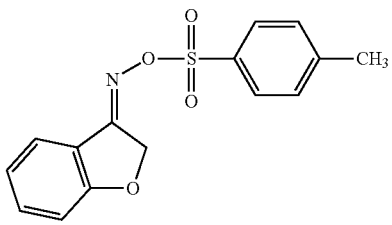
A'-10

The content of Component A' in the second photosensitive resin composition of the present invention is preferably 0.1 to 10 parts by weight relative to 100 parts by weight of Component B', and more preferably 0.5 to 10 parts by weight. When the content of Component A' is at least 0.1 parts by weight, it is easy to obtain a desired sensitivity, and when it is no greater than 10 parts by weight, it is easy to obtain a coated film that is transparent. (Component B) Resin comprising constituent unit having acid-decomposable group that is decomposed by acid to form carboxyl group or phenolic hydroxy group The first photosensitive resin composition of the present invention comprises (Component B) a resin comprising a constituent unit having an acid-decomposable group that is decomposed by an acid to form a carboxyl group or a phenolic hydroxy group.

The 'acid-decomposable group' referred to in the present invention means a functional group that, by decomposing in the presence of an acid, can form a carboxyl group or a phenolic hydroxy group, which had been protected by the acid-decomposable group.

The constituent units forming the copolymer (Component B) are explained in detail below.

<Constituent Unit Containing Acid-Decomposable Group>

The constituent unit containing an acid-decomposable group that is decomposed by an acid to form a carboxyl group or a phenolic hydroxy group (hereinafter, also called simply an 'acid-decomposable group') contained in Component B preferably comprises a constituent unit having a structure represented by Formula (Ia) or Formula (IIa) that is decomposed (dissociated) by an acid to form a carboxyl group or a constituent unit having a structure represented by Formula (Ib) or Formula (IIb) that is decomposed by an acid to form a phenolic hydroxy group.

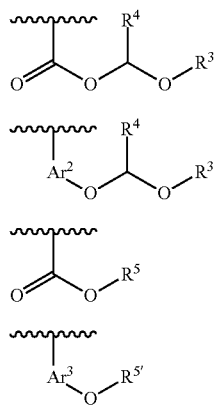

(In the Formulae, $R^3$ denotes an alkyl group or a cycloalkyl group, $R^4$ denotes an alkyl group, $R^3$ and $R^4$ may form a ring, $R^5$ denotes a tertiary alkyl group, $R^{5'}$ denotes a tertiary alkyl group or a tert-butoxycarbonyl group, $Ar^2$ and $Ar^3$ independently denote a divalent aromatic group, and a wavy line portion denotes the position of bonding to another structure.)

Among them, the constituent unit having an acid-decomposable group preferably has a structure represented by Formula (Ia) and/or Formula (Ib) above, more preferably a structure represented by Formula (Ia), and particularly preferably one represented by Formula (Ia) in which $R^3$ and $R^4$ form a ring.

<Case in which $R^3$ and $R^4$ do not Form Ring>

The alkyl group denoted by $R^3$ may be straight chain or branched. The number of carbons of the alkyl group denoted by $R^3$ is preferably 1 to 20, more preferably 1 to 10, and yet more preferably 1 to 7.

The number of carbons of the cycloalkyl group denoted by $R^3$ is preferably 3 to 20, more preferably 3 to 10, and yet more preferably 5 to 7.

When there is a substituent, the above number of carbons includes the number of carbons of the substituent.

Examples of the alkyl group denoted by $R^3$ include a methyl group, an ethyl group, an n-propyl group, an i-propyl group, an n-butyl group, an i-butyl group, a sec-butyl group, an n-pentyl group, a neopentyl group, an n-hexyl group, an n-heptyl group, an n-octyl group, a 2-ethylhexyl group, an n-nonyl group, and an n-decyl group.

Examples of the cycloalkyl group denoted by $R^3$ include a cyclopropyl group, a cyclobutyl group, a cyclopentyl group, a cyclohexyl group, a cycloheptyl group, a cyclooctyl group, a norbornyl group, and an isobornyl group.

The alkyl group and cycloalkyl group denoted by $R^3$ optionally have a substituent.

Examples of the substituent in the alkyl group and cycloalkyl group include an alkyl group having 1 to 10 carbons (a methyl group, an ethyl group, a propyl group, a butyl group, etc.), a cycloalkyl group having 3 to 10 carbons, an aryl group having 6 to 10 carbons, a halogen atom (a fluorine atom, a chlorine atom, a bromine atom, an iodine atom), a cyano group, a nitro group, a hydroxy group, and an alkoxy group having 1 to 10 carbons, and these substituents may further be substituted with the above substituent.

Furthermore, the alkyl group or cycloalkyl group denoted by $R^3$ is preferably an alkyl group having 1 to 10 carbons, a cycloalkyl group having 3 to 10 carbons, or an aralkyl group having 7 to 11 carbons, more preferably an alkyl group having 1 to 6 carbons, a cycloalkyl group having 3 to 6 carbons, or a benzyl group, yet more preferably an ethyl group or a cyclohexyl group, and particularly preferably an ethyl group.

The alkyl group denoted by $R^4$ may be straight chain or branched.

The number of carbons of the alkyl group denoted by $R^4$ is preferably 1 to 20, more preferably 1 to 10, and yet more preferably 1 to 7.

When there is a substituent, the above number of carbons includes the number of carbons of the substituent.

Furthermore, the alkyl group denoted by $R^4$ is preferably an alkyl group having 1 to 6 carbons, and particularly preferably a methyl group.

In Formula (Ib), $Ar^2$ denotes a divalent aromatic group and has $OCH(OR^3)(R^4)$ on the aromatic ring.

Examples of the divalent aromatic group denoted by $Ar^2$ include, but are not particularly limited to, a phenylene group, a substituted phenylene group, a naphthylene group, and a substituted naphthylene group, and it is preferably a phenylene group or a substituted phenylene group, more preferably a phenylene group, and yet more preferably a 1,4-phenylene group.

Furthermore, the divalent aromatic group denoted by $Ar^2$ optionally has a substituent on the aromatic ring; examples of the substituent include an alkyl group having 1 to 10 carbons (a methyl group, an ethyl group, a propyl group, a butyl group, etc.), a cycloalkyl group having 3 to 10 carbons, an aryl group having 6 to 10 carbons, a halogen atom (a fluorine atom, a chlorine atom, a bromine atom, an iodine atom), a cyano group, a nitro group, a hydroxy group, and an alkoxy group having 1 to 10 carbons, and these substituents may further be substituted with the above substituent.

As a carboxylic acid monomer that can form a constituent unit having a structure represented by Formula (Ia) above by its carboxyl group being protected, any monomer can be used as long as it can form a constituent unit having an acid-decomposable group by its carboxyl group being protected, and examples thereof include a monocarboxylic acid such as acrylic acid, methacrylic acid, crotonic acid, or α-methyl-p-carboxystyrene; and a dicarboxylic acid such as maleic acid, fumaric acid, citraconic acid, mesaconic acid, or itaconic acid. Furthermore, preferred examples of the constituent unit having an acid-decomposable group include a monomer unit derived from the above carboxylic acid in which the carboxyl group is protected.

As a monomer having a phenolic hydroxy group that can form a constituent unit having a structure represented by Formula (Ib) above by its phenolic hydroxy group being protected, any monomer can be used as long as it can form a constituent unit having an acid-decomposable group by its phenolic hydroxy group being protected, and preferred examples include a hydroxystyrene such as p-hydroxystyrene or α-methyl-p-hydroxystyrene, compounds described in paragraphs 0011 to 0016 of JP-A-2008-40183, 4-hydroxybenzoic acid derivatives described in paragraphs 0007 to 0010 of Japanese registered patent No. 2888454, the product of an addition reaction between 4-hydroxybenzoic acid and glycidyl methacrylate, and the product of an addition reaction between 4-hydroxybenzoic acid and glycidyl acrylate.

Among them, α-methyl-p-hydroxystyrene, compounds described in paragraphs 0011 to 0016 of JP-A-2008-40183, 4-hydroxybenzoic acid derivatives described in paragraphs 0007 to 0010 of Japanese registered patent No. 2888454, the product of an addition reaction between 4-hydroxybenzoic acid and glycidyl methacrylate, and the product of an addition reaction between 4-hydroxybenzoic acid and glycidyl acrylate are more preferable.

Among these structures, the constituent unit having an acid-decomposable group is particularly preferably a constituent unit represented by Formula (III).

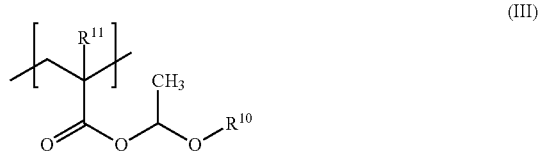

In Formula (III), $R^{10}$ denotes an alkyl group or a cycloalkyl group, and preferred embodiments of $R^{10}$ are the same as preferred embodiments of $R^3$ in Formula (Ia) and Formula (Ib).

Furthermore, in Formula (III), $R^{11}$ denotes a hydrogen atom or a methyl group.

Specific preferred examples of a radically polymerizable monomer used in order to form a constituent unit represented by Formula (III) include 1-ethoxyethyl methacrylate, 1-ethoxyethyl acrylate, 1-methoxyethyl methacrylate, 1-methoxyethyl acrylate, 1-n-butoxyethyl methacrylate, 1-n-butoxyethyl acrylate, 1-isobutoxyethyl methacrylate, 1-isobutoxyethyl acrylate, 1-(2-ethylhexyloxy)ethyl methacrylate, 1-(2-ethylhexyloxy)ethyl acrylate, 1-n-propoxyethyl methacrylate, 1-n-propoxyethyl acrylate, 1-cyclohexyloxyethyl methacrylate, 1-cyclohexyloxyethyl acrylate, 1-(2-cyclohexylethoxy)ethyl methacrylate, 1-(2-cyclohexylethoxy)ethyl acrylate, 1-benzyloxyethyl methacrylate, and 1-benzyloxyethyl acrylate, and 1-ethoxyethyl methacrylate and 1-ethoxyethyl acrylate are particularly preferable. With regard to these constituent units, one type may be used on its own or two or more types may be used in combination.

<Case in which $R^3$ and $R^4$ Form Ring>

$R^3$ and $R^4$ may form a ring. As an example of such a case, a 2-tetrahydropyranyl group and a 2-tetrahydrofuranyl group are preferable, and a 2-tetrahydrofuranyl group is particularly preferable.

Specific preferred examples of a radically polymerizable monomer used in order to form these constituent units include tetrahydro-2H-pyran-2-yl methacrylate, tetrahydro-2H-pyran-2-yl acrylate, tetrahydrofuran-2-yl methacrylate, and tetrahydrofuran-2-yl acrylate. Tetrahydrofuran-2-yl methacrylate and tetrahydrofuran-2-yl acrylate are particularly preferable.

As the radically polymerizable monomer used in order to form a constituent unit having an acid-decomposable group, a commercially available product may be used or one synthesized by a known method may be used. For example, it may be synthesized by reacting (meth)acrylic acid with a vinyl ether compound in the presence of an acid catalyst as described below.

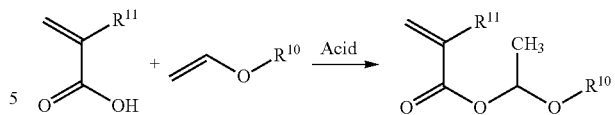

Here, $R^{10}$ and $R^{11}$ correspond to $R^{10}$ and $R^{11}$ in Formula (III) respectively.

Furthermore, the constituent unit having an acid-decomposable group may also be formed by polymerizing a monomer containing a carboxyl group or phenolic hydroxy group that is to be protected with a monomer described later or its precursor and then reacting the carboxyl group or the phenolic hydroxy group with a vinyl ether compound. Specific preferred examples of monomer units that are formed in this way are the same as those of monomer units derived from specific preferred examples of the radically polymerizable monomer.

In Formula (IIa) and Formula (IIb) above, $R^5$ denotes a tertiary alkyl group, $R^{5'}$ denotes a tertiary alkyl group or a tert-butoxycarbonyl group, $Ar^3$ denotes a divalent aromatic group, and a wavy line portion denotes the position of bonding to another structure.

The tertiary alkyl group denoted by $R^5$ and $R^{5'}$ is preferably one having 4 to 20 carbons, more preferably one having 4 to 14 carbons, and yet more preferably one having 4 to 8 carbons.

The tertiary alkyl group denoted by $R^5$, the tertiary alkyl group and tert-butoxycarbonyl group denoted by $R^{5'}$, and the divalent aromatic group denoted by $Ar^3$ optionally have a substituent, and examples of the substituent include an alkyl group having 1 to 10 carbons (a methyl group, an ethyl group, a propyl group, a butyl group, etc.), a cycloalkyl group having 3 to 10 carbons, an aryl group having 6 to 10 carbons, a halogen atom (a fluorine atom, a chlorine atom, a bromine atom, an iodine atom), a cyano group, a nitro group, a hydroxy group, and an alkoxy group having 1 to 10 carbons. These substituents may further be substituted with the above substituent.

Furthermore, the tertiary alkyl group denoted by $R^5$ and $R^{5'}$ is more preferably at least one type selected from the group consisting of groups represented by Formula (IV) below.

$$-C(R^{12}R^{13}R^{14}) \tag{IV}$$

In the Formula, $R^{12}$, $R^{13}$, and $R^{14}$ independently denote an alkyl group having 1 to 12 carbons, a cycloalkyl group having 3 to 12 carbons, an aryl group having 6 to 12 carbons, or an aralkyl group having or 7 to 12 carbons; alternatively, any two of $R^{12}$, $R^{13}$, and $R^{14}$ may be bonded to each other to form, together with the carbon atom to which they are bonded, a ring.

The alkyl group having 1 to 12 carbons denoted by $R^{12}$, $R^{13}$, and $R^{14}$ in Formula (IV) may be straight chain or branched chain, and examples thereof include a methyl group, an ethyl group, an n-propyl group, an i-propyl group, an n-butyl group, an i-butyl group, a sec-butyl group, a t-butyl group, an n-pentyl group, a neopentyl group, an n-hexyl group, a thexyl group (2,3-dimethyl-2-butyl group), an n-heptyl group, an n-octyl group, a 2-ethylhexyl group, an n-nonyl group, and an n-decyl group.

Examples of the cycloalkyl group having 3 to 12 carbons include a cyclopropyl group, a cyclobutyl group, a cyclopentyl group, a cyclohexyl group, a cycloheptyl group, a cyclooctyl group, a norbornyl group, and an isobornyl group.

Examples of the aryl group having 6 to 12 carbons include a phenyl group, a tolyl group, a xylyl group, a cumenyl group, and a 1-naphthyl group.

The aralkyl group having 7 to 12 carbons includes a benzyl group, an α-methylbenzyl group, a phenethyl group, and a naphthylmethyl group.

Furthermore, $R^{12}$, $R^{13}$, and $R^{14}$ may be bonded to each other to form, together with the carbon to which they are bonded, a ring. Examples of the ring structure when $R^{12}$ and $R^{13}$, $R^{12}$ and $R^{14}$, or $R^{13}$ and $R^{14}$ are bonded include a cyclobutyl group, a cyclopentyl group, a cyclohexyl group, a cycloheptyl group, a tetrahydrofuranyl group, an adamantyl group, and a tetrahydropyranyl group.

Furthermore, $R^5$ in Formula (IIa) is preferably a tertiary alkyl group having 4 to 12 carbons, more preferably a tertiary alkyl group having 4 to 8 carbons, and yet more preferably a t-butyl group.

Moreover, $R^{5'}$ in Formula (IIb) is preferably a tertiary alkyl group having 4 to 12 carbons or a tert-butoxycarbonyl group, more preferably a tertiary alkyl group having 4 to 12 carbons, and yet more preferably a t-butyl group.

In Formula (IIb), $Ar^3$ denotes a divalent aromatic group and has $OR^{5'}$ on the aromatic ring.

Preferred embodiments of $Ar^3$ in Formula (IIb) are the same as preferred embodiments of $Ar^2$ in Formula (Ib) above.

The constituent unit having an acid-decomposable group preferably contains a protected carboxyl group represented by Formula (IIa) above and/or a protected phenolic hydroxy group represented by Formula (IIb) above.

As a carboxylic acid monomer that can form a monomer unit having a structure represented by Formula (IIa) above by its carboxyl group being protected, any monomer may be used as long as it can become the constituent unit having an acid-decomposable group by its carboxyl group being protected, and preferred examples include carboxylic acid monomers described above in the explanation of Formula (Ia).

As a monomer having a phenolic hydroxy group that can form a monomer unit having a structure represented by Formula (IIb) above by its phenolic hydroxy group being protected, any monomer may be used as long as it can become the constituent unit having an acid-decomposable group by its phenolic hydroxy group being protected, and preferred examples include the monomers having a phenolic hydroxy group described above in the explanation of Formula (Ib).

Among these structures, the constituent unit having an acid-decomposable group is particularly preferably a constituent unit represented by Formula (V) below.

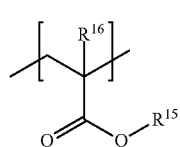

(V)

In Formula (V), $R^{15}$ denotes a tertiary alkyl group and $R^{16}$ denotes a hydrogen atom or a methyl group.

In Formula (V), preferred embodiments of $R^{15}$ are the same as preferred embodiments of $R^5$ in Formula (IIa).

Specific examples of a radically polymerizable monomer used in order to form a constituent unit represented by Formula (V) include tert-butyl methacrylate, tert-butyl acrylate, 2-methyl-2-adamantyl methacrylate, 2-methyl-2-adamantyl acrylate, 1-methylcyclohexyl methacrylate, and 1-methylcyclohexyl acrylate, and tert-butyl methacrylate and tert-butyl acrylate are preferable. With regard to these radically polymerizable monomers, one type may be used on its own or two or more types may be used in combination.

Specific preferred examples of the constituent unit having an acid-decomposable group include the monomer units below.

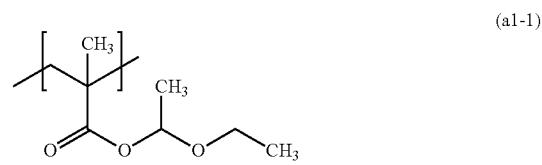

(a1-1)

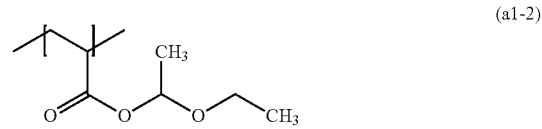

(a1-2)

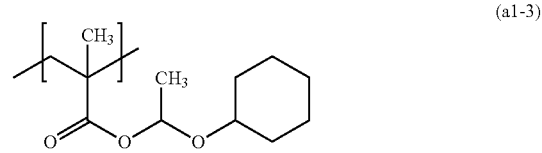

(a1-3)

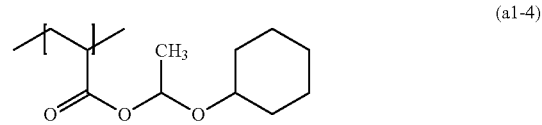

(a1-4)

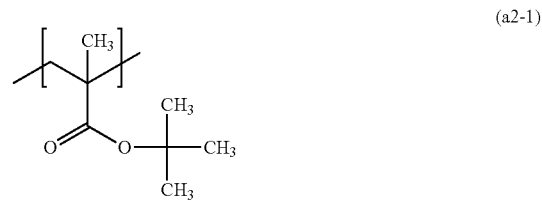

(a2-1)

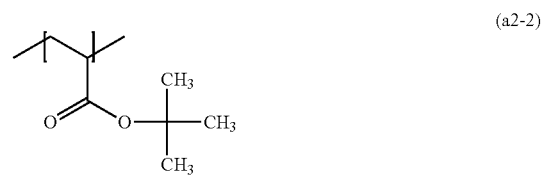

(a2-2)

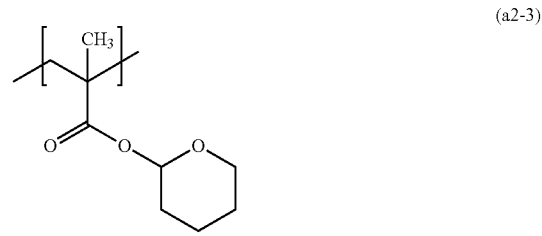

(a2-3)

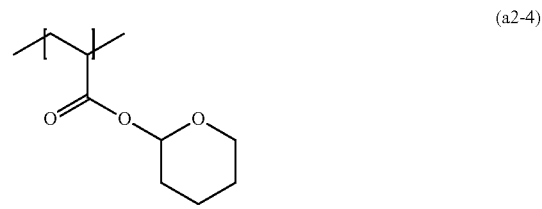

(a2-4)

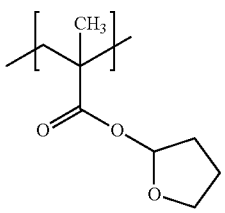

(a2-5)

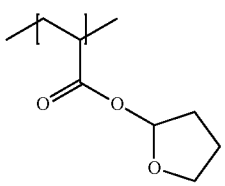

(a2-6)

Of the entire monomer units forming Component B, the content of the monomer unit forming the constituent unit having an acid-decomposable group is preferably 5 to 60 mole %, more preferably 10 to 50 mole %, and particularly preferably 10 to 40 mole %. By adding it in this proportion, a photosensitive resin composition having high sensitivity and wide exposure latitude is obtained.

<Constituent Unit Having Functional Group that can React with Carboxyl Group or Phenolic Hydroxy Group to Thus Form Covalent Bond>

Component B preferably comprises a constituent unit having a functional group that can react with a carboxyl group or a phenolic hydroxy group to thus form a covalent bond.

Examples of the functional group that can react with a carboxyl group or a phenolic hydroxy group to thus form a covalent bond include an epoxy group, an oxetanyl group, an acid anhydride group, an acid halide group, and an isocyanate group, and it is preferable that Component B is synthesized by use of a radically polymerizable monomer containing such a functional group. Among these functional groups, an epoxy group and/or an oxetanyl group are preferable.

The constituent unit having an epoxy group and/or an oxetanyl group is preferably a constituent unit having an alicyclic epoxy group and/or oxetanyl group, and is more preferably a constituent unit having an oxetanyl group.

The alicyclic epoxy group is a group in which an aliphatic ring and an epoxy ring form a fused ring, and specific preferred examples include a 3,4-epoxycyclohexyl group, a 2,3-epoxycyclohexyl group, and a 2,3-epoxycyclopentyl group.

The group having an oxetanyl group is not particularly limited as long as it has an oxetane ring, and a preferable example may be a (3-ethyloxetan-3-yl)methyl group.

The constituent unit having an epoxy group and/or an oxetanyl group may have at least one epoxy group or oxetanyl group in one monomer unit, and may also have one or more epoxy groups and one or more oxetanyl group, two or more epoxy groups, or two or more oxetanyl groups. There are no particular limitations, but the constituent unit preferably has one to three epoxy groups and/or oxetanyl groups in total, more preferably has one or two epoxy groups and/or oxetanyl groups in total, and yet more preferably has one epoxy group or one oxetanyl group.

Specific examples of the radical polymerizable monomer used to form the monomer unit having an epoxy group include glycidyl acrylate, glycidyl methacrylate, glycidyl α-ethylacrylate, glycidyl α-n-propylacrylate, glycidyl α-n-butylacrylate, 3,4-epoxybutyl acrylate, 3,4-epoxybutyl methacrylate, 6,7-epoxyheptyl acrylate, 6,7-epoxyheptyl methacrylate, 6,7-epoxyheptyl α-ethylacrylate, o-vinylbenzyl glycidyl ether, m-vinylbenzyl glycidyl ether, p-vinylbenzyl glycidyl ether, and the compound containing an alicyclic epoxy skeleton described in paragraphs 0031 to 0035 of Japanese Patent No. 4168443.

Examples of the radical polymerizable monomer used to form the constituent unit having an oxetanyl group include the (meth)acrylic acid esters having an oxetanyl group described in paragraphs 0011 to 0016 of JP-A-2001-330953.

Preferred examples of a radically polymerizable monomer used in order to form a constituent unit having an epoxy group and/or an oxetanyl group include a monomer containing a methacrylic acid ester structure and a monomer containing an acrylic acid ester structure.

Among these monomers, compounds having an alicyclic epoxy skeleton described in paragraphs 0034 to 0035 of Japanese registered patent No. 4168443 and (meth)acrylic acid esters having an oxetanyl group described in paragraphs 0011 to 0016 of JP-A-2001-330953 are more preferable, and (meth)acrylic acid esters having an oxetanyl group described in paragraphs 0011 to 0016 of JP-A-2001-330953 are particularly preferable. Among them, 3,4-epoxycyclohexylmethyl acrylate, 3,4-epoxycyclohexylmethyl methacrylate, (3-ethyloxetan-3-yl)methyl acrylate, and (3-ethyloxetan-3-yl)methyl methacrylate are preferable, and (3-ethyloxetan-3-yl)methyl acrylate and (3-ethyloxetan-3-yl)methyl methacrylate are most preferable. With regard to these monomers, one type may be used on its own or two or more types may be used in combination.

Specific preferred examples of the constituent unit having a functional group that can react with a carboxyl group or a phenolic hydroxy group to thus form a covalent bond include the constituent units illustrated below.

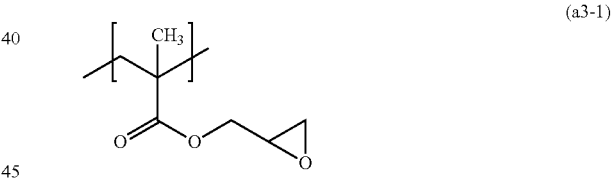

(a3-1)

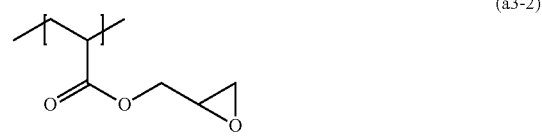

(a3-2)

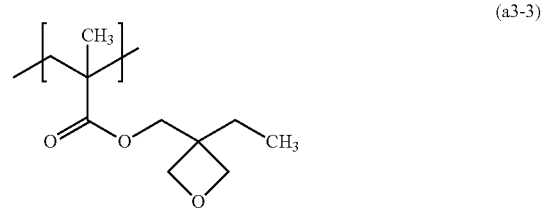

(a3-3)

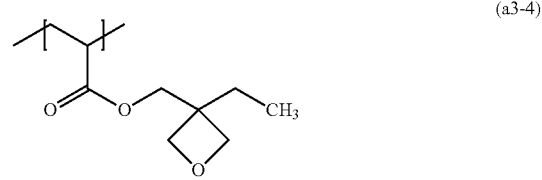

(a3-4)

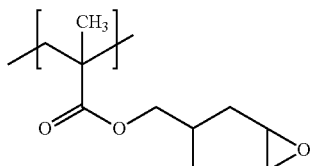
(a3-5)

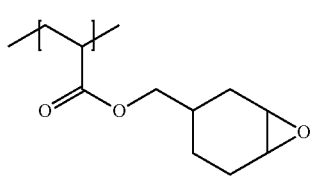
(a3-6)

Of the entire monomer units forming Component B, the content of the monomer unit that forms a constituent unit having a functional group that can react with a carboxyl group or a phenolic hydroxy group to thus form a covalent bond is preferably 10 to 80 mole %, more preferably 15 to 70 mole %, and particularly preferably 20 to 65 mole %. Due to it being contained at the above proportion, the physical properties of a cured film become good.

Among these constituent units, a constituent unit having an oxetanyl group is particularly preferable since the storage stability of a photosensitive composition is excellent.

<Other Constituent Unit>

Component B may comprise a constituent unit other than the above constituent unit as long as the effects of the present invention are not impaired.

Examples of a radically polymerizable monomer that forms the other constituent unit include compounds described in paragraphs 0021 to 0024 of JP-A-2004-264623.

Among them, from the viewpoint of improvement of electrical characteristics, alicyclic structure-containing (meth)acrylic acid esters such as dicyclopentanyl(meth)acrylate, cyclohexyl(meth)acrylate, and cyclohexyl acrylate are preferable.

Component B preferably comprises, as the other constituent unit, a constituent unit derived from at least one compound selected from the group consisting of a maleimide derivative, (meth)acrylic acid, and a hydroxy group-containing (meth)acrylate compound.

The maleimide derivative is preferably N-butylmaleimide or N-cyclohexylmaleimide.

The hydroxy group-containing (meth)acrylate compound is preferably hydroxyethyl(meth)acrylate, 2-hydroxypropyl (meth)acrylate, 3-hydroxypropyl(meth)acrylate, or 4-hydroxybutyl(meth)acrylate.

Furthermore, as a monomer that forms the other constituent unit, styrene is also preferable.

Among the entire monomer units forming Component B, the content of the monomer unit that forms the other constituent unit is preferably 0 to 50 mole %, more preferably 0 to 45 mole %, and particularly preferably 5 to 40 mole %. Due to it being contained at the above proportion, the physical properties of a cured film become good.

The weight-average molecular weight of Component B is preferably 1,000 to 100,000, and more preferably 2,000 to 50,000. In addition, the weight-average molecular weight in the present invention is preferably a polystyrene-basis weight-average molecular weight measured by gel permeation chromatography (GPC).

Preferred examples of Component B are listed below, but the present invention is not limited thereby.

In addition, the weight-average molecular weight of the examples of Component B listed below is preferably 2,000 to 50,000.

1-Ethoxyethyl methacrylate/tert-butyl methacrylate/glycidyl methacrylate copolymer 1-Ethoxyethyl methacrylate/tert-butyl methacrylate/glycidyl methacrylate/methacrylic acid copolymer 1-Ethoxyethyl methacrylate/tetrahydro-2H-pyran-2-yl methacrylate/glycidyl methacrylate/methacrylic acid copolymer 1-Ethoxyethyl methacrylate/tert-butyl methacrylate/3,4-epoxycyclohexylmethyl methacrylate copolymer 1-Ethoxyethyl methacrylate/tert-butyl methacrylate/3,4-epoxycyclohexylmethyl methacrylate/methacrylic acid copolymer 1-Ethoxyethyl methacrylate/tert-butyl methacrylate/3,4-epoxycyclohexylmethyl methacrylate/(3-methacryloyloxy-2-hydroxypropyl) 4-hydroxybenzoate copolymer 1-Ethoxyethyl methacrylate/tert-butyl methacrylate/3,4-epoxycyclohexylmethyl methacrylate/(3-methacryloyloxypropyl) 4-hydroxybenzoate copolymer 1-Ethoxyethyl methacrylate/tert-butyl methacrylate/3,4-epoxycyclohexylmethyl methacrylate/(3-methacryloyloxypropyl) 4-hydroxybenzoate/2-hydroxyethyl methacrylate copolymer 1-Ethoxyethyl methacrylate/tert-butyl methacrylate/3,4-epoxycyclohexylmethyl methacrylate/(3-methacryloyloxypropyl) 4-hydroxybenzoate/methyl methacrylate copolymer 1-Ethoxyethyl methacrylate/tetrahydro-2H-pyran-2-yl methacrylate/3,4-epoxycyclohexyl methyl methacrylate/(3-methacryloyloxypropyl) 4-hydroxybenzoate copolymer 1-Ethoxyethyl methacrylate/tetrahydro-2H-pyran-2-yl methacrylate/3,4-epoxycyclohexylmethyl methacrylate/(3-methacryloyloxypropyl) 4-hydroxybenzoate/2-hydroxyethyl methacrylate copolymer 1-Ethoxyethyl methacrylate/tert-butyl methacrylate/3,4-epoxycyclohexylmethyl acrylate/(3-methacryloyloxypropyl) 4-hydroxybenzoate copolymer 1-Ethoxyethyl methacrylate/tert-butyl methacrylate/3,4-epoxycyclohexylmethyl acrylate/(3-methacryloyloxypropyl) 4-hydroxybenzoate/2-hydroxyethyl methacrylate copolymer 1-Ethoxyethyl methacrylate/tert-butyl methacrylate/(3-ethyloxetan-3-yl)methyl methacrylate copolymer 1-Ethoxyethyl methacrylate/tert-butyl methacrylate/(3-ethyloxetan-3-yl)methyl methacrylate/methacrylic acid copolymer 1-Ethoxyethyl methacrylate/tert-butyl methacrylate/(3-ethyloxetan-3-yl)methyl methacrylate/(3-methacryloyloxy-2-hydroxypropyl) 4-hydroxybenzoate copolymer 1-Ethoxyethyl methacrylate/tert-butyl methacrylate/(3-ethyloxetan-3-yl)methyl methacrylate/(3-methacryloyloxypropyl) 4-hydroxybenzoate copolymer 1-Ethoxyethyl methacrylate/2-methyl-2-adamantyl methacrylate/(3-ethyloxetan-3-yl)methyl methacrylate/(3-methacryloyloxypropyl) 4-hydroxybenzoate copolymer 1-Ethoxyethyl methacrylate/1-methyl-1-cyclohexyl methacrylate/(3-ethyloxetan-3-yl)methyl methacrylate/(3-methacryloyloxypropyl) 4-hydroxybenzoate copolymer 1-Ethoxyethyl methacrylate/tert-butyl methacrylate/(3-ethyloxetan-3-yl)methyl methacrylate/(2-methacryloyloxyethyl) 4-hydroxybenzoate copolymer 1-Ethoxyethyl methacrylate/tert-butyl methacrylate/(3-ethyloxetan-3-yl)methyl methacrylate/(6-methacryloyloxyhexyl) 4-hydroxybenzoate copolymer 1-Ethoxyethyl methacrylate/tert-butyl methacrylate/(3-ethyloxetan-3-yl)methyl methacrylate/(3-methacryloyloxypropyl) 4-hydroxybenzoate/2-hydroxyethyl methacrylate copolymer 1-Ethoxyethyl methacrylate/tert-butyl methacrylate/(3-ethyloxetan-3-yl)methyl methacrylate/(3-methacryloyloxypropyl) 4-hydroxybenzoate/methyl methacrylate copolymer 1-Ethoxyethyl methacrylate/tetrahydro-2H-pyran-2-yl methacrylate/(3-ethyloxetan-3-yl)methyl methacrylate/(3-methacryloyloxypropyl) 4-hydroxybenzoate copolymer 1-Ethoxyethyl methacrylate/tetrahydro-2H-pyran-2-yl methacrylate/(3-ethyloxetan-3-yl)methyl methacrylate/(3-methacryloyloxypropyl) 4-hydroxybenzoate/2-hydroxyethyl methacrylate copolymer 1-Ethoxyethyl methacrylate/tert-butyl methacrylate/(3-ethyloxetan-3-yl)methyl acrylate/(3-methacryloyloxypropyl) 4-hydroxybenzoate copolymer 1-Ethoxyethyl methacrylate/tert-butyl methacrylate/(3-ethyloxetan-3-yl)methyl acrylate/(3-methacryloyloxypropyl) 4-hydroxybenzoate/2-hydroxyethyl methacrylate copolymer 1-(Cyclohexyloxy)ethyl methacrylate/tert-butyl methacrylate/3,4-epoxycyclohexylmethyl methacrylate copolymer 1-(Cyclohexyloxy)ethyl methacrylate/tert-butyl methacrylate/3,4-epoxycyclohexyl methyl methacrylate/(3-methacryloyloxypropyl) 4-hydroxybenzoate/2-hydroxyethyl methacrylate copolymer 1-(Cyclohexyloxy)ethyl methacrylate/tert-butyl methacrylate/(3-ethyloxetan-3-yl)methyl methacrylate copolymer 1-(Cyclohexyloxy)ethyl methacrylate/tert-butyl methacrylate/(3-ethyloxetan-3-yl)methyl methacrylate/(3-methacryloyloxypropyl) 4-hydroxybenzoate/2-hydroxyethyl methacrylate copolymer 1-(Cyclohexyloxy)ethyl methacrylate/tetrahydro-2H-pyran-2-yl methacrylate/3,4-epoxycyclohexylmethyl methacrylate/(3-methacryloyloxypropyl) 4-hydroxybenzoate/2-hydroxyethyl methacrylate copolymer 1-(Cyclohexyloxy)ethyl methacrylate/tetrahydro-2H-pyran-2-yl methacrylate/(3-ethyloxetan-3-yl)methyl methacrylate/(3-methacryloyloxypropyl) 4-hydroxybenzoate/2-hydroxyethyl methacrylate copolymer 1-Ethoxyethyl ether of (3-methacryloyloxypropyl) 4-hydroxybenzoate/tert-butyl methacrylate/(3-ethyloxetan-3-yl)methyl methacrylate/methacrylic acid copolymer 1-Ethoxyethyl ether of (3-methacryloyloxypropyl) 4-hydroxybenzoate/tert-butoxycarbonyl group-protected α-methyl-para-hydroxystyrene/(3-ethyloxetan-3-yl)methyl methacrylate/methacrylic acid copolymer 1-Ethoxyethyl ether of (2-methacryloyloxyethyl) 4-hydroxybenzoate/tert-butyl group-protected 4-hydroxyphenyl methacrylate/(3-ethyloxetan-3-yl)methyl methacrylate/methacrylic acid copolymer 1-Ethoxyethyl methacrylate/styrene/glycidyl methacrylate/methacrylic acid copolymer 1-Ethoxyethyl methacrylate/N-cyclohexylmaleimide/glycidyl methacrylate/methacrylic acid copolymer Tetrahydrofuran-2-yl methacrylate/(tricyclo[5.2.1.0$^{2,6}$]decan-8-yl)methacrylate/(3-ethyloxetan-3-yl)methyl methacrylate/methacrylic acid copolymer Tetrahydrofuran-2-yl methacrylate/(tricyclo[5.2.1.0$^{2,6}$]decan-8-yl) methacrylate/glycidyl methacrylate/methacrylic acid copolymer With regard to Component B, one type may be used on its own or two or more types may be used in combination.

The content of Component B in the first photosensitive resin composition of the present invention is preferably 20 to 99 wt % relative to the total solids content of the photosensitive resin composition, more preferably 40 to 97 wt %, and yet more preferably 60 to 95 wt %. When the content is in this range, the pattern forming properties when developed are good. The solids content of the photosensitive resin composition referred to here means the amount after removing volatile components such as solvent.

In addition, in the photosensitive resin composition of the present invention, (Component B″) a resin other than Component B may be used in combination as long as the effects of the present invention are not impaired. Here, the content of the resin other than Component B (Component B″) is preferably smaller than the content of Component B from the viewpoint of develop ability.

(Component B′) (Meth)Acrylic Copolymer Comprising Constituent Unit Having Acid-Decomposable Group that is Decomposed by Acid to Form Carboxyl Group The second photosensitive resin composition of the present invention comprises (Component B′) a (meth)acrylic copolymer comprising a constituent unit having an acid-decomposable group that is decomposed by an acid to form a carboxyl group.

The 'acid-decomposable group' referred to here has the same definition as for (Component B) and means a functional group that, by being decomposed in the presence of an acid, can form a carboxyl group, which had been protected by the acid-decomposable group.

Furthermore, the '(meth)acrylic polymer' in the present invention is an addition-polymerization type resin and is a polymer comprising a constituent unit derived from (meth)acrylic acid and/or an ester thereof. (Meth)acrylic acid means methacrylic acid and/or acrylic acid.

The constituent units forming Component B′ are explained in detail below.

<Constituent Unit Containing Acid-Decomposable Group that is Decomposed by Acid to Form Carboxyl Group>

Component B′ comprises a constituent unit having an acid-decomposable group that is decomposed by an acid to form a carboxyl group.

The acid-decomposable group is preferably an acetal group represented by Formula (I) below or a tertiary ester group represented by Formula (II) below, and is more preferably an acetal group represented by Formula (I) below.

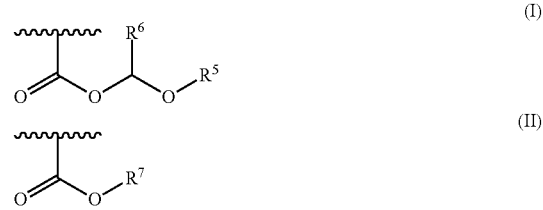

(In Formulae (I) and (II), $R^5$ denotes an alkyl group or a cycloalkyl group, $R^6$ denotes an alkyl group, $R^5$ and $R^6$ may form a ring, $R^7$ denotes a tertiary alkyl group, and a wavy line portion denotes the position of bonding to another structure.)

<Case in which $R^5$ and $R^6$ do not Form Ring>

In Formula (I), $R^5$ has the same meaning as $R^3$ in Formula (Ia) above, and preferred embodiments are also the same.

Furthermore, in Formula (I), $R^6$ has the same meaning as $R^4$ in Formula (Ia) above, and preferred embodiments are also the same.

<Case in which $R^5$ and $R^6$ Form Ring>

$R^5$ and $R^6$ may form a ring. As such a case, a 2-tetrahydropyranyl group and a 2-tetrahydrofuranyl group are preferable, and a 2-tetrahydrofuranyl group is particularly preferable.

The constituent unit having a carboxyl group protected by an acid-decomposable group preferably has a group represented by Formula (I) and/or Formula (II) above.

As a carboxylic acid monomer that can form a constituent unit having a group represented by Formula (I) and/or Formula (II) above by a carboxyl group being protected, any monomer may be used as long as it can become a constituent unit having an acid-decomposable group by a carboxyl group being protected, and examples include a monocarboxylic acid such as acrylic acid, methacrylic acid, crotonic acid, or α-methyl-p-carboxystyrene; and a dicarboxylic acid such as maleic acid, fumaric acid, citraconic acid, mesaconic acid, or itaconic acid. Furthermore, preferred examples of the constituent unit having an acid-decomposable group include a monomer unit derived from the above carboxylic acid in which the carboxyl group has been protected.

Specific preferred examples of a radically polymerizable monomer used in order to form a constituent unit having a group represented by Formula (I) include 1-ethoxyethyl methacrylate, 1-ethoxyethyl acrylate, 1-methoxyethyl methacrylate, 1-methoxyethyl acrylate, 1-n-butoxyethyl methacrylate, 1-n-butoxyethyl acrylate, 1-isobutoxyethyl methacrylate, 1-isobutoxyethyl acrylate, 1-(2-ethylhexyloxy)ethyl methacrylate, 1-(2-ethylhexyloxy)ethyl acrylate, 1-n-propoxyethyl methacrylate, 1-n-propoxyethyl acrylate, 1-cyclohexyloxyethyl methacrylate, 1-cyclohexyloxyethyl acrylate, 1-(2-cyclohexylethoxy)ethyl methacrylate, 1-(2-cyclohexylethoxy)ethyl acrylate, 1-benzyloxyethyl methacrylate, 1-benzyloxyethyl acrylate, tetrahydro-2H-pyran-2-yl methacrylate, tetrahydro-2H-pyran-2-yl acrylate, tetrahydrofuran-2-yl methacrylate, and tetrahydrofuran-2-yl acrylate. 1-Ethoxyethyl methacrylate, 1-ethoxyethyl acrylate, tetrahydrofuran-2-yl methacrylate, and tetrahydrofuran-2-yl acrylate are particularly preferable. With regard to these radically polymerizable monomers, one type may be used on its own or two or more types may be used in combination.

As the radically polymerizable monomer used in order to form a constituent unit having an acid-decomposable group that is decomposed by an acid to form a carboxyl group, a commercially available product may be used, or one synthesized by a known method may be used. For example, it may be synthesized as described above by reacting (meth)acrylic acid with a vinyl ether compound in the presence of an acid catalyst.

Furthermore, the constituent unit having an acid-decomposable group that is decomposed by an acid to form a carboxyl group may be formed by polymerizing a monomer containing a carboxyl group that is to be protected with a carboxylic acid monomer or a precursor thereof and then reacting the carboxyl group with a vinyl ether compound. Specific preferred examples of a monomer unit formed as above include a monomer unit derived from the specific preferred examples of the radically polymerizable monomer.

In Formula (II) above, $R^7$ has the same meaning as $R^5$ in Formula (IIa) above, and preferred embodiments are also the same.

The constituent unit having an acid-decomposable group that is decomposed by an acid to form a carboxyl group preferably has a tertiary ester group represented by Formula (II) above.

As the carboxylic acid monomer that can form a constituent unit having a group represented by Formula (II) above by a carboxyl group being protected, any monomer may be used as long as it can become a constituent unit having an acid-decomposable group by a carboxyl group being protected, and preferred examples include carboxylic acid monomers described above in the explanation of Formula (I).

Among these structures, the constituent unit having a carboxyl group protected by the acid-decomposable group is particularly preferably a constituent unit represented by Formula (IV) below.

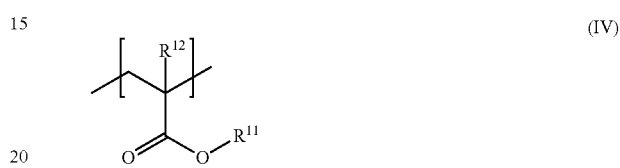

In Formula (IV), $R^{11}$ denotes a tertiary alkyl group and $R^{12}$ denotes a hydrogen atom or a methyl group.

In addition, in Formula (IV), preferred embodiments of $R^{11}$ are the same as preferred embodiments of $R^7$ in Formula (II).

Specific preferred examples of radically polymerizable monomers used in order to form a constituent unit represented by Formula (IV) include t-butyl methacrylate, t-butyl acrylate, 2-methyl-2-adamantyl methacrylate, 2-methyl-2-adamantyl acrylate, 1-methylcyclohexyl methacrylate, and 1-methylcyclohexyl acrylate, and t-butyl methacrylate and t-butyl acrylate are particularly preferable. With regard to these constituent units, one type may be used on its own or two or more types may be used in combination.

Specific preferred examples of the constituent unit having a carboxyl group protected by an acid-decomposable group include the constituent units below.

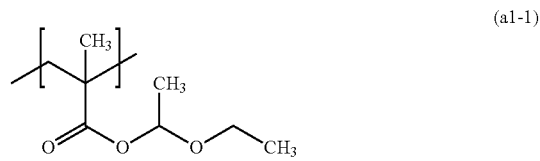

(a1-1)

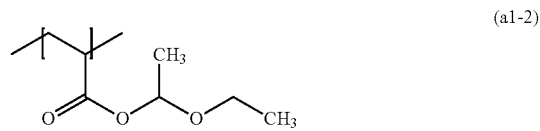

(a1-2)

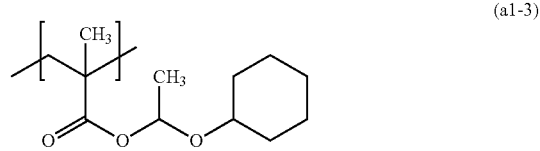

(a1-3)

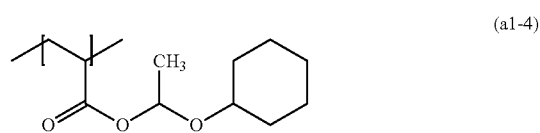

(a1-4)

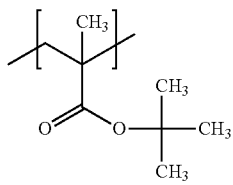 (a2-1)

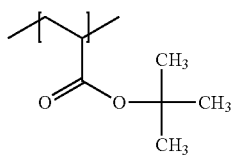 (a2-2)

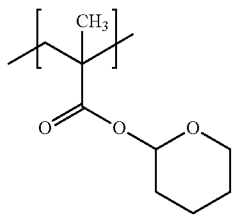 (a2-3)

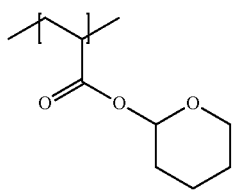 (a2-4)

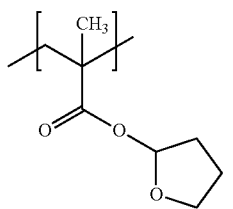 (a2-5)

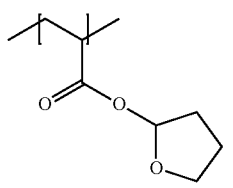 (a2-6)

Of the entire monomer units forming Component B', the content of the monomer unit that forms a constituent unit having an acid-decomposable group is preferably 5 to 60 mole %, more preferably 10 to 50 mole %, and particularly preferably 10 to 40 mole %. When it is contained at the above proportion, a photosensitive resin composition having high sensitivity and a wide exposure latitude is obtained.

<Constituent Unit Having Functional Group that can React with Carboxyl Group to Form Covalent Bond>

Component B' preferably comprises a constituent unit having a functional group that can react with a carboxyl group to form a covalent bond.

Examples of the constituent unit having a functional group that can react with a carboxyl group to form a covalent bond include the same examples as those cited for the constituent unit having a functional group that can react with a carboxyl group or a phenolic hydroxy group to thus form a covalent bond of Component B, and preferred embodiments are also the same.

Of the entire monomer units forming Component B', the content of the monomer unit that forms a constituent unit having a functional group that can react with a carboxyl group to form a covalent bond is preferably 10 to 80 mole %, more preferably 15 to 70 mole %, and particularly preferably 20 to 65 mole %. Due to it being contained at the above proportion, the physical properties of a cured film become good.

Among these constituent units, a constituent unit having an oxetanyl group is particularly preferable since the photosensitive composition has excellent storage stability.

<Other Constituent Unit>

Component B' may comprise a constituent unit other than the above constituent unit as long as the effects of the present invention are not impaired. As the other constituent unit, those cited as examples for the other constituent unit in Component B above can be cited, and preferred embodiments are also the same.

Of the entire monomer units forming Component B', the content of the monomer unit that forms the other constituent unit is preferably 0 to 50 mole %, more preferably 0 to 45 mole %, and particularly preferably 5 to 40 mole %. Due to it being contained at the above proportion, the physical properties of a cured film become good.

The weight-average molecular weight of Component B' is preferably 1,000 to 100,000, and more preferably 2,000 to 50,000. In addition, the weight-average molecular weight in the present invention is preferably a polystyrene-basis weight-average molecular weight measured by gel permeation chromatography (GPC).

Preferred examples of Component B' are listed below, but the present invention is not limited thereby.

The weight-average molecular weight of the examples of Component B' listed below is preferably 2,000 to 50,000. Furthermore, the numbers separated by a '/' below denote the copolymerization molar ratio of the corresponding monomers.

1-Ethoxyethyl methacrylate/tert-butyl methacrylate/glycidyl methacrylate=30/40/30 copolymer 1-Ethoxyethyl methacrylate/glycidyl methacrylate/methacrylic acid=40/40/20 copolymer 1-Ethoxyethyl methacrylate/glycidyl methacrylate/methacrylic acid/2-hydroxyethyl methacrylate=40/30/10/20 copolymer Tetrahydro-2H-pyran-2-yl methacrylate/glycidyl methacrylate/methacrylic acid=35/45/20 copolymer 1-Ethoxyethyl methacrylate/tert-butyl methacrylate/(3-ethyloxetan-3-yl)methyl methacrylate=30/40/30 copolymer 1-Ethoxyethyl methacrylate/(3-ethyloxetan-3-yl)methyl methacrylate/methacrylic acid=40/45/15 copolymer 1-Ethoxyethyl methacrylate/(3-ethyloxetan-3-yl)methyl methacrylate/methacrylic acid/2-hydroxyethyl methacrylate=40/30/18/12 copolymer 1-(Cyclohexyloxy)ethyl methacrylate/tert-butyl methacrylate/3,4-epoxycyclohexylmethyl methacrylate 40/30/15/15 copolymer 1-(Cyclohexyloxy)ethyl methacrylate/methacrylic acid/(3-ethyloxetan-3-yl)methyl methacrylate=40/10/50 copolymer 1-Ethoxyethyl methacrylate/N-cyclohexylmaleimide/glycidyl methacrylate/methacrylic acid=35/10/40/15 copolymer Tetrahydrofuran-2-yl methacrylate/glycidyl methacrylate/methacrylic acid=30/50/20 copolymer Tetrahydrofuran-2-yl methacrylate/glycidyl methacrylate/methacrylic acid/2-hydroxyethyl methacrylate=25/40/20/15 copolymer Tetrahydrofuran-2-yl methacrylate/(3-ethyloxetan-3-yl)methyl methacrylate/methacrylic acid=40/50/10 copolymer Tetrahydrofuran-2-yl methacrylate/(3-ethyloxetan-3-yl)methyl methacrylate/methacrylic acid/2-hydroxyethyl methacrylate=40/30/10/20 copolymer tert-Butyl methacrylate/glycidyl methacrylate/methacrylic acid=40/40/20 copolymer tert-Butyl methacrylate/glycidyl methacrylate/methacrylic acid/2-hydroxyethyl methacrylate=30/40/10/20 copolymer With regard to Component B', one type may be used on its own or two or more types may be used in combination.

The content of Component B' in the second photosensitive resin composition of the present invention is preferably 20 to 99 wt % relative to the entire solids content of the photosensitive resin composition, more preferably 40 to 97 wt %, and yet more preferably 60 to 95 wt %. When the content is in this range, the pattern forming properties when developed are good. The solids content of the photosensitive resin composition referred to here means the amount after removing volatile components such as the solvent (Component C).

The second photosensitive resin composition of the present invention may use in combination a resin other than Component B' as long as the effects of the present invention are not impaired. Here, the content of the resin other than Component B' is preferably smaller than the content of Component B' from the viewpoint of developability.

(Component C) Solvent

The first photosensitive resin composition and the second photosensitive resin composition of the present invention comprise (Component C) a solvent. In addition, the first photosensitive resin composition of the present invention and the second photosensitive resin composition of the present invention are collectively called the photosensitive resin composition of the present invention, or also called simply the photosensitive resin composition.

The first photosensitive resin composition of the present invention is prepared as a solution in which Component A and Component B, which are essential components, and optional components described later are dissolved in the solvent (Component C). Furthermore, the second photosensitive resin composition of the present invention is prepared as a solution in which Component A' and Component B', which are essential components, and an optional components described later are dissolved in the solvent (Component C).

As the solvent used in the photosensitive resin composition of the present invention, a known solvent can be used, and examples include ethylene glycol monoalkyl ethers, ethylene glycol dialkyl ethers, ethylene glycol monoalkyl ether acetates, propylene glycol monoalkyl ethers, propylene glycol dialkyl ethers, propylene glycol monoalkyl ether acetates, diethylene glycol dialkyl ethers, diethylene glycol monoalkyl ether acetates, dipropylene glycol monoalkyl ethers, dipropylene glycol dialkyl ethers, dipropylene glycol monoalkyl ether acetates, esters, ketones, amides, and lactones. Examples of the solvent used in the photosensitive resin composition of the present invention include those described in paragraph 0074 of JP-A-2009-258722.

These solvents can be used singly, or in combination of two or more kinds, and it is preferable to use singly or in combination of two kinds.

The content of (Component C) solvent in the photosensitive resin composition of the present invention is preferably 50 to 3,000 parts by weight, more preferably 100 to 2,000 parts by weight, and yet more preferably 150 to 1,500 parts by weight, per 100 parts by weight of Component A.

(Component D) Sensitizer

The photosensitive resin composition of the present invention preferably comprises (Component D) a sensitizer.

As the sensitizer that can be used in the present invention, any sensitizer may be used without particular limitation as long as it absorbs actinic radiation and sensitizes Component A or Component A' in accordance with an electron transfer mechanism or an energy transfer mechanism.

The sensitizer is preferably an anthracene derivative, an acridone derivative, a thioxanthone derivative, a coumarin derivative, a base styryl derivative, or a distyrylbenzene derivative.

The anthracene derivative is preferably anthracene, 9,10-dibutoxyanthracene, 9,10-dichloroanthracene, 2-ethyl-9,10-dimethoxyanthracene, 9-hydroxymethylanthracene, 9-bromoanthracene, 9-chloroanthracene, 9,10-dibromoanthracene, 2-ethylanthracene, or 9,10-dimethoxyanthracene.

The acridone derivative is preferably acridone, N-butyl-2-chloroacridone, N-methylacridone, 2-methoxyacridone, or N-ethyl-2-methoxyacridone.

The thioxanthone derivative is preferably thioxanthone, diethylthioxanthone, 1-chloro-4-propoxythioxanthone, 2-chlorothioxanthone, 2-isopropylthioxanthone, or 4-isopropylthioxanthone.

The coumarin derivative is preferably coumarin-1, coumarin-6H, coumarin-110, or coumarin-102.

Examples of the base styryl derivative include 2-(4-dimethylaminostyryl)benzoxazole, 2-(4-dimethylaminostyryl)benzothiazole, and 2-(4-dimethylaminostyryl)naphthothiazole.

Examples of the distyrylbenzene derivative include distyrylbenzene, di(4-methoxystyryl)benzene, and di(3,4,5-trimethoxystyryl)benzene.

Specific examples of the sensitizer include those shown below. Here, Me denotes a methyl group, Et denotes an ethyl group, and Bu denotes a butyl group.

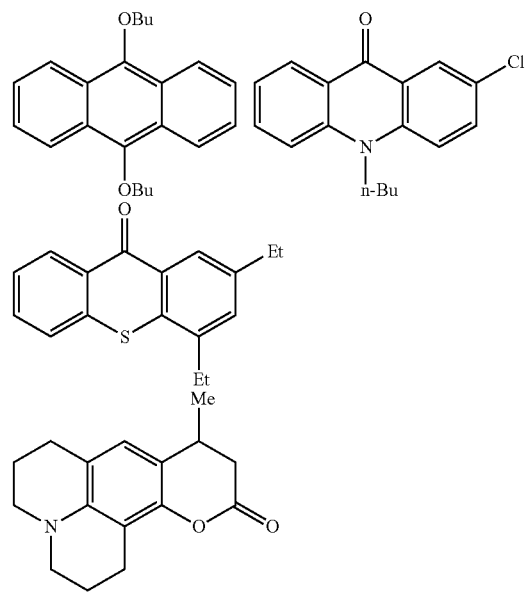

-continued

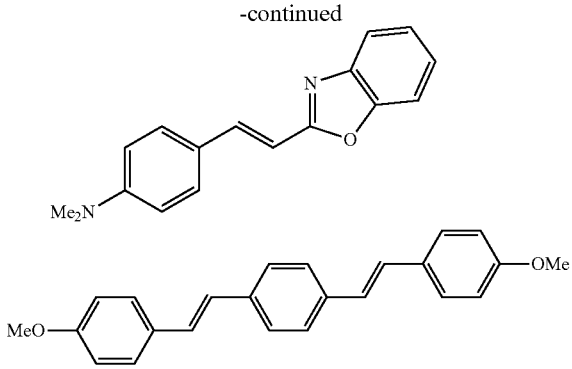

In regard to the sensitizer, commercially available products may be used, or the sensitizer may be synthesized by a known synthesis method.

Furthermore, with regard to the sensitizers, one type may be used on its own or two or more types may be used in combination.

The addition amount of the sensitizer is preferably 20 to 300 parts by weight, and particularly preferably 30 to 200 parts by weight, based on 100 parts by weight of Component A or Component A'.

<Other Components>

To the photosensitive resin composition of the present invention (the first photosensitive resin composition and the second photosensitive resin composition of the present invention) there may be added as necessary, as optional components, (Component E) an adhesion improving agent, (Component F) a surfactant, (Component G) a crosslinking agent, (Component H) an antioxidant, (Component I) a basic compound, (Component J) a plasticizer, and (Component K) a thermal radical generator, as well as a thermal acid generator, a UV absorber, a thickener, an organic or inorganic precipitation inhibitor, etc., which are known additives and are described below.

(Component E) Adhesion Improving Agent

The photosensitive resin composition of the present invention may comprise (Component E) an adhesion improving agent.

The adhesion improving agent that can be used in the photosensitive resin composition of the present invention is a compound that improves adhesion between an insulating film and an inorganic substance as a substrate such as, for example, a silicon compound such as silicon, silicon oxide, or silicon nitride or a metal such as gold, copper, or aluminum. Specific examples thereof include a silane coupling agent and a thiol-based compound. The silane coupling agent used as the adhesion improving agent in the present invention is for the purpose of modifying the interface, and a known material may be used without particular limitation.

Preferable examples of the silane coupling agent include γ-aminopropyltrimethoxysilane, γ-aminopropyltriethoxysilane, γ-glycidoxypropyltrialkoxysilane, γ-glycidoxypropylalkyldialkoxysilane, γ-methacryloxypropyltrialkoxysilane, γ-methacryloxypropylalkyldialkoxysilane, γ-chloropropyltrialkoxysilane, γ-mercaptopropyltrialkoxysilane, β-(3,4-epoxycyclohexyl)ethyltrialkoxysilane, and vinyltrialkoxysilane.

Among these, γ-glycidoxypropyltrialkoxysilane, and γ-methacryloxypropyltrialkoxysilane are more preferable, and γ-glycidoxypropyltrialkoxysilane is yet more preferable.

These can be used singly, or in combination of two or more kinds. These are effective in the enhancement of the adhesiveness to the substrate, and are also effective in the regulation of the taper angle with the substrate.

The content of Component E in the photosensitive resin composition of the present invention is preferably 0.1 to 20 parts by weight, and more preferably 0.5 to 10 parts by weight, based on 100 parts by weight of Component B or Component B'.

(Component F) Surfactant

The photosensitive resin composition of the present invention may comprise (Component F) a surfactant.

As the surfactant, any one of anionic, cationic, nonionic, or amphoteric surfactants may be used, and a nonionic surfactant is preferable.

Examples of the nonionic surfactant include a polyoxyethylene higher alkyl ether, a polyoxyethylene higher alkylphenyl ether, a polyoxyethylene glycol higher fatty acid diester, and a silicone-based or fluorine-based surfactant. Further examples include product names such as the KP (Shin-Etsu Chemical Co., Ltd.), Polyflow (Kyoeisha Chemical Co., Ltd.), Eftop (JEMCO), Megafac (DIC Corporation), Fluorad (Sumitomo 3M Limited), AsahiGuard and Surflon (Asahi Glass Co., Ltd.), PolyFox (OMNOVA), etc. series.

Preferred examples of the surfactant include a copolymer comprising constituent unit A and constituent unit B represented by Formula (W) below and having a polystyrene-basis weight-average molecular weight (Mw) of at least 1,000 but no greater than 10,000 as measured by gel permeation chromatography when dissolved in tetrahydrofuran (THF).

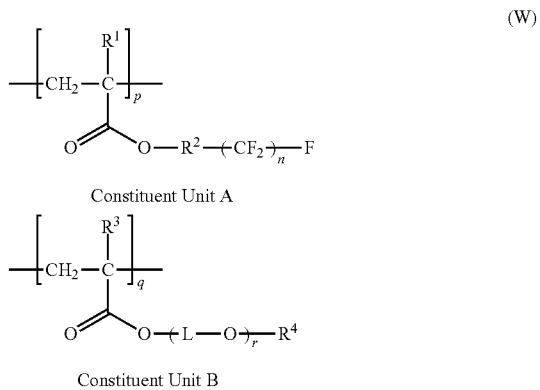

(W)

(In Formula (W), $R^1$ and $R^3$ independently denote a hydrogen atom or a methyl group, $R^2$ denotes a straight-chain alkylene group having 1 to 4 carbons, $R^4$ denotes a hydrogen atom or an alkyl group having 1 to 4 carbons, L denotes an alkylene group having 3 to 6 carbons, p and q are weight percentages showing polymerization ratio, p being a value of at least 10 wt % but no greater than 80 wt % and q being a value of at least 20 wt % but no greater than 90 wt %, r denotes an integer of at least 1 but no greater than 18, and n is an integer of at least 1 but no greater than 10.)

L above is preferably a branched alkylene group represented by Formula (L') below. $R^5$ in Formula (L') denotes an alkyl group having 1 to 4 carbons; from the viewpoint of miscibility and wettability toward a surface to be coated it is preferably an alkyl group having 1 to 3 carbons, and more preferably an alkyl group having 2 or 3 carbons. The sum (p+q) of p and q is preferably p+q=100, that is, 100 wt %.

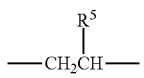
(L')

The weight-average molecular weight (Mw) of the copolymer is more preferably at least 1,500 but no greater than 5,000.

With regard to these surfactants, one type may be used on its own or two or more types may be used in combination.

The amount of Component F added in the photosensitive resin composition of the present invention is preferably no greater than 10 parts by weight relative to 100 parts by weight of Component B or Component B', more preferably 0.01 to 10 parts by weight, and yet more preferably 0.01 to 1 parts by weight.

(Component G) Crosslinking Agent

The photosensitive resin composition of the present invention preferably comprises (Component G) a crosslinking agent.

The crosslinking agent is for example a compound having at least two epoxy groups or oxetanyl groups per molecule, an alkoxymethyl group-containing crosslinking agent, or a compound having at least one ethylenically unsaturated double bond, which are described below. Adding the crosslinking agent enables a cured film to be a stronger film.

<Compound Having at Least Two Epoxy Groups or Oxetanyl Groups Per Molecule>

Specific examples of the compound having at least two epoxy groups per molecule include a bisphenol A epoxy resin, a bisphenol F epoxy resin, a phenol novolac epoxy resin, a cresol novolac epoxy resin, and an aliphatic epoxy resin.

They may be obtained as commercial products. Examples of the bisphenol A epoxy resin include JER827, JER828, JER834, JER1001, JER1002, JER1003, JER1055, JER1007, JER1009, and JER1010 (all manufactured by Japan Epoxy Resins Co., Ltd.) and EPICLON860, EPICLON1050, EPICLON1051, and EPICLON1055 (all manufactured by DIC Corporation), examples of the bisphenol F epoxy resin include JER806, JER807, JER4004, JER4005, JER4007, and JER4010 (all manufactured by Japan Epoxy Resins Co., Ltd), EPICLON830 and EPICLON835 (both manufactured by DIC Corporation), and LCE-21 and RE-602S (both manufactured by Nippon Kayaku Co., Ltd.), examples of the phenol novolac epoxy resin include JER152, JER154, and JER157S70 (all manufactured by Japan Epoxy Resins Co., Ltd) and EPICLON N-740, EPICLON N-740, EPICLON N-770, and EPICLON N-775 (all manufactured by DIC Corporation), examples of the cresol novolac epoxy resin include EPICLON N-660, EPICLON N-665, EPICLON N-670, EPICLON N-673, EPICLON N-680, EPICLON N-690, and EPICLON N-695 (all manufactured by DIC Corporation) and EOCN-1020 (manufactured by Nippon Kayaku Co., Ltd.), and examples of the aliphatic epoxy resin include ADEKA RESIN EP-4080S, ADEKA RESIN EP-4085S, and ADEKA RESIN EP-4088S (all manufactured by ADEKA Corporation) and Celloxide 2021P, Celloxide 2081, Celloxide 2083, Celloxide 2085, EHPE3150, EPOLEAD PB 3600, and EPOLEAD PB 4700 (all manufactured by Daicel Chemical Industries, Ltd.). Other examples include ADEKA RESIN EP-4000S, ADEKA RESIN EP-4003S, ADEKA RESIN EP-4010S, and ADEKA RESIN EP-4011S (all manufactured by ADEKA Corporation) and NC-2000, NC-3000, NC-7300, XD-1000, EPPN-501, and EPPN-502 (all manufactured by ADEKA Corporation). With regard to these, one type may be used on its own or two or more types may be used in combination.

Among them, preferred examples include a bisphenol A epoxy resin, a bisphenol F epoxy resin, and a phenol novolac epoxy resin. A bisphenol A epoxy resin is particularly preferable.

Specific examples of the compound having at least two oxetanyl groups per molecule include Aron oxetane OXT-121, OXT-221, OX-SQ, and PNOX (all manufactured by Toagosei Co., Ltd.).

Furthermore, the compound containing an oxetanyl group may be used on its own or as a mixture with a compound containing an epoxy group.

The amount of compound having at least two epoxy groups or oxetanyl groups per molecule added to the photosensitive resin composition is preferably 1 to 50 parts by weight relative to 100 parts by weight of the total amount of Component B or Component B', and more preferably 3 to 30 parts by weight.

<Alkoxymethyl Group-Containing Crosslinking Agent>

The alkoxymethyl group-containing crosslinking agent is preferably an alkoxymethylated melamine, an alkoxymethylated benzoguanamine, an alkoxymethylated glycoluril, an alkoxymethylated urea, etc. They are obtained by converting a methylol group of a methylolated melamine, a methylolated benzoguanamine, a methylolated glycoluril, or a methylolated urea into an alkoxymethyl group. The type of this alkoxymethyl group is not particularly limited, and examples include a methoxymethyl group, an ethoxymethyl group, a propoxymethyl group, and a butoxymethyl group, and from the viewpoint of the amount of outgassing generated a methoxymethyl group is particularly preferably.

Among these alkoxymethyl group-containing crosslinking agents, preferred examples of the crosslinking agent include an alkoxymethylated melamine, an alkoxymethylated benzoguanamine, and an alkoxymethylated glycoluril, and from the viewpoint of transparency an alkoxymethylated glycoluril is particularly preferable.

These alkoxymethyl group-containing crosslinking agents are available as commercial products; preferred examples include Cymel 300, 301, 303, 370, 325, 327, 701, 266, 267, 238, 1141, 272, 202, 1156, 1158, 1123, 1170, 1174, UFR65, and 300 (all manufactured by Mitsui Cyanamid) and Nikalac MX-750, -032, -706, -708, -40, -31, -270, -280, -290, Nikalac MS-11, Nikalac MW-30HM, -100LM, and -390, (all manufactured by Sanwa Chemical Co., Ltd.).

The amount of alkoxymethyl group-containing crosslinking agent added when the alkoxymethyl group-containing crosslinking agent is used in the photosensitive resin composition of the present invention is preferably 0.05 to 50 parts by weight relative to 100 parts by weight of Component B or Component B', and more preferably 0.5 to 10 parts by weight. When added in this range, desirable alkali solubility when developing and excellent solvent resistance of a cured film are obtained.

<Compound Having at Least One Ethylenically Unsaturated Double Bond>

As the compound having at least one ethylenically unsaturated double bond, a (meth)acrylate compound such as a monofunctional (meth)acrylate, a difunctional (meth)acrylate, or a tri- or higher-functional (meth)acrylate may suitably be used.

Examples of the monofunctional (meth)acrylate include 2-hydroxyethyl(meth)acrylate, carbitol(meth)acrylate, isobornyl(meth)acrylate, 3-methoxybutyl(meth)acrylate, and 2-(meth)acryloyloxyethyl-2-hydroxypropyl phthalate.

Examples of the difunctional (meth)acrylate include ethylene glycol di(meth)acrylate, 1,6-hexanediol di(meth)acrylate, 1,9-nonanediol di(meth)acrylate, polypropylene glycol di(meth)acrylate, tetraethylene glycol di(meth)acrylate, bisphenoxyethanolfluorene diacrylate, and bisphenoxyethanolfluorene diacrylate.

Examples of the tri- or higher-functional (meth)acrylate include trimethylolpropane tri(meth)acrylate, pentaerythritol tri(meth)acrylate, tri((meth)acryloyloxyethyl)phosphate, pentaerythritol tetra(meth)acrylate, dipentaerythritol penta(meth)acrylate, and dipentaerythritol hexa(meth)acrylate.

With regard to these compounds having at least one ethylenically unsaturated double bond, one type may be used on its own or two or more types may be used in combination.

The proportion used of the compound having at least one ethylenically unsaturated double bond in the photosensitive resin composition of the present invention is preferably no greater than 50 parts by weight relative to 100 parts by weight of Component B or Component B', and more preferably no greater than 30 parts by weight. Using the compound having at least one ethylenically unsaturated double bond at the above proportion enables the heat resistance, surface hardness, etc. of an insulating film obtained from the photosensitive resin composition of the present invention to be improved. When the compound having at least one ethylenically unsaturated double bond is added, it is preferable to add (Component K) a thermal radical generator.

(Component H) Antioxidant

The photosensitive resin composition of the present invention may comprise (Component H) an antioxidant.

As Component H, the photosensitive resin composition can contain a known antioxidant. When Component H is added, coloration of the cured film can be prevented. The antioxidant also advantages that it can also reduce a decrease in the film thickness due to decomposition, and has excellent heat resistance and transparency.

Examples of such an antioxidant include phosphorus-based antioxidants, hydrazides, hindered amine-based antioxidants, sulfur-based antioxidants, phenol-based antioxidants, ascorbic acid compounds, zinc sulfate, sugars, nitrites, sulfites, thiosulfates, and hydroxylamine derivatives. Among these, phenol-based antioxidants are particularly preferable from the viewpoint of the coloration of the cured film and a decrease in the film thickness. These may be used singly, or may be used in combination of two or more kinds.

Examples of commercially available products of the phenolic antioxidants include ADK STAB AO-60 (manufactured by Adeka Corp.), ADK STAB AO-80 (manufactured by Adeka Corp.), and IRGANOX 1098 (manufactured by Ciba-Geigy Japan, Ltd.).

The content of Component H is preferably 0.1 wt % to 6 wt %, more preferably 0.2 wt % to 5 wt %, and particularly preferably 0.5 wt % to 4 wt %, based on the total solids content of the photosensitive resin composition. When the content is in this range, sufficient transparency of the formed film is obtained, and the sensitivity at the time of pattern formation also becomes satisfactory.

Furthermore, various ultraviolet absorbents, metal inactivators and the like described in "Kobunshi Tenkazai no Shintenkai (New Development of Polymer Additives; Nikkan Kogyo Shimbun, Ltd.)" may also be added to the photosensitive resin composition of the present invention, as additives other than the antioxidant.

(Component I) Basic Compound

The photosensitive resin composition of the present invention may comprise (Component I) a basic compound.

As the basic compound, any compound among those used in chemically amplified resists can be selected and used. Examples include an aliphatic amine, an aromatic amine, a heterocyclic amine, a quaternary ammonium hydroxide, and a quaternary ammonium salt of a carboxylic acid.

Specific examples of the basic compound include compounds described in paragraphs 0052 to 0056 of JP-A-2009-98616.

The basic compound that can be used in the present invention may be used singly, or two or more kinds may be used in combination. However, it is preferable to use two or more kinds in combination, it is more preferable to use two kinds in combination, and it is yet more preferable to use two kinds of heterocyclic amines in combination.

The content of Component I in the photosensitive resin composition of the present invention is preferably 0.001 to 1 part by weight, and more preferably 0.005 to 0.2 parts by weight, based on 100 parts by weight of Component B or Component B'.

(Component J) Plasticizer

The photosensitive resin composition of the present invention may comprise (Component J) a plasticizer.

Examples of the plasticizer include dibutyl phthalate, dioctyl phthalate, didodecyl phthalate, polyethylene glycol, glycerin, dimethyl glycerin phthalate, dibutyl tartrate, dioctyl adipate, and triacetylglycerin.

The content of Component J in the photosensitive resin composition of the present invention is preferably 0.1 to 30 parts by weight, and more preferably 1 to 10 parts by weight, based on 100 parts by weight of Component B or Component B'.

(Component K) Thermal Radical Generator

The photosensitive resin composition of the present invention may contain (Component K) a thermal radical generator, and when the composition contains an ethylenic unsaturated compound such as a compound having at least one ethylenic unsaturated double bond described above, it is preferable that the composition contain (Component K) the thermal radical generator.

As the thermal radical generator, a known thermal radical generator can be used.

The thermal radical generator is a compound which generates a radical under the action of thermal energy, and initiates or accelerates the polymerization reaction of a polymerizable compound. When the thermal radical generator is added, the cured film thus obtained becomes tougher, and heat resistance and solvent resistance may increase.

Preferable examples of the thermal radical generator include aromatic ketones, onium salt compounds, organic peroxides, thio compounds, hexaarylbiimidazole compounds, keto oxime ester compounds, borate compounds, azinium compounds, metallocene compounds, active ester compounds, compounds having a carbon-halogen bond, azo compounds, and bibenzyl compounds.

The thermal radical generator may be used singly, or can also be used in combination of two or more kinds.

The content of Component K in the photosensitive resin composition of the present invention is preferably 0.01 to 50 parts by weight, more preferably 0.1 to 20 parts by weight, and most preferably 0.5 to 10 parts by weight, based on 100 parts by weight of Component B or Component B', from the viewpoint of an enhancement of the film properties.

(Method for Forming Cured Film)

The method for forming a cured film of the present invention is now explained.

The method for forming a cured film of the present invention comprises steps (1) to (5) below.

(1) An application step of applying the photosensitive resin composition of the present invention onto a substrate (2) A solvent removal step of removing solvent from the photosensitive resin composition that has been applied (3) An exposure step of exposing to actinic radiation the photosensitive resin composition that has been applied (4) A development step of developing the exposed photosensitive resin composition by means of an aqueous developer (5) A post-baking step of thermally curing the developed photosensitive resin composition The respective steps are explained in sequence below.

In the application step (1), the photosensitive resin composition of the present invention is applied onto a substrate to thus form a wet film containing a solvent.

In the solvent removal step (2), the solvent is removed from the film that has been applied, preferably by means of reduced pressure and/or heat, to thus form a dry film on the substrate.

In the exposure step (3), the film obtained via the solvent removal step is preferably irradiated with actinic radiation having a wavelength of at least 300 nm but no greater than 450 nm. In this step, Component A or Component A' decomposes to thus generate an acid. Due to the catalytic action of the acid generated, the acid-decomposable group contained in Component B or Component B' is hydrolyzed, thus forming a carboxyl group or a phenolic hydroxy group.

In order to accelerate the hydrolysis reaction, in regions where the acid catalyst is generated a post-exposure thermal treatment: Post Exposure Bake (hereinafter, also called 'PEB') may be carried out as necessary. The PEB enables formation of the carboxyl group from the acid-decomposable group to be promoted.

Since the acid-decomposable group of Component A or Component A' in the present invention has a low activation energy for decomposition by an acid, is easily decomposed by an acid derived from an acid generator upon exposure, and forms a carboxyl group or a phenolic hydroxy group, and a positive image may be formed by development without the need for carry out a PEB.

By carrying out a PEB at a relatively low temperature, it is possible to promote hydrolysis of the acid-decomposable group without causing a crosslinking reaction. The temperature at which a PEB is carried out is preferably at least 30° C. but no greater than 130° C., more preferably at least 40° C. but no greater than 110° C., and particularly preferably at least 50° C. but no greater than 80° C.

In the development step (4), it is preferable to develop polymer having free carboxyl groups or phenolic hydroxy groups using an alkaline developer. A positive image is formed by removing exposed regions containing the resin composition having carboxyl groups or phenolic hydroxy groups, which is easily dissolved in the alkaline developer.

In the post-baking step (5), a cured film may be formed by heating the positive image to thus thermally decompose the acid-decomposable group of Component B or Component B' and form a carboxyl group or a phenolic hydroxy group, and by crosslinking with for example an epoxy group and/or an oxetanyl group. This heating is preferably carried out at a high temperature of 150° C. or higher, more preferably at 180° C. to 250° C., and particularly preferably at 200° C. to 250° C. The heating time may be set as appropriate according to the heating temperature, etc., and is preferably in the range of 10 to 90 minutes.

Prior to the post-baking step, a step of irradiating the entire developed pattern with actinic radiation, preferably UV, may be added, thus promoting a crosslinking reaction by an acid generated by irradiation with actinic radiation.

A method for forming a cured film using the photosensitive resin composition of the present invention is now specifically explained.

<Method for Preparing Photosensitive Resin Composition>

The photosensitive resin composition is prepared by mixing Component A, Component B, and Component C, or Component A', Component B', and Component C, which are essential components, at a predetermined ratio by any method, and dissolving them by stirring. For example, solutions in which Component A and Component B or Component A' and Component B' are each dissolved in a solvent (Component C) in advance are prepared, and they are mixed at a predetermined ratio, thus preparing a resin composition. The composition solution thus prepared may also be used after filtering using a filter having a pore diameter of 0.2 μm, etc.

<Application Step and Solvent Removal Step>

A desired dry film may be obtained by applying the photosensitive resin composition of the present invention onto a predetermined substrate and removing the solvent by reducing the pressure and/or heating (pre-baking). With regard to the substrate, in the production of a liquid crystal display device, examples include a glass plate provided with a polarizing plate, with a black matrix layer or a color filter layer as necessary, and further with a transparent conductive circuit layer. A method for application onto the substrate is not particularly limited, and for example a slit coating method, a spray method, a roll coating method, a spin coating method, etc. may be used. Among them, a slit coating method is preferable from the viewpoint of suitability for a large-size substrate. The large-size substrate referred to here means a substrate having a dimension of each side of at least 1 m.

Furthermore, the heating conditions for the solvent removal step (2) are in a range in which the acid-decomposable group of Component B or Component B' in an unexposed portion does not decompose to make Component B or Component B' alkali-developable and, although depending on the type of each component and the mixing ratio, the conditions are preferably 80° C. to 130° C. and on the order of 30 to 120 seconds.

<Exposure Step>

In the exposure step, it is preferable to irradiate with actinic radiation a substrate having a film applied thereto via a mask having a predetermined pattern. Actinic radiation having a wavelength of at least 300 nm but no greater than 450 nm may preferably be used. After the exposure step, a thermal treatment (PEB) is carried out as necessary.

Exposure to actinic radiation may employ a low-pressure mercury lamp, a high-pressure mercury lamp, a super high pressure mercury lamp, an LED light source, a chemical lamp, a laser generator, etc.

When a mercury lamp is used, actinic radiation having a wavelength corresponding to the g-line (436 nm), the i-line (365 nm), the h-line (405 nm), etc. may preferably be used. The mercury lamp is preferable since it is more suitable for large area exposure than a laser.

When a laser is used, a solid (YAG) laser at 343 nm or 355 nm, an excimer laser at 351 nm (XeF), or a semiconductor laser at 375 nm or 405 nm may be used. Among them, from the viewpoint of stability, cost, etc. one at 355 nm or 405 nm is preferable. An applied film may be irradiated with the laser once or a plurality of times.

The energy density of the laser per pulse is preferably at least 0.1 mJ/cm$^2$ but no greater than 10,000 mJ/cm$^2$. In order to sufficiently cure an applied film, it is more preferably at least 0.3 mJ/cm$^2$, and most preferably at least 0.5 mJ/cm$^2$, and in order to prevent decomposition of an applied film by the phenomenon of ablation, it is more preferably no greater than 1,000 mJ/cm$^2$, and most preferably no greater than 100 mJ/cm$^2$. Furthermore, the pulse width is preferably at least 0.1 nsec but no greater than 30,000 nsec. In order to prevent decomposition of an applied film caused by the phenomenon of ablation, it is more preferably at least 0.5 nsec, and most preferably at least 1 nsec, and in order to improve the overlay precision when carrying out a scanning exposure it is more preferably no greater than 1,000 nsec, and most preferably no greater than 50 nsec.

Furthermore, the frequency of the laser is preferably 1 to 50,000 Hz, and more preferably 10 to 1,000 Hz. When the frequency of the laser is at least 1 Hz, the exposure treatment time does not become long, and when it is no greater than 50,000 Hz, the overlay precision when carrying out a scanning exposure becomes excellent.

In order to shorten the exposure treatment time, it is more preferably at least 10 Hz, and most preferably at least 100 Hz, and in order to improve the overlay precision when carrying out a scanning exposure it is more preferably no greater than 10,000 Hz, and most preferably no greater than 1,000 Hz.

A laser is more advantageous than a mercury lamp, from the viewpoint that focusing is easy, a mask for the pattern formation in the exposure step is unnecessary, and the cost can be reduced.

The exposing apparatus that can be used in the present invention is not particularly limited, but commercially available products such as Callisto (manufactured by V Technology Co., Ltd.), AEGIS (manufactured by V Technology Co., Ltd.), DF2200G (manufactured by Dainippon Screen Co., Ltd.) or the like can be used. Apparatuses other than those described above can also be suitably used.

Furthermore, if necessary, the irradiation light can also be regulated through a spectrometric filter such as a long wavelength cutoff filter, a short wavelength cutoff filter, or a band pass filter.

<Development Step>

In the development step, it is preferable to remove exposed regions using a basic developer to thus form an image pattern.

As the basic compound that can be used in the alkaline developer liquid, for example, aqueous solutions of alkali metal hydroxides such as lithium hydroxide, sodium hydroxide, and potassium hydroxide; alkali metal carbonates such as sodium carbonate and potassium carbonate; alkali metal hydrogen carbonates such as sodium hydrogen carbonate and potassium hydrogen carbonate; ammonium hydroxides such as tetramethylammonium hydroxide, tetraethylammonium hydroxide, and choline hydroxide; sodium silicate and sodium metasilicate can be used. Furthermore, an aqueous solution prepared by adding an appropriate amount of a water-soluble organic solvent such as methanol or ethanol, or a surfactant to an aqueous solution of an alkali can also be used as the developer liquid.

The pH of the developer liquid is preferably 10.0 to 14.0.

The development time is preferably 30 to 180 seconds, and the technique of development may be any of a paddling method and a dipping method. After the development, a desired pattern may be formed by performing washing under flowing water for 10 to 90 seconds.

<Post-Baking Step>

A pattern corresponding to unexposed regions obtained by development may be subjected to a thermal treatment using a heater such as a hotplate or an oven at a predetermined temperature of for example 180° C. to 250° C. for a predetermined time of for example 5 to 60 min. on a hotplate or 30 to 90 min. in an oven, to thus decompose the acid-decomposable group of Component B or Component B', generate the carboxyl group or the phenolic hydroxy group, and crosslink it by reaction with the functional group of Component B or Component B', thus forming a protective film or an interlayer insulating film having excellent heat resistance, hardness, etc. Furthermore, carrying out the thermal treatment under a nitrogen atmosphere may improve the transparency.

Prior to the heat treatment, it is preferable to expose the substrate with a pattern formed thereon by re-exposure to an active radiation and then post-baking (re-exposure/post-baking), to generate an acid from Component B or Component B' that is present in the unexposed area, and to thereby making the acid to function as a catalyst for accelerating crosslinking.

That is, the method for forming a cured film according to the present invention preferably includes a re-exposure step of re-exposing the substrate to an active radiation, between the development step and the post-baking step.

The exposure in the re-exposure step may be carried out by the same means as that used in the exposure step, but in the re-exposure step, it is preferable to perform full-area exposure on the side of the substrate where a film has been formed using the photosensitive resin composition of the present invention. A preferable dose of exposure for the re-exposure step is 100 to 1,000 mJ/cm$^2$.

In accordance with the photosensitive resin composition of the present invention, an interlayer insulating film having excellent insulation and high transparency even when baked at high temperature can be obtained. The interlayer insulating film formed using the photosensitive resin composition of the present invention has high transparency and excellent cured film physical properties, and is useful in application to an organic EL display device or a liquid crystal display device.

The organic EL display device and the liquid crystal display device of the present invention are not particularly limited as long as they have a planarization film, protective film, or interlayer insulating film formed using the photosensitive resin composition of the present invention, and examples include various types of known organic EL display devices and liquid crystal display devices having various structures.

Furthermore, the photosensitive resin composition of the present invention and the cured film of the present invention may be used, without being limited to the above applications, in various applications. For example, other than a planarization film, a protective film, and an interlayer insulating film, it may suitably be used for a spacer for maintaining a constant thickness of a liquid crystal layer in a liquid crystal display device, for a micro lens provided above a color filter in a solid state image sensor, etc.

FIG. 1 shows a schematic diagram of the constitution of one example of an organic EL display device. It shows a schematic sectional view of a substrate in a bottom emission type organic EL display device, and it has a planarization film 4.

A bottom gate type TFT 1 is formed above a glass substrate 6, and an insulating film 3 formed from Si$_3$N$_4$ is formed so as to cover the TFT 1. After a contact hole, which is not illustrated in the figure, is formed in the insulating film 3, wiring 2 (height 1.0 μm) is formed above the insulating film 3, the wiring 2 being connected to the TFT 1 via the contact hole. The wiring 2 is provided in order to provide a connection between the TFTs 1 or between the TFT 1 and an organic EL element formed in a subsequent step.

Furthermore, in order to planarize asperities due to formation of the wiring 2, a planarization layer 4 is formed above the insulating film 3 so as to bury asperities due to the wiring 2.

A bottom emission type organic EL element is formed above the planarization film 4. That is, a first electrode 5 formed from ITO is formed above the planarization film 4 so as to be connected to the wiring 2 via a contact hole 7. Furthermore, the first electrode 5 corresponds to a positive electrode of the organic EL element.

An insulating film 8 is formed in a shape that covers the periphery of the first electrode 5, and providing the insulating film 8 enables a short circuit between the first electrode 5 and a second electrode formed in a subsequent step to be prevented.

Moreover, although not illustrated in FIG. 1, a positive hole transport layer, an organic light-emitting layer, and an electron transport layer may be provided in sequence by vapor deposition via desired pattern masks, a second electrode is subsequently formed from Al on the entire surface above the substrate, and sealing with a sealing glass plate is carried out using a UV curing type epoxy resin, thus giving an active matrix type organic EL display device in which a TFT 1 is connected to each organic EL element in order to drive it.

Figure 2:
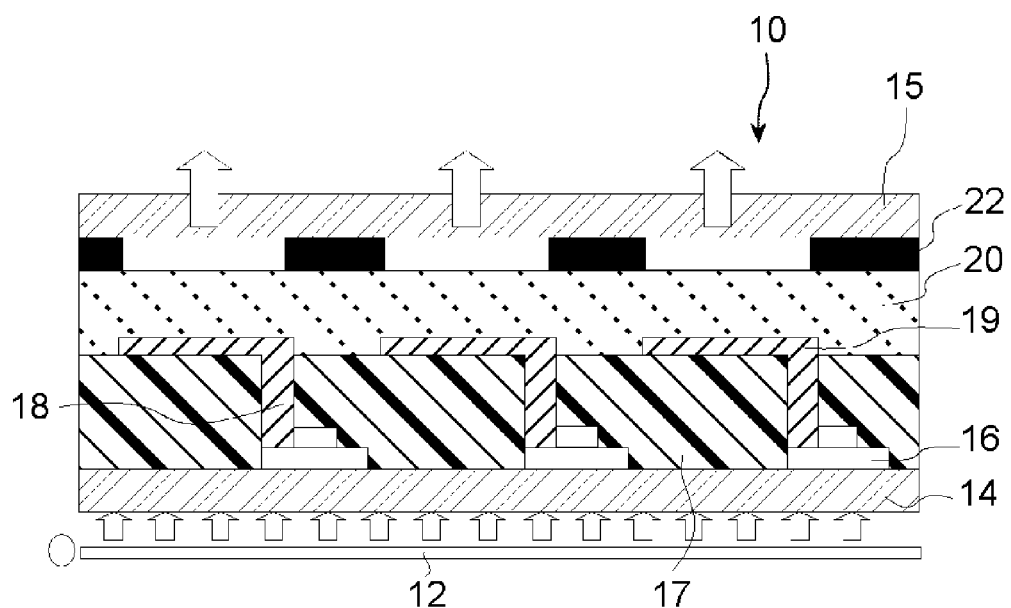
FIG. 2 is a schematic diagram of the constitution of one example of a liquid crystal display device, showing a schematic sectional view of an active matrix substrate in a liquid crystal display device, the substrate having a cured film 17, which is an interlayer insulating film.

FIG. 2 is a schematic sectional view showing one example of an active matrix type liquid crystal display device 10. This color liquid crystal display device 10 is a liquid crystal panel having a back light unit 12 on the reverse side, and the liquid crystal panel is provided with TFT 16 elements corresponding to all pixels disposed between two sheets of glass substrate 14 and 15 to which a polarizing film is affixed. Each element formed above the glass substrate has wired thereto through a contact hole 18 formed in a cured film 17 an ITO transparent electrode 19 forming a pixel electrode. Provided above the ITO transparent electrode 19 are a liquid crystal 20 layer and an RGB color filter 22 having a black matrix disposed thereon.

(Oxime Sulfonate Compound)

The oxime sulfonate compound of the present invention is an oxime sulfonate compound represented by Formula (1), and is a photo-acid generator that forms an acid in response to actinic radiation.

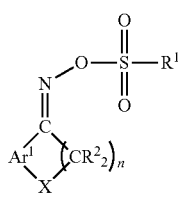

(1)

(In Formula (1), $R^1$ denotes an alkyl group, an aryl group, or a heteroaryl group, each $R^2$ independently denotes a hydrogen atom, an alkyl group, an aryl group, or a halogen atom, $Ar^1$ denotes an o-arylene group or an o-heteroarylene group, X denotes O or S, and n denotes 1 or 2. Here, of two or more $R^2$s present in the compound, at least one denotes an alkyl group, an aryl group, or a halogen atom.)

The oxime sulfonate compound represented by Formula (1) above, is preferably an oxime sulfonate compound represented by Formula (2), Formula (3) or Formula (4).

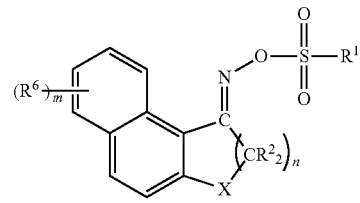

(2)

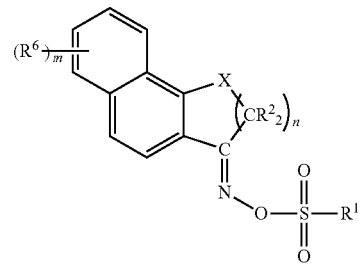

(3)

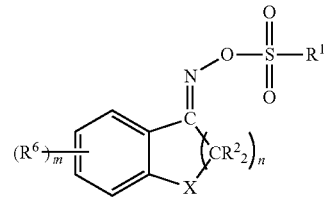

(4)

(In Formula (2) to Formula (4), $R^1$ denotes an alkyl group, an aryl group, or a heteroaryl group, each $R^2$ independently denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6. Here, of two or more $R^2$s present in the compound, at least one denotes an alkyl group, an aryl group, or a halogen atom.)

The alkyl group, aryl group, and heteroaryl group denoted by $R^1$ in the Formulae (1) to (4) optionally have a substituent.

The alkyl group denoted by $R^1$ in Formulae (1) to (4) is preferably an optionally substituted alkyl group having 1 to 30 carbons in total.

Examples of the substituent that the alkyl group denoted by $R^1$ may have include a halogen atom, an alkyloxy group, an aryloxy group, an alkylthio group, an arylthio group, an alkyloxycarbonyl group, an aryloxycarbonyl group, and an aminocarbonyl group.

Examples of the alkyl group denoted by $R^1$ include a methyl group, an ethyl group, an n-propyl group, an i-propyl group, an n-butyl group, an s-butyl group, a t-butyl group, an n-pentyl group, an n-hexyl group, an n-octyl group, an n-decyl group, an n-dodecyl group, a trifluoromethyl group, a perfluoropropyl group, a perfluorohexyl group, a benzyl group, a phenoxyethyl group, a methylthioethyl group, a phenylthioethyl group, an ethoxycarbonylethyl group, a phenoxycarbonylethyl group, and a dimethylaminocarbonylethyl group.

Among them, a methyl group, an ethyl group, an n-propyl group, an i-propyl group, an n-butyl group, an s-butyl group, a t-butyl group, an n-pentyl group, an n-hexyl group, an n-octyl group, an n-decyl group, an n-dodecyl group, a trifluoromethyl group, a perfluoropropyl group, a perfluorohexyl group, and a benzyl group are preferable.

In Formulae (1) to (4) above, the aryl group denoted by $R^1$ is preferably an optionally substituted aryl group having 6 to 30 carbons in total.

Examples of the substituent that the aryl group denoted by $R^1$ may have include a halogen atom, an alkyl group, an alkyloxy group, an aryloxy group, an alkylthio group, an arylthio group, an alkyloxycarbonyl group, an aryloxycarbonyl group, an aminocarbonyl group, a sulfonic acid group, an aminosulfonyl group, and an alkoxysulfonyl group.

Examples of the aryl group denoted by $R^1$ include a phenyl group, a p-methylphenyl group, a p-chlorophenyl group, a pentachlorophenyl group, a pentafluorophenyl group, an o-methoxyphenyl group, a p-phenoxyphenyl group, a p-methylthiophenyl group, a p-phenylthiophenyl group, a p-ethoxycarbonylphenyl group, a p-phenoxycarbonylphenyl group, and a p-dimethylaminocarbonylphenyl group.

Among them, a phenyl group, a p-methylphenyl group, a p-chlorophenyl group, a pentachlorophenyl group, a pentafluorophenyl group, an o-methoxyphenyl group, and a p-phenoxyphenyl group are preferable.

In Formulae (1) to (4) above, the heteroaryl group denoted by $R^1$ is preferably an optionally substituted heteroaryl group having 4 to 30 carbons in total.

Examples of the substituent that the heteroaryl group denoted by $R^1$ may have include a halogen atom, an alkyl group, an alkyloxy group, an aryloxy group, an alkylthio group, an arylthio group, an alkyloxycarbonyl group, an aryloxycarbonyl group, an aminocarbonyl group, a sulfonic acid group, an aminosulfonyl group, and an alkoxysulfonyl group.

In Formulae (1) to (4) above, with regard to the heteroaryl group denoted by $R^1$, at least one ring may be a heteroaromatic ring, and for example a heteroaromatic ring and a benzene ring may form a fused ring.

Examples of the heteroaryl group denoted by $R^1$ include a group formed by removing one hydrogen atom from a ring selected from the group consisting of a thiophene ring, a pyrrole ring, a thiazole ring, an imidazole ring, a furan ring, a benzothiophene ring, a benzothiazole ring, and a benzimidazole ring, these rings optionally having a substituent.

In Formulae (1) to (4) above, $R^2$ is preferably a hydrogen atom, an alkyl group, or an aryl group, and more preferably a hydrogen atom or an alkyl group.

In Formulae (1) to (4) above, of two or more $R^2$s present in the compound, it is preferable that one or two thereof are an alkyl group, an aryl group, or a halogen atom, it is more preferable that one thereof is an alkyl group, an aryl group, or a halogen atom, and it is particularly preferable that one thereof is an alkyl group and the rest are hydrogen atoms.

In Formulae (1) to (4) above, the alkyl group and the aryl group denoted by $R^2$ optionally have a substituent.

Examples of the substituent that the alkyl group and the aryl group denoted by $R^2$ may have include the same substituents as those that the alkyl group and the aryl group denoted by $R^1$ may have.

The alkyl group denoted by $R^2$ is preferably an optionally substituted alkyl group having 1 to 12 carbons in total, and more preferably an optionally substituted alkyl group having 1 to 6 carbons in total.

Specific examples of the alkyl group denoted by $R^2$ include a methyl group, an ethyl group, an n-propyl group, an i-propyl group, an n-butyl group, an i-butyl group, an s-butyl group, a t-butyl group, an allyl group, an n-pentyl group, an n-hexyl group, an n-octyl group, an n-decyl group, an n-dodecyl group, a perfluorohexyl group, a chloromethyl group, a bromomethyl group, a methoxymethyl group, a benzyl group, a phenoxyethyl group, a methylthioethyl group, a phenylthioethyl group, an ethoxycarbonylethyl group, a phenoxycarbonylethyl group, and a dimethylaminocarbonylethyl group.

Among them, a methyl group, an ethyl group, an n-propyl group, an i-propyl group, an n-butyl group, an i-butyl group, an s-butyl group, an n-hexyl group, an allyl group, a chloromethyl group, a bromomethyl group, a methoxymethyl group, and a benzyl group are preferable, a methyl group, an ethyl group, an n-propyl group, an i-propyl group, an n-butyl group, an i-butyl group, an s-butyl group, and an n-hexyl group are more preferable, a methyl group, an ethyl group, an n-propyl group, an n-butyl group, and an n-hexyl group are yet more preferable, and a methyl group is particularly preferable.

The aryl group denoted by $R^2$ is preferably an optionally substituted aryl group having 6 to 30 carbons in total.

Specific examples of the aryl group denoted by $R^2$ include a phenyl group, a p-methylphenyl group, an o-chlorophenyl group, a p-chlorophenyl group, an o-methoxyphenyl group, a p-phenoxyphenyl group, a p-methylthiophenyl group, a p-phenylthiophenyl group, a p-ethoxycarbonylphenyl group, a p-phenoxycarbonylphenyl group, and a p-dimethylaminocarbonylphenyl group.

Among them, a phenyl group, a p-methylphenyl group, an o-chlorophenyl group, a p-chlorophenyl group, an o-methoxyphenyl group, and a p-phenoxyphenyl group are preferable.

Examples of the halogen atom denoted by $R^2$ include a fluorine atom, a chlorine atom, a bromine atom, and an iodine atom.

Among them, a chlorine atom and a bromine atom are preferable.

In Formula (1) above, $Ar^1$ denotes an o-arylene group or an o-heteroarylene group. The o-arylene group and o-heteroarylene group denoted by $Ar^1$ optionally have a substituent.

Examples of the substituent include a halogen atom, an alkyl group, and an alkyloxy group, and they optionally further have a substituent. Preferred examples of the substituent that the o-arylene group and the o-heteroarylene group may have include $R^2$, which is described later.

Specific examples of the o-arylene group and o-heteroarylene group denoted by $Ar^1$ include a 1,2-phenylene group, a 1,2-naphthalenediyl group, a 2,3-naphthalenediyl group, a 2,3-furandiyl group, a 2,3-thiophenediyl group, a 2,3-quinolinediyl group, a 6,7-quinolinediyl group, and a 7,8-quinolinediyl group, these groups optionally having a substituent.

Among them, $Ar^1$ is preferably an o-arylene group, more preferably a 1,2-phenylene group or a 1,2-naphthalenediyl group, and particularly preferably a 1,2-naphthalenediyl group.

In Formulae (1) to (4) above, X denotes O or S.

In Formula (1), X, $Ar^1$, the carbon atom of the oxime group, and $-(CR_2)_n-$ are bonded to form a 5-membered ring or a 6-membered ring.

Furthermore, similarly, in Formulae (2) to (4), the ring containing X as a ring member is a 5-membered ring or a 6-membered ring.

In Formulae (1) to (4) above, n denotes 1 or 2; when X is O, n is preferably 1, and when X is S, n is preferably 2.

In Formulae (2) to (4) above, the alkyl group and alkyloxy group denoted by $R^6$ optionally have a substituent.

In Formulae (2) to (4) above, the alkyl group denoted by $R^6$ is preferably an optionally substituted alkyl group having 1 to 30 carbons in total.

Examples of the substituent that the alkyl group denoted by $R^6$ may have include a halogen atom, an alkyloxy group, an aryloxy group, an alkylthio group, an arylthio group, an alkyloxycarbonyl group, an aryloxycarbonyl group, and an aminocarbonyl group.

Examples of the alkyl group denoted by $R^6$ include a methyl group, an ethyl group, an n-propyl group, an i-propyl group, an n-butyl group, an s-butyl group, a t-butyl group, an n-pentyl group, an n-hexyl group, an n-octyl group, an n-decyl group, an n-dodecyl group, a trifluoromethyl group, a perfluoropropyl group, a perfluorohexyl group, a benzyl group, a phenoxyethyl group, a methylthioethyl group, a phenylthioethyl group, an ethoxycarbonylethyl group, a phenoxycarbonylethyl group, and a dimethylaminocarbonylethyl group.

Among them, a methyl group, an ethyl group, an n-propyl group, an i-propyl group, an n-butyl group, an s-butyl group, a t-butyl group, an n-pentyl group, an n-hexyl group, an n-octyl group, an n-decyl group, an n-dodecyl group, a trifluoromethyl group, a perfluoropropyl group, a perfluorohexyl group, and a benzyl group are preferable.

In Formulae (2) to (4) above, the alkyloxy group denoted by $R^6$ is preferably an optionally substituted alkyloxy group having 1 to 30 carbons in total.

Examples of the substituent that the alkyloxy group denoted by $R^6$ may have include a halogen atom, an alkyloxy group, an aryloxy group, an alkylthio group, an arylthio group, an alkyloxycarbonyl group, an aryloxycarbonyl group, and an aminocarbonyl group.

Examples of the alkyloxy group denoted by $R^6$ include a methyloxy group, an ethyloxy group, a butyloxy group, a hexyloxy group, a phenoxyethyloxy group, a trichloromethyloxy group, an ethoxyethyloxy group, a methylthioethyloxy group, a phenylthioethyloxy group, an ethoxycarbonylethyloxy group, a phenoxycarbonylethyloxy group, and a dimethylaminocarbonylethyloxy group.

Among them, a methyloxy group, an ethyloxy group, a butyloxy group, a hexyloxy group, a phenoxyethyloxy group, a trichloromethyloxy group, and an ethoxyethyloxy group are preferable.

In Formulae (2) to (4) above, examples of the aminosulfonyl group denoted by $R^6$ include a methylaminosulfonyl group, a dimethylaminosulfonyl group, a phenylaminosulfonyl group, a methylphenylaminosulfonyl group, and an aminosulfonyl group.

In Formulae (2) to (4) above, examples of the alkoxysulfonyl group denoted by $R^6$ include a methoxysulfonyl group, an ethoxysulfonyl group, a propyloxysulfonyl group, and a butyloxysulfonyl group.

Furthermore, in Formulae (2) to (4) above, m denotes an integer of 0 to 6, preferably an integer of 0 to 2, more preferably 0 or 1, and particularly preferably 0.

Furthermore, the oxime sulfonate compound represented by Formula (2), Formula (3), or Formula (4) above is more preferably an oxime sulfonate compound represented by any one of Formula (5) to (10) below.

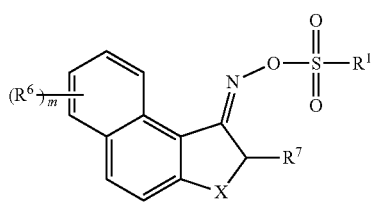
(5)

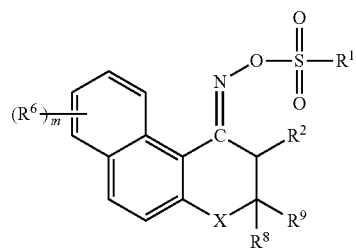
(6)

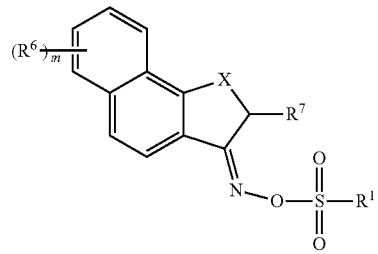
(7)

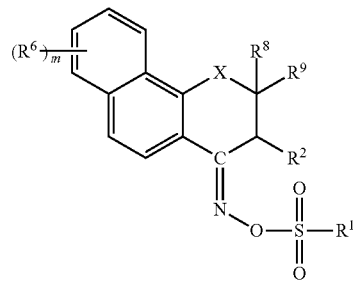
(8)

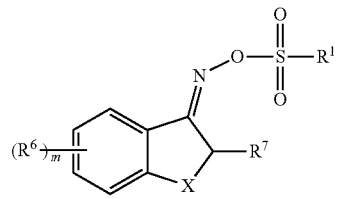
(9)

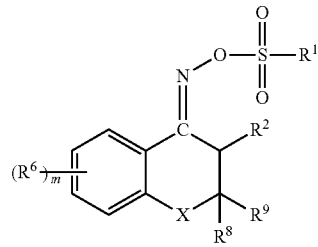
(10)

(In Formulae (5) to (10), $R^1$ denotes an alkyl group, an aryl group, or a heteroaryl group, $R^2$ denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, $R^7$ denotes an alkyl group, an aryl group, or a halogen atom, $R^8$ denotes a hydrogen atom or a methyl group, $R^9$ denotes a hydrogen atom, an alkyl group, or an aryl group, X denotes O or S, and m denotes an integer of 0 to 6. Here, in Formula (6), Formula (8), and Formula (10), not all of $R^2$, $R^8$, and $R^9$ are hydrogen atoms.)

$R^1$, $R^2$, $R^6$, X, and m in Formulae (5) to (10) have the same meanings as $R^1$, $R^2$, $R^6$, X, and m in Formulae (1) to (4) above, and preferred embodiments are also the same.

$R^7$ in Formulae (5), (7), and (9) denotes an alkyl group, an aryl group, or a halogen atom; an alkyl group or an aryl group is preferable, and an alkyl group is more preferable.

$R^8$ in Formulae (6), (8) and (10) denotes a hydrogen atom or a methyl group, and is preferably a hydrogen atom.

$R^9$ in Formulae (6), (8) and (10) denotes a hydrogen atom, an alkyl group, or an aryl group, and is preferably a hydrogen atom or an alkyl group.

In Formula (6), Formula (8), and Formula (10), not all of $R^2$, $R^8$, and $R^9$ are hydrogen atoms, and it is particularly preferable that two of $R^2$, $R^8$, and $R^9$ are hydrogen atoms.

Furthermore, the oxime sulfonate compound represented by Formula (2), Formula (3), or Formula (4) above is yet more preferably an oxime sulfonate compound represented by any of Formulae (11) to (16) below.

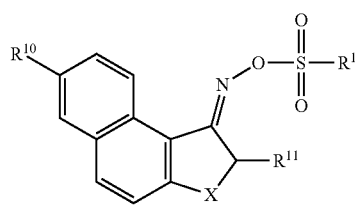
(11)

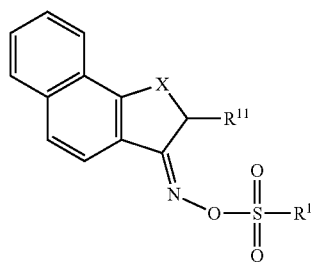
(12)

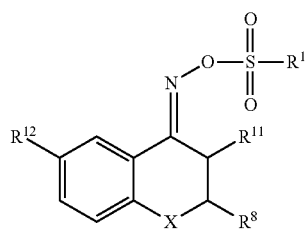
(13)

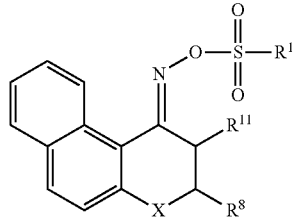
(14)

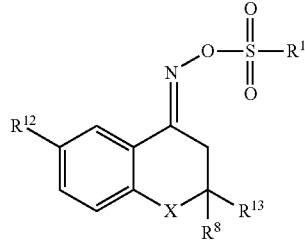
(15)

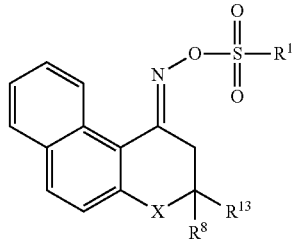
(16)

(In Formulae (11) to (16), $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, $R^{13}$ denotes an unsubstituted alkyl group having 1 to 8 carbons, a chloromethyl group, a bromomethyl group, a bromoethyl group, a methoxymethyl group, a phenyl group, or a chlorophenyl group, and X denotes O or S.)

$R^1$ and X in Formulae (11) to (16) have the same meanings as $R^1$ and X in Formulae (1) to (4) above, and preferred embodiments are also the same.

$R^8$ in Formulae (13) to (16) has the same meaning as $R^8$ in Formulae (6), (8) and (10) above, and preferred embodiments are also the same.

$R^{10}$ in Formula (11) denotes a hydrogen atom or a bromine atom and is preferably a hydrogen atom.

$R^{11}$ in Formulae (11) to (14) denotes an unsubstituted alkyl group having 1 to 8 carbons, a halogen atom, a chloromethyl group, a bromomethyl group, a bromoethyl group, a methoxymethyl group, a phenyl group, or a chlorophenyl group, and is preferably an unsubstituted alkyl group having 1 to 8 carbons, a halogen atom, or a phenyl group, more preferably an unsubstituted alkyl group having 1 to 8 carbons, yet more preferably an unsubstituted alkyl group having 1 to 6 carbons, and particularly preferably a methyl group.

$R^{12}$ in Formula (13) and Formula (15) denotes a hydrogen atom, a halogen atom, a methyl group, or a methoxy group, and is preferably a hydrogen atom.

$R^{13}$ in Formula (15) and Formula (16) denotes an unsubstituted alkyl group having 1 to 8 carbons, a chloromethyl group, a bromomethyl group, a bromoethyl group, a methoxymethyl group, a phenyl group, or a chlorophenyl group, and is preferably an unsubstituted alkyl group having 1 to 8 carbons, a halogen atom, or a phenyl group, more preferably an unsubstituted alkyl group having 1 to 8 carbons, yet more preferably an unsubstituted alkyl group having 1 to 6 carbons, and particularly preferably a methyl group.

Furthermore, the oxime sulfonate compound represented by Formula (2), Formula (3), or Formula (4) above is particularly preferably an oxime sulfonate compound represented by any of Formulae (17) to (22) below.

(17)

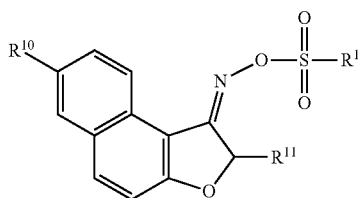

(18)

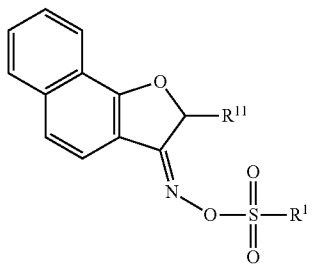

(19)

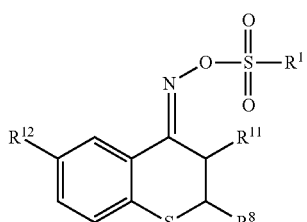

(20)

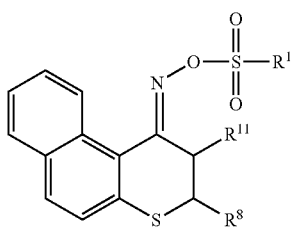

(21)

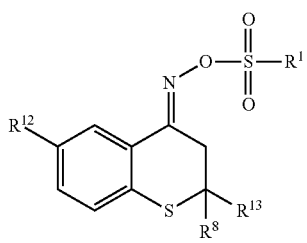

(22)

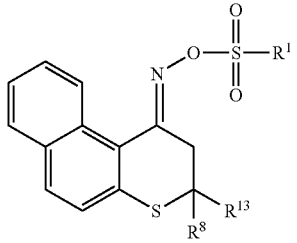

(In Formulae (17) to (22), $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, and $R^{13}$ denotes an unsubstituted alkyl group having 1 to 8 carbons, a chloromethyl group, a bromomethyl group, a bromoethyl group, a methoxymethyl group, a phenyl group, or a chlorophenyl group.)

$R^{10}$ in Formula (17) has the same meaning as $R^{10}$ in Formula (11) above, and preferred embodiments are also the same.

$R^{11}$ in Formulae (17) to (20) has the same meaning as $R^{11}$ in Formulae (11) to (14) above, and preferred embodiments are also the same.

$R^{12}$ in Formula (19) and Formula (21) has the same meaning as $R^{12}$ in Formula (13) and Formula (15) above, and preferred embodiments are also the same.

$R^{13}$ in Formula (21) and Formula (22) has the same meaning as $R^{13}$ in Formula (15) and Formula (16) above, and preferred embodiments are also the same.

Furthermore, with regard to the oxime sulfonate compound, the oxime may have either conformation (E, Z), or it may be a mixture thereof.

Specific examples of the oxime sulfonate compound represented by Formula (1) above include the compound examples below, but the present invention is not limited thereby.

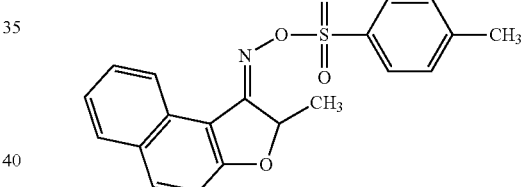

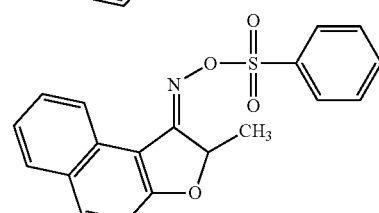

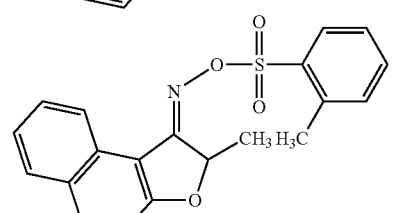

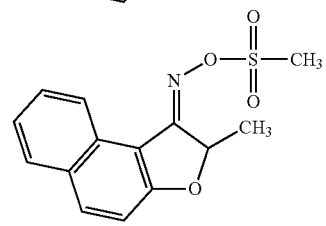

71
-continued
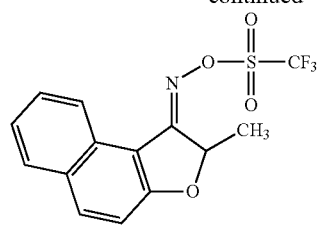
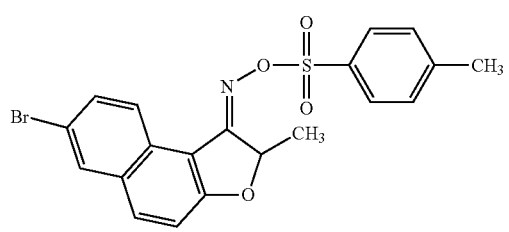
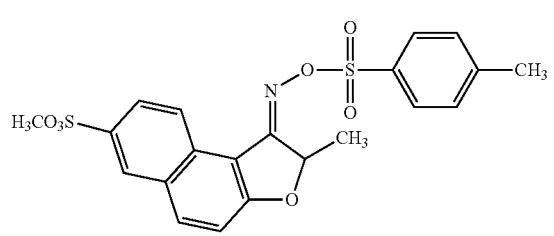
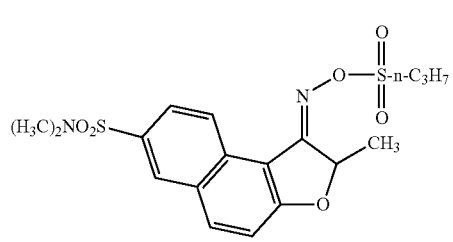
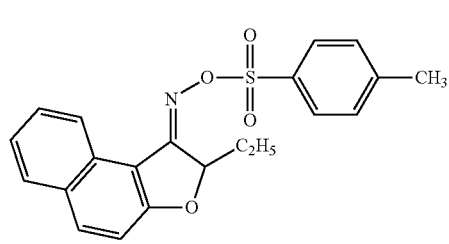
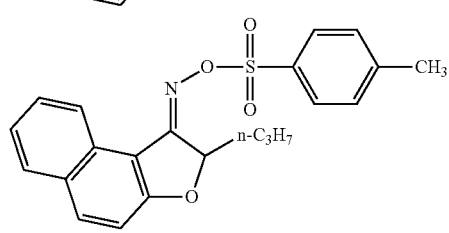
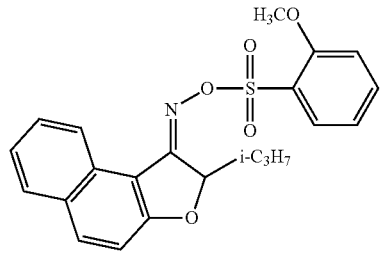
72
-continued
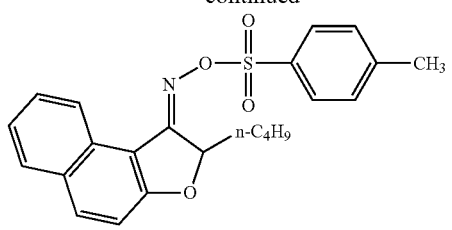
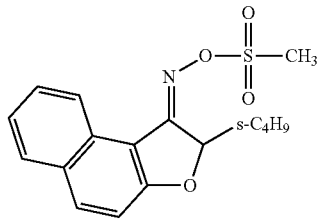
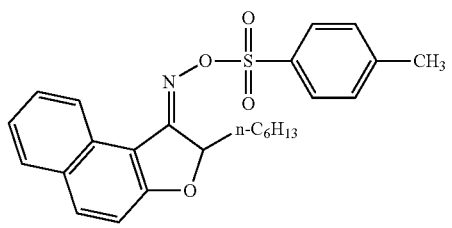
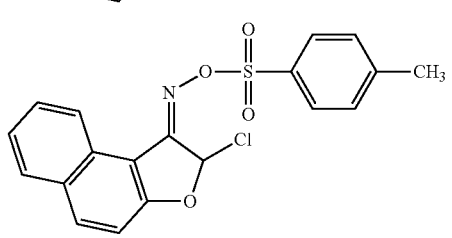
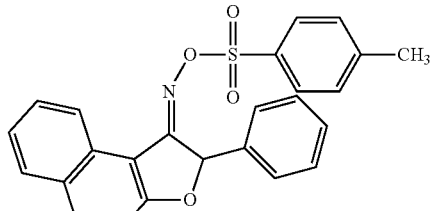
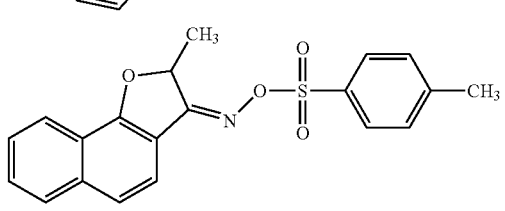
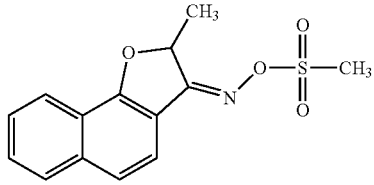
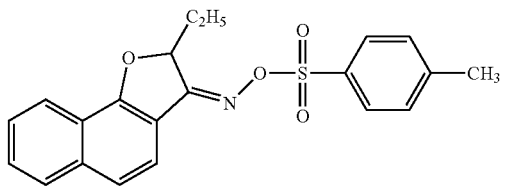

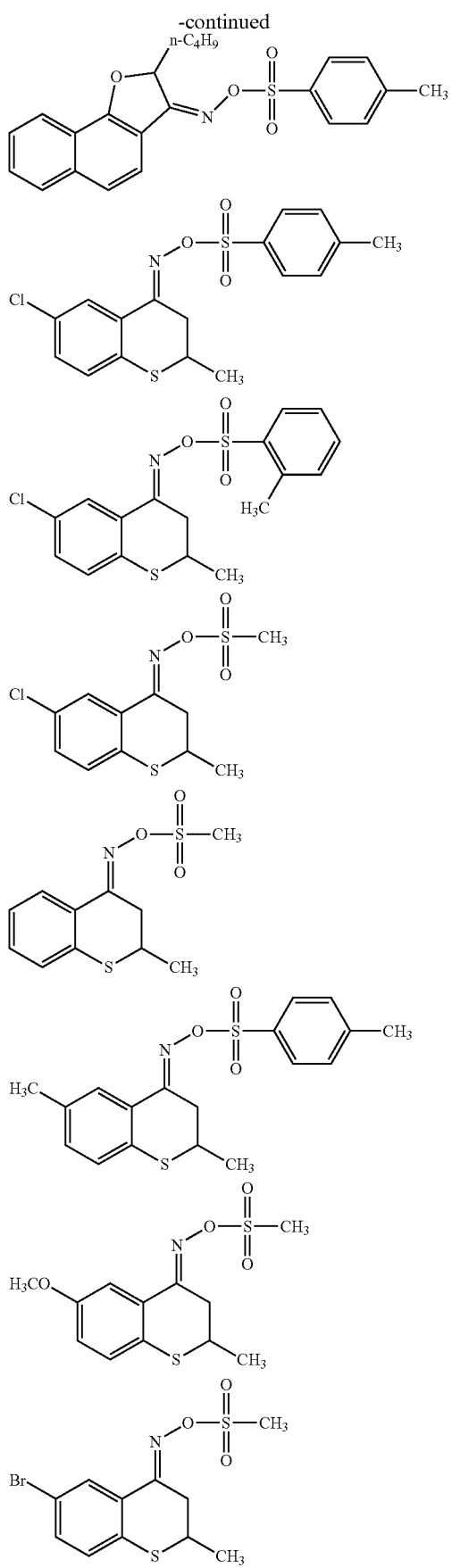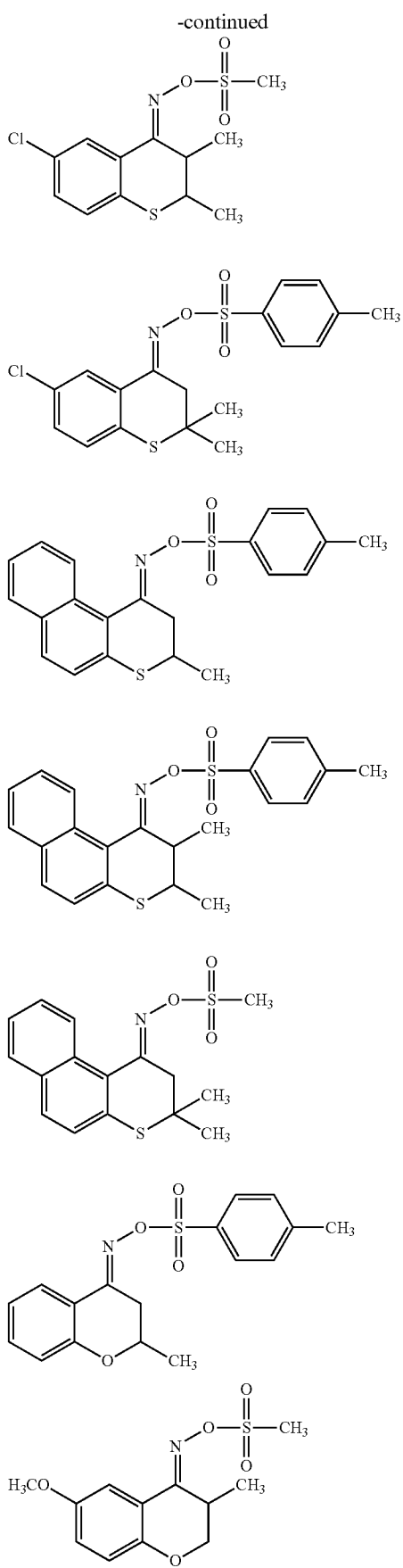

-continued

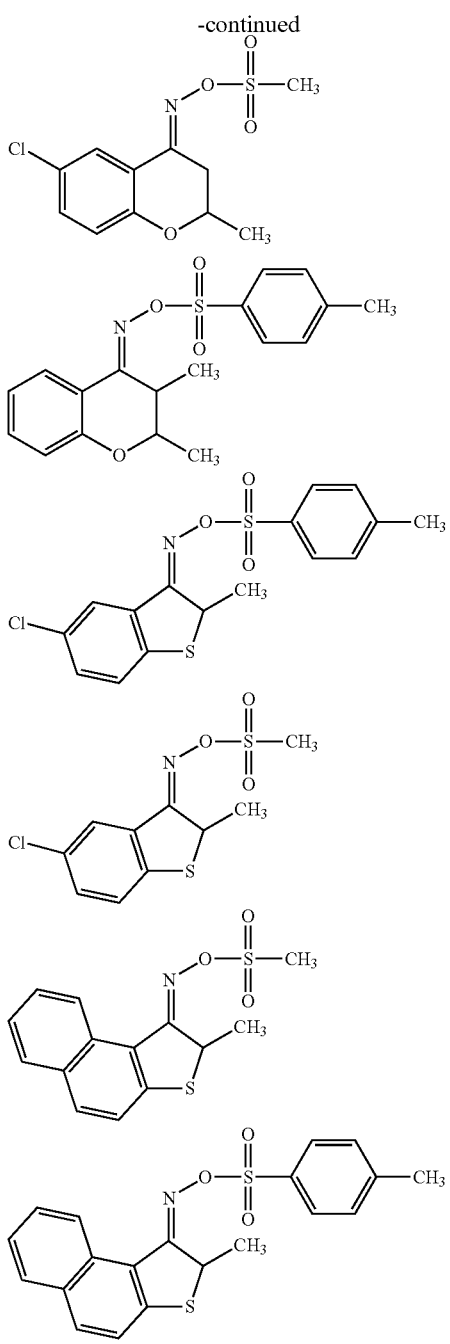

In accordance with the present invention, there can be provided a photosensitive resin composition having high sensitivity and wide development latitude and giving a cured film having excellent transparency, and a method for forming a cured film employing same. Furthermore, in accordance with the present invention there can be provided a photosensitive resin composition having excellent storage stability, and a method for forming a cured film employing same.

Moreover, in accordance with the present invention there can be provided an oxime sulfonate compound having high sensitivity and wide development latitude and giving a cured film, formed by polymerization of a polymerizable compound, having excellent transparency, and having excellent storage stability even when it is mixed with another component to form a composition.

EXAMPLES

Examples of the present embodiment are explained below in detail, but the present embodiment is not limited by these Examples. 'Parts' in the description below means 'parts by weight' unless otherwise specified.
(Synthesis of Oxime Sulfonate Compound)
<Synthesis of A-1>

Aluminum chloride (10.6 g) and 2-chloropropionyl chloride (10.1 g) were added to a suspension of 2-naphthol (10 g) in chlorobenzene (30 mL), and a reaction was carried out by heating the liquid mixture at 40° C. for 2 hours. A 4N HCl aqueous solution (60 mL) was added dropwise to the reaction mixture under ice cooling, ethyl acetate (50 mL) was added thereto, and a separation was carried out. Potassium carbonate (19.2 g) was added to the organic layer, and a reaction was carried out at 40° C. for 1 hour; a 2N HCl aqueous solution (60 mL) was then added, a separation was carried out, the organic layer was concentrated, and crystals were then reslurried using diisopropyl ether (10 mL), filtered, and dried, thus giving a ketone compound (6.5 g).

Acetic acid (7.3 g) and a 50 wt % hydroxylamine aqueous solution (8.0 g) were added to a suspension of the ketone compound (3.0 g) thus obtained in methanol (18 mL), and the mixture was refluxed by heating for 10 hours. After leaving to cool, water (50 mL) was added, and the crystals thus precipitated were filtered, washed with cold methanol, and then dried, thus giving an oxime compound (2.4 g).

The oxime compound (1.8 g) thus obtained was dissolved in acetone (20 mL), triethylamine (1.5 g) and p-toluenesulfonyl chloride (2.4 g) were added under ice cooling, the temperature of the mixture was increased to room temperature, and a reaction was carried out for 1 hour. Water (50 mL) was added to the reaction mixture, the crystals thus precipitated were filtered, and they were then reslurried with methanol (20 mL), filtered, and dried, thus giving A-1 (2.3 g).

$^1$H-NMR spectrum (300 MHz, CDCl$_3$) of A-1: δ=8.3 (d, 1H), 8.0 (d, 2H), 7.9 (d, 1H), 7.8 (d, 1H), 7.6 (dd, 1H), 7.4 (dd, 1H), 7.3 (d, 2H), 7.1 (d, 1H), 5.6 (q, 1H), 2.4 (s, 3H), 1.7 (d, 3H).
<Synthesis of A-2>

Crotonic acid (59.3 g) was added a suspension of 4-chlorobenzenethiol (100 g) in chlorobenzene (100 mL), triethylamine (28.9 mL) was added dropwise thereto, and a reaction was carried out at 80° C. for 6 hours. After cooling to 50° C., N,N-dimethylacetamide (0.1 mL) was added to the reaction mixture, thionyl chloride (50.2 mL) was added dropwise thereto, and a reaction was carried out for 1 hour. The reaction mixture was added dropwise under ice cooling to a suspension of aluminum chloride (96.8 g) in chlorobenzene (200 mL) that had been prepared in advance, and a reaction was carried out at less than 8° C. for 4 hours. The reaction mixture was poured into 1,000 g of ice, and the organic layer was separated, then washed with 500 mL of water, and concentrated, thus giving crude crystals. The crude crystals were recrystallized from methanol (150 mL), filtered, and washed with cold methanol, thus giving a ketone compound (105 g).

The ketone compound (2.1 g) thus obtained was dissolved in ethanol (35 mL), acetic acid (0.9 g) and a 50 wt % hydroxylamine aqueous solution (1.0 g) were added, and the mixture was refluxed under heating After leaving to cool, water (50 mL) was added, and the crystals thus precipitated were filtered and dried, thus giving an oxime compound (1.9 g).

The oxime compound (1.7 g) thus obtained was dissolved in acetone (20 mL), triethylamine (1.1 g) and p-toluenesulfonyl chloride (1.7 g) were added under ice cooling, the temperature of the mixture was increased to room temperature, and a reaction was carried out for 1 hour. Water (50 mL) was added to the reaction mixture, and the crystals thus precipitated were filtered, then reslurried with cold methanol (20 mL), filtered, and dried, thus giving A-2 (2.5 g).

$^1$H-NMR spectrum (300 MHz, CDCl$_3$) of A-2: δ=7.9 (d, 2H), 7.8 (s, 1H), 7.4 (d, 2H), 7.2 (d, 1H), 7.1 (d, 1H), 3.4 (dd, 1H), 3.3 (qdd, 1H), 2.6 (dd, 1H), 2.4 (s, 3H), 1.4 (d, 3H).

<Synthesis of A-3>

A-3 was synthesized in the same manner as for A-2 except that o-toluenesulfonyl chloride was used instead of the p-toluenesulfonyl chloride in A-2.

$^1$H-NMR spectrum (300 MHz, CDCl$_3$) of A-3: δ=8.1 (d, 1H), 7.7 (s, 1H), 7.6 (dd, 1H), 7.4 (dd, 1H), 7.3 (d, 1H), 7.2 (d, 1H), 7.1 (d, 1H), 3.4 (dd, 1H), 3.3 (qdd, 1H), 2.7 (dd, 1H), 2.7 (s, 3H), 1.4 (d, 3H).

<Synthesis of A-4>

A-4 was synthesized in the same manner as for A-2 except that methanesulfonyl chloride was used instead of the p-toluenesulfonyl chloride in A-2.

$^1$H-NMR spectrum (300 MHz, CDCl$_3$) of A-3: δ=8.0 (s, 1H), 7.3 (d, 1H), 7.2 (d, 1H), 3.4 (dd, 1H), 3.3 (qdd, 1H), 3.2 (s, 3H), 2.8 (dd, 1H), 1.4 (d, 3H).

<Synthesis of A-3>

A-3 was synthesized in the same manner as for A-2 except that 2-naphthalenethiol was used instead of the 4-chlorobenzenethiol in A-2.

$^1$H-NMR spectrum (300 MHz, CDCl$_3$) of A-5: δ=8.3 (d, 1H), 7.9 (d, 1H), 7.7 (d, 1H), 7.6 (d, 1H), 7.4 (dd, 1H), 7.4 to 7.3 (m, 3H), 7.2 (d, 1H), 3.4 (dd, 1H), 3.3 (qdd, 1H), 3.1 (dd, 1H), 2.4 (s, 3H), 1.4 (d, 3H).

<Synthesis of A-6>

2-Naphthol (20 g) was dissolved in N,N-dimethylacetamide (150 mL), potassium carbonate (28.7 g) and ethyl 2-bromooctanoate (52.2 g) were added thereto, and a reaction was carried out at 100° C. for 2 hours. Water (300 mL) and ethyl acetate (200 mL) were added to the reaction mixture, a separation was carried out, and the organic layer was concentrated; following this a 48 wt % sodium hydroxide aqueous solution (23 g), ethanol (50 mL), and water (50 mL) were added, and a reaction was carried out for 2 hours. The reaction mixture was poured into a 1N HCl aqueous solution (500 mL), and the crystals thus precipitated were filtered and washed with water, thus giving a crude carboxylic acid; following this, polyphosphoric acid (30 g) was added, and a reaction was carried out at 170° C. for 30 min. The reaction mixture was poured into water (300 mL), ethyl acetate (300 mL) was added, a separation was carried out, and the organic layer was concentrated and then purified by means of silica gel column chromatography, thus giving a ketone compound (10 g).

Sodium acetate (30.6 g), hydroxylamine hydrochloride (25.9 g), and magnesium sulfate (4.5 g) were added to a suspension of the ketone compound (10.0 g) thus obtained in methanol (100 mL), and the mixture was refluxed under heating for 24 hours. After leaving to cool, water (150 mL) and ethyl acetate (150 mL) were added, a separation was carried out, and the organic layer was separated four times with 80 mL of water, concentrated, and then purified by means of silica gel column chromatography, thus giving an oxime compound (5.8 g).

The oxime compound (3.1 g) thus obtained was subjected to sulfonation in the same manner as for A-1, thus giving A-6 (3.2 g).

$^1$H-NMR spectrum (300 MHz, CDCl$_3$) of A-6: δ=8.3 (d, 1H), 8.0 (d, 2H), 7.9 (d, 1H), 7.8 (d, 1H), 7.6 (dd, 1H), 7.5 (dd, 1H), 7.3 (d, 2H), 7.1 (d, 1H), 5.6 (dd, 1H), 2.4 (s, 3H), 2.2 (ddt, 1H), 1.9 (ddt, 1H), 1.4 to 1.2 (m, 8H), 0.8 (t, 3H).

<Synthesis of A-7>

A-7 was synthesized in the same manner as for A-1 except that benzenesulfonyl chloride was used instead of the p-toluenesulfonyl chloride in A-1.

$^1$H-NMR spectrum (300 MHz, CDCl$_3$) of A-7: δ=8.3 (d, 1H), 8.1 (d, 2H), 7.9 (d, 1H), 7.8 (d, 1H), 7.7 to 7.5 (m, 4H), 7.4 (dd, 1H), 7.1 (d, 1H), 5.6 (q, 1H), 1.7 (d, 3H).

<Synthesis of A-8>

A-8 was synthesized in the same manner as for A-1 except that 2,4,6-trimethylphenylsulfonyl chloride was used instead of the p-toluenesulfonyl chloride in A-1.

$^1$H-NMR spectrum (300 MHz, CDCl$_3$) of A-8: δ=8.3 (d, 1H), 7.9 (d, 1H), 7.8 (d, 1H), 7.5 (dd, 1H), 7.4 (dd, 1H), 7.1 (d, 2H), 7.0 (s, 2H), 5.6 (q, 1H), 3.3 (s, 6H), 2.3 (s, 3H), 1.7 (d, 3H).

<Synthesis of A-9>

A-9 was synthesized in the same manner as for A-1 except that 2,4,6-triisopropylphenylsulfonyl chloride was used instead of the p-toluenesulfonyl chloride in A-1.

$^1$H-NMR spectrum (300 MHz, CDCl$_3$) of A-9: δ=8.3 (d, 1H), 7.9 (d, 1H), 7.8 (d, 1H), 7.5 (dd, 1H), 7.4 (dd, 1H), 7.3 (s, 2H), 7.1 (d, 1H), 5.6 (q, 1H), 4.3 (qq, 2H), 2.9 (qq, 1H), 1.7 (d, 3H), 1.4 to 1.3 (m, 12H), 1.3 to 1.2 (m, 6H).

<Synthesis of A-10>

A-10 was synthesized in the same manner as for A-1 except that methanesulfonyl chloride was used instead of the p-toluenesulfonyl chloride in A-1.

$^1$H-NMR spectrum (300 MHz, CDCl$_3$) of A-10: δ=8.4 (d, 1H), 8.0 (d, 1H), 7.8 (dd, 1H), 7.6 (dd, 1H), 7.5 (dd, 1H), 7.2 (d, 1H), 5.6 (q, 1H), 3.3 (s, 3H), 1.7 (d, 3H).

<Synthesis of A-11>

A-11 was synthesized in the same manner as for A-1 except that n-butanesulfonyl chloride was used instead of the p-toluenesulfonyl chloride in A-1.

$^1$H-NMR spectrum (300 MHz, CDCl$_3$) of A-11: δ=8.4 (d, 1H), 8.0 (d, 1H), 7.8 (d, 1H), 7.7 (dd, 1H), 7.5 (dd, 1H), 7.2 (d, 1H), 5.6 (q, 1H), 3.5 (t, 2H), 1.9 (tt, 2H), 1.7 (d, 3H), 1.5 (qt, 2H), 1.0 (t, 3H).

<Synthesis of A-12>

A-12 was synthesized in the same manner as for A-1 except that n-octanesulfonyl chloride was used instead of the p-toluenesulfonyl chloride in A-1.

$^1$H-NMR spectrum (300 MHz, CDCl$_3$) of A-12: δ=8.4 (d, 1H), 8.0 (d, 1H), 7.8 (d, 1H), 7.7 (dd, 1H), 7.5 (dd, 1H), 7.2 (d, 1H), 5.6 (q, 1H), 3.5 (t, 2H), 1.9 (tt, 2H), 1.7 (d, 3H), 1.5 (qt, 2H), 1.4 to 1.2 (m, 8H), 0.8 (t, 3H).

<Synthesis of A-13>

A-13 was synthesized in the same manner as for A-1 except that p-chlorobenzenesulfonyl chloride was used instead of the p-toluenesulfonyl chloride in A-1.

$^1$H-NMR spectrum (300 MHz, CDCl$_3$) of A-13: δ=8.3 (d, 1H), 8.1 (d, 2H), 7.9 (d, 1H), 7.8 (d, 1H), 7.7 (dd, 1H), 7.6 (d, 2H), 7.5 (dd, 1H), 7.1 (d, 1H), 5.6 (q, 1H), 1.7 (d, 3H).

<Synthesis of A-14>

A-14 was synthesized in the same manner as for A-1 except that pentafluorobenzenesulfonyl chloride was used instead of the p-toluenesulfonyl chloride in A-1.

$^1$H-NMR spectrum (300 MHz, CDCl$_3$) of A-14: δ=8.2 (d, 1H), 8.0 (d, 1H), 7.8 (d, 1H), 7.6 (dd, 1H), 7.4 (dd, 1H), 7.2 (d, 1H), 5.6 (q, 1H), 1.7 (d, 3H).

<Synthesis of A-15>

A-15 was synthesized in the same manner as for A-1 except that 6-methoxy-2-naphthol was used instead of the 2-naphthol in A-1.

¹H-NMR spectrum (300 MHz, CDCl₃) of A-15: δ=8.3 (d, 1H), 8.0 (d, 2H), 7.8 (d, 1H), 7.4 (d, 2H), 7.3 (d, 1H), 7.1 (d, 1H), 7.0 (d, 1H), 5.6 (q, 1H), 3.9 (s, 3H), 2.4 (s, 3H), 1.7 (d, 3H).

<Synthesis of A-16>

A-16 was synthesized in the same manner as for A-2 except that 2-naphthalenethiol and methacrylic acid were used instead of the 4-chlorobenzenethiol and crotonic acid respectively in A-2.

¹H-NMR spectrum (300 MHz, CDCl₃) of A-16: δ=8.1 (d, 1H), 7.9 (d, 2H), 7.7 (d, 1H), 7.7 (d, 1H), 7.4 (dd, 1H), 7.3 to 7.2 (m, 4H), 4.1 (qdd, 1H), 3.2 (dd, 1H), 2.7 (dd, 1H), 2.4 (s, 3H), 1.3 (d, 3H).

<Synthesis of A-17>

4-Methoxy-1-naphthol (12.5 g) was dissolved in 1-methyl-2-pyrrolidone (40 mL), potassium carbonate (11.9 g) and ethyl 2-bromopropanoate (15.6 g) were added thereto, and a reaction was carried out at 80° C. for 2 hours. A 1N HCl aqueous solution (120 mL) and ethyl acetate (100 mL) were added to the reaction mixture, a separation was carried out, the organic layer was concentrated, ethanol (25 mL), water (25 mL), and sodium hydroxide (5.7 g) were then added, and a reaction was carried out at 60° C. for 1 hour. The reaction mixture was poured into a 1N HCl aqueous solution (300 mL) and extracted with ethyl acetate, and the organic layer was dried with magnesium sulfate, filtered, and concentrated, thus giving a crude carboxylic acid (19 g).

Oxalyl chloride (3.1 g) and one drop of N,N-dimethylacetamide were added to a suspension of the carboxylic acid (5.0 g) thus obtained in chlorobenzene (20 mL) under ice cooling, the temperature of the mixture was increased to room temperature, and stirring was carried out for 1 hour. Aluminum chloride (3.2 g) was added to this reaction mixture under ice cooling, the temperature of the mixture was increased to room temperature, and a reaction was carried out for 1 hour. A 4N HCl aqueous solution (60 mL) was added dropwise to the reaction mixture under ice cooling, subsequently water was added, ethyl acetate (50 mL) was added, and a separation was carried out. The organic layer was washed with saturated brine, concentrated, and then purified by means of silica gel column chromatography, thus giving a ketone compound (2.0 g).

The ketone compound (2.0 g) thus obtained was subjected to oximation and then sulfonation in the same manner as for A-1, thus giving A-17 (0.6 g).

¹H-NMR spectrum (300 MHz, CDCl₃) of A-17: δ=8.2 (d, 1H), 8.1 (d, 1H), 8.0 (d, 2H), 7.7 (dd, 1H), 7.6 (dd, 1H), 7.3 (d, 2H), 6.7 (s, 1H), 5.6 (q, 1H), 4.0 (s, 3H), 2.4 (s, 3H), 1.7 (d, 3H).

<Synthesis of A-18>

A-18 was synthesized in the same manner as for A-2 except that methacrylic acid was used instead of the crotonic acid in A-2.

¹H-NMR spectrum (300 MHz, CDCl₃) of A-18: δ=7.9 (d, 2H), 7.8 (s, 1H), 7.4 (d, 2H), 7.2 (d, 1H), 7.1 (d, 1H), 3.8 (qdd, 1H), 3.3 (dd, 1H), 2.7 (dd, 1H), 2.4 (s, 3H), 1.2 (d, 3H).

<Synthesis of A-19>

A-19 was synthesized in the same manner as for A-16 except that o-toluenesulfonyl chloride was used instead of the p-toluenesulfonyl chloride in A-16.

¹H-NMR spectrum (300 MHz, CDCl₃) of A-19: δ=8.1 (d, 2H), 7.8 (d, 1H), 7.7 (d, 2H), 7.6 (dd, 1H), 7.4 (dd, 1H), 7.3 (dd, 1H), 7.2 (d, 2H), 7.1 (dd, 1H), 4.2 (qdd, 1H), 3.7 (dd, 1H), 2.7 (s, 3H), 2.7 (dd, 1H), 1.3 (d, 3H).

<Synthesis of A-20>

A-20 was synthesized in the same manner as for A-6 except that ethyl 2-bromo-3-methylbutanoate was used instead of the 2-bromoactanoate in A-6.

¹H-NMR spectrum (300 MHz, CDCl₃) of A-20: δ=8.3 (d, 1H), 8.0 (d, 2H), 7.9 (d, 1H), 7.8 (d, 1H), 7.6 (dd, 1H), 7.5 (dd, 1H), 7.3 (d, 2H), 7.1 (d, 1H), 5.6 (d, 1H), 2.5 to 2.3 (m, 4H), 1.2 (d, 3H), 0.8 (d, 3H).

<Synthesis of A-21>

A-21 was synthesized in the same manner as for A-1 except that 2,4-bis(trifluoromethyl)benzenesulfonyl chloride was used instead of the p-toluenesulfonyl chloride in A-1.

¹H-NMR spectrum (300 MHz, CDCl₃) of A-21: δ=8.6 (s, 2H), 8.2 (s, 1H), 8.1 (d, 1H), 8.0 (d, 1H), 7.8 (d, 1H), 7.6 (dd, 1H), 7.4 (dd, 1H), 7.2 (d, 1H), 5.6 (q, 1H), 1.7 (d, 3H).

<Synthesis of AX-1>

AX-1 was synthesized by the same method as that described in JP-A-2008-247780.

<Synthesis of AX-2>

AX-2 was synthesized in the same manner as for A-2 except that acrylic acid was used instead of the crotonic acid in A-2.

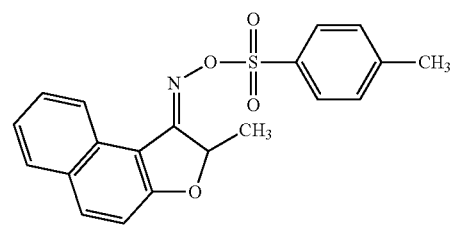

A-1

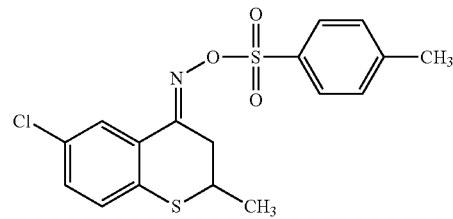

A-2

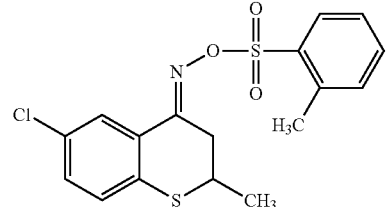

A-3

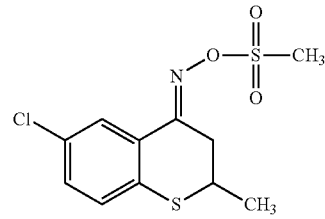

A-4

A-5
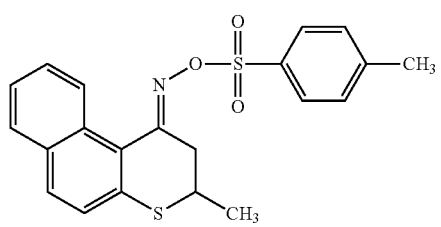
A-6
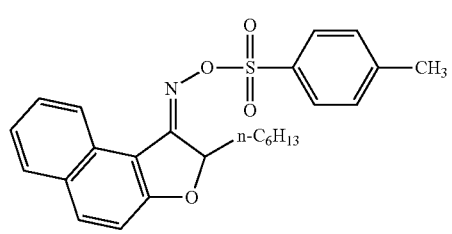
A-7
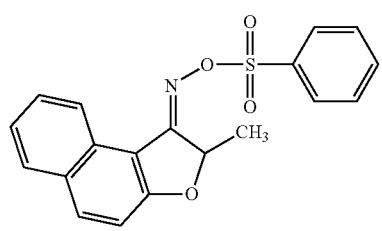
A-8
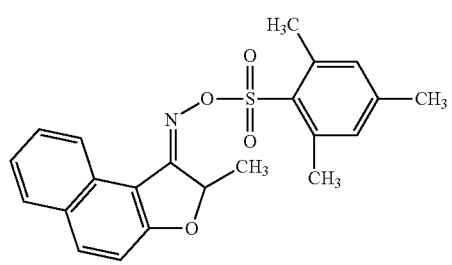
A-9
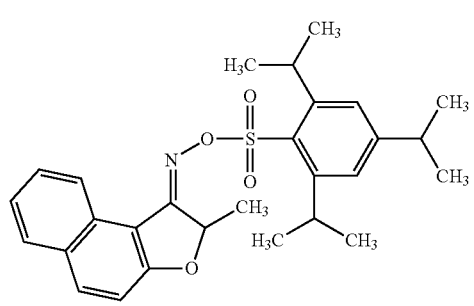
A-10
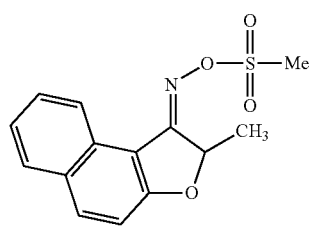
A-11
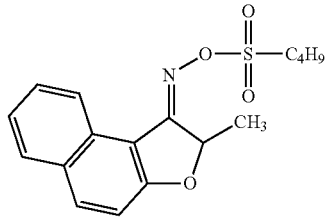
A-12
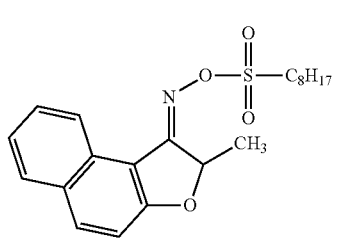
A-13
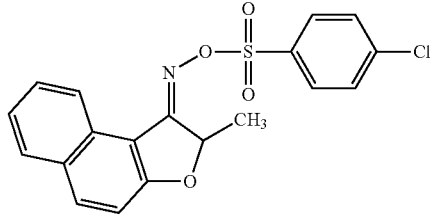
A-14
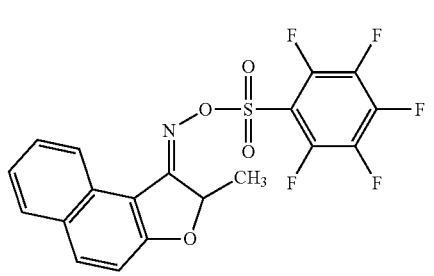
A-15
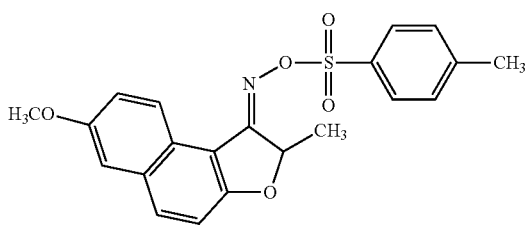
A-16
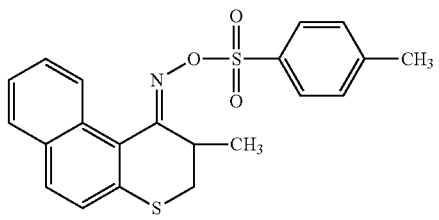

A-17

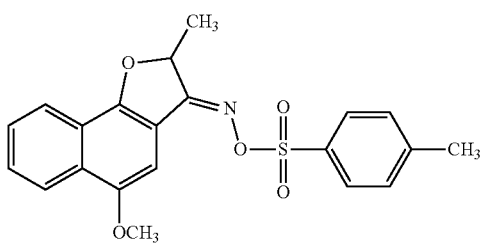

A-18

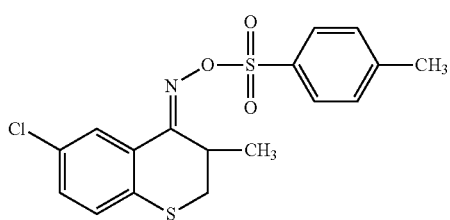

A-19

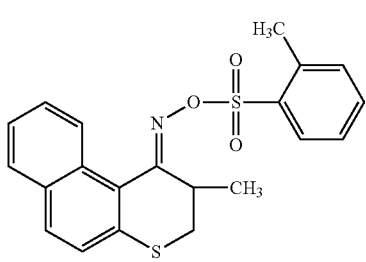

A-20

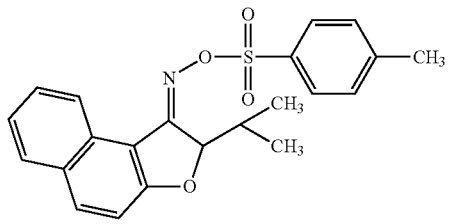

A-21

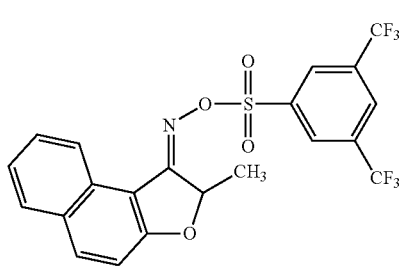

AX-1

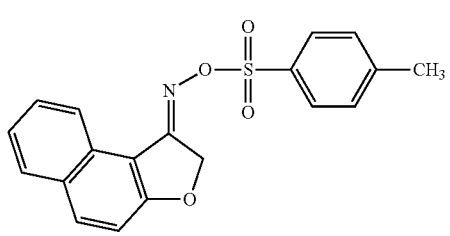

AX-2

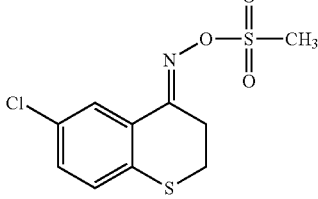

In the Synthetic Examples below, the symbols denote the following compounds.
V-65: 2,2'-azobis(2,4-dimethylvaleronitrile)
AIBN: 2,2'-azobisbutyronitrile
GMA: glycidyl methacrylate
MAA: methacrylic acid
HEMA: 2-hydroxyethyl methacrylate
EDM: diethylene glycol ethyl methyl ether
PGMEA: propylene glycol monomethyl ether acetate
St: styrene
DCPM: dicyclopentanyl methacrylate
OXE-30: (3-ethyloxetan-3-yl)methyl methacrylate (Osaka Organic Chemical Industry Ltd.)
<Synthesis of Copolymer B-1>
Copolymer B-1 was synthesized by the following method.
<Synthesis of 1-Ethoxyethyl Methacrylate (MAEVE)>
0.5 parts of phenothiazine was added to 144.2 parts (2 molar equivalents) of ethyl vinyl ether, 86.1 parts (1 molar equivalent) of methacrylic acid was added dropwise to the reaction system while cooling to 10° C. or below, and stirring was then carried out at room temperature (25° C.) for 4 hours. 5.0 parts of pyridinium p-toluenesulfonate was added thereto, stirring was then carried out at room temperature for 2 hours, and the mixture was allowed to stand at room temperature overnight. 5 parts of sodium bicarbonate and 5 parts of sodium sulfate were added to the reaction mixture, stirring was carried out at room temperature for 1 hour, insoluble material was filtered, concentration under vacuum was then carried out at no greater than 40° C., and a yellow oily residue was distilled under vacuum, thus giving 134.0 parts of 1-ethoxyethyl methacrylate (MAEVE) as a colorless oily material, this being a fraction with a boiling point (bp.) of 43° C. to 45° C./7 mmHg.

A mixed solution of the MAEVE (63.28 parts (0.4 molar equivalents)) thus obtained, OXE-30 (55.27 parts (0.3 molar equivalents)), MAA (8.61 parts (0.1 molar equivalents)), HEMA (26.03 parts (0.2 molar equivalents)), and EDM (110.8 parts) was heated at 70° C. under a flow of nitrogen. While stirring this mixed solution, a mixed solution of V-65 radical polymerization initiator (Wako Pure Chemical Industries, Ltd., 7 parts) and EDM (100.0 parts) was added dropwise thereto over 2.5 hours. After the dropwise addition was completed, a reaction was carried out at 70° C. for 4 hours, thus giving an EDM solution of copolymer B-1 (solids content: 40%).

It was found by means of gel permeation chromatography (GPC) that the weight-average molecular weight (Mw) of the copolymer B-1 thus obtained was 7,000.
<Synthesis of Copolymers B-2 to B-10>
Copolymers B-2 to B-10 were synthesized in the same manner as in the synthesis of copolymer B-1 except that the monomers used and the amounts thereof used were changed as shown in Table 1 below.
The method for the synthesis of tetrahydrofuran-2-yl methacrylate (MATHF) was as follows.

<Synthesis of MATHF>

Methacrylic acid (86 g, 1 mol) was cooled to 15° C., and camphorsulfonic acid (4.6 g, 0.02 mol) was added thereto. 2-Dihydrofuran (71 g, 1 mol, 1.0 equivalents) was added dropwise to this solution. After stirring for 1 hour, saturated sodium bicarbonate (500 mL) was added, and the mixture was extracted with ethyl acetate (500 mL) and dried with magnesium sulfate; following this insoluble material was filtered, concentration under vacuum was then carried out at no greater than 40° C., and a yellow oily residue was distilled under vacuum, thus giving 125 g of tetrahydrofuran-2-yl methacrylate (MATHF) (yield 80%) as a colorless oily material, this being a fraction with a boiling point (bp.) of 54° C. to 56° C./3.5 mmHg.

<Synthesis of Copolymer B"-1>

A solution of AIBN (9.0 parts) in EDM (459.0 parts) was mixed with St (22.50 parts (0.22 molar equivalents)), MAA (44.50 parts (0.52 molar equivalents)), DCPM (56.25 parts (0.26 molar equivalents)), and GMA (90 parts (0.63 molar equivalents)) under a flow of nitrogen while stirring, the temperature was increased to 80° C., and a reaction was carried out for 5 hours, thus giving an EDM solution of copolymer B"-1 (solids content: 32%).

<Synthesis of Copolymer B"-2>

Copolymer B"-2 was synthesized in the same manner as for copolymer B"-1 except that OXE-30 was used instead of the GMA used for copolymer B"-1.

PHStBOC was obtained by reacting 4-hydroxystyrene and t-butoxycarboxylic acid anhydride under basic conditions, extracting, and then purifying by means of silica gel chromatography.

Example 1-1

Components were dissolved and mixed so as to give the composition below, and filtered using a polytetrafluoroethylene filter having a pore size of 0.2 μm, thus giving a photosensitive resin composition of Example 1-1.

| | |
|---|---|
| Oxime sulfonate compound: A-1 | 2.0 parts |
| Component B: polyethylene glycol methyl ether acetate (hereinafter, abbreviated to PGMEA) solution of copolymer B-1 | 100.0 parts as solids content |
| Sensitizer: D-1 shown below | 2.0 parts |
| Adhesion improving agent: E-1 shown below | 0.5 parts |
| Surfactant: F-1 shown below | 0.02 parts |
| Crosslinking agent: G-1 shown below | 5.0 parts |
| Basic compound: I-1 shown below | 0.01 parts |
| Basic compound: I-2 shown below | 0.1 parts |

TABLE 1

| Copolymer | Monomer having acid-decomposable group | | Other monomer 1 | | Other monomer 2 | | Other monomer 3 | | Other monomer 4 | | Mw |
|---|---|---|---|---|---|---|---|---|---|---|---|
| | Type | Molar equivalents | Type | Molar equivalents | Type | Molar equivalents | Type | Molar equivalents | Type | Molar equivalents | |
| B-1 | MAEVE | 0.4 | OXE-30 | 0.3 | MMA | 0.1 | HEMA | 0.2 | — | — | 7,000 |
| B-2 | MAEVE | 0.4 | GMA | 0.3 | MAA | 0.1 | HEMA | 0.2 | — | — | 10,000 |
| B-3 | MATHF | 0.4 | OXE-30 | 0.3 | MAA | 0.1 | HEMA | 0.2 | — | — | 17,000 |
| B-4 | MATHF | 0.4 | GMA | 0.3 | MAA | 0.1 | HEMA | 0.2 | — | — | 12,000 |
| B-5 | MATHF | 0.5 | OXE-30 | 0.4 | MAA | 0.1 | — | — | — | — | 13,000 |
| B-6 | MACHVE | 0.4 | GMA | 0.3 | St | 0.1 | CHMI | 0.2 | — | — | 6,000 |
| B-7 | t-BMA | 0.3 | GMA | 0.4 | St | 0.1 | HEMA | 0.2 | — | — | 6,000 |
| B-8 | PHSEVE | 0.3 | OXE-30 | 0.4 | MAA | 0.1 | HEMA | 0.2 | — | — | 6,000 |
| B-9 | PHSEVE | 0.4 | GMA | 0.2 | PHS | 0.4 | — | — | — | — | 9,500 |
| B-10 | PHStBOC | 0.3 | OXE-30 | 0.4 | MAA | 0.1 | HEMA | 0.2 | — | — | 6,000 |
| B"-1 | — | — | GMA | 0.63 | St | 0.22 | MAA | 0.52 | DCPM | 0.26 | 13,000 |
| B"-2 | — | — | OXE-30 | 0.63 | St | 0.22 | MAA | 0.52 | DCPM | 0.26 | 12,000 |

The abbreviations in Table 1 are as follows.
MAEVE: 1-ethoxyethyl methacrylate
MACHVE: 1-cyclohexyloxyethyl methacrylate
MATHF: tetrahydrofuran-2-yl methacrylate
t-BMA: tert-butyl methacrylate
GMA: glycidyl methacrylate
OXE-30: (3-ethyloxetan-3-yl)methyl methacrylate (Osaka Organic Chemical Industry Ltd.)
MAA: methacrylic acid
HEMA: 2-hydroxyethyl methacrylate
St: styrene
PHS: 4-hydroxystyrene
PHSEVE: 4-(1-ethoxyethyloxy)styrene
PHStBOC: 4-(t-butoxycarbonyloxy)styrene
CHMI: N-cyclohexylmaleimide
DCPM: dicyclopentanyl methacrylate MACHVE and MATHPE were synthesized by changing the vinyl ether used in the synthesis of MAEVE to cyclohexyl vinyl ether and dihydrohydropyran respectively.

PHSEVE was synthesized by changing the methacrylic acid used in the synthesis of MAEVE to 4-hydroxystyrene.

Examples 1-2 to 1-30 and Comparative Examples 1-1 to 1-3

Photosensitive resin compositions of Examples 1-2 to 1-30 and Comparative Examples 1-1 to 1-3 were prepared by dissolving and mixing the same amounts as those in Example 1-1 except that the compounds used in Example 1-1 were changed to the compounds shown in Table 2.

B"-1 used in Example 1-15 and B"-2 used in Example 1-16 were added at solids contents of 20 parts and 25 parts respectively.

Details of the abbreviations for the compounds used in Examples 1-1 to 1-30 and Comparative Examples 1-1 to 1-3 are as follows.
AX-3: CGI-1397 (structure shown below, Ciba Specialty Chemicals)
C-1: propylene glycol monomethyl ether acetate
C-2: diethylene glycol ethyl methyl ether
D-1: NBCA (10-butyl-2-chloroacridone, structure shown below, Kurogane Kasei Co., Ltd.)

D-2: DBA (9,10-dibutoxyanthracene, structure shown below, Kawasaki Kasei Chemicals Ltd.)
D-3: DETX (2,4-diethylthioxanthen-9-one, structure shown below, Tokyo Chemical Industry Co., Ltd.)
E-1: KBM-403 (3-glycidoxypropyltrimethoxysilane, structure shown below, Shin-Etsu Chemical Co., Ltd.)
F-1: perfluoroalkyl group-containing nonionic surfactant represented by structural formula (W-3) below
F-2: PolyFox PF-6320 (fluorine-based surfactant, OMNOVA)
G-1: JER157S65 (crosslinking agent, Japan Epoxy Resins Co., Ltd)
I-1: triphenylimidazole (Tokyo Chemical Industry Co., Ltd.)
I-2: 1,8-diazabicyclo[5.4.0]undecene-7 (Tokyo Chemical Industry Co., Ltd.)

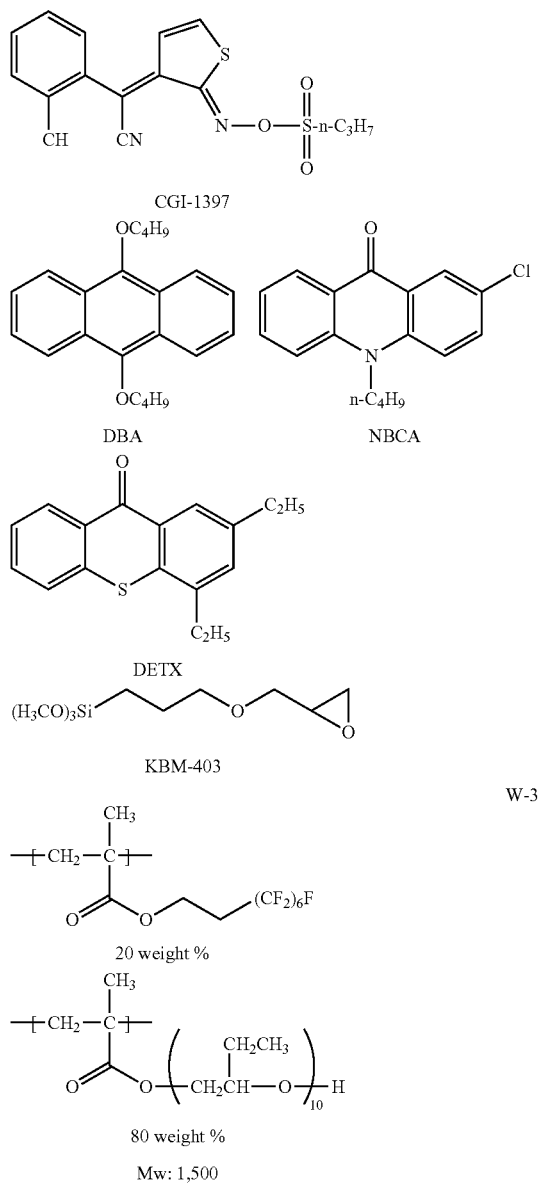

The photosensitive resin compositions of Examples 1-1 to 1-30 and Comparative Examples 1-1 to 1-3 obtained above were subjected to the evaluations described below. The evaluation results are shown in Table 2.

<Evaluation of Liquid Stability Over Time (Liquid Storage Stability)>

The viscosity (initial viscosity) of the photosensitive resin composition immediately after preparation and the viscosity (viscosity over time) of the photosensitive resin composition after being stored at 30° C. for one week and two weeks were measured using a model E viscometer (Toki Sangyo Co., Ltd.).

With regard to the evaluation criteria, when the initial viscosity was defined as 100%, one with a viscosity that had changed over time by at least 10% was evaluated as '3', one with a viscosity change of at least 5% but less than 10% was evaluated as '2', and one with a viscosity change of less than 5% was evaluated as '1'. '1' and '2' are levels without practical problems.

<Evaluation of Sensitivity>

After each photosensitive resin composition was applied onto a glass substrate (Corning 1737, 0.7 mm thick (Corning)) by slit coating, it was prebaked on a hotplate at 90° C./120 sec. to thus evaporate the solvent and form a photosensitive resin composition layer having a film thickness of 3.0 μm.

Subsequently, the photosensitive resin composition layer thus obtained was exposed via a predetermined mask using a PLA-501F exposure device (super high pressure mercury lamp) manufactured by Canon Inc. The exposed photosensitive composition layer was developed using an alkali developer (0.4 wt % tetramethylammonium hydroxide aqueous solution) at 23° C./60 sec. and then rinsed using ultrapure water for 20 sec.

The optimum i-line exposure (Eopt) when a 1:1 10 μm line and space pattern was resolved by the above operations was defined as the sensitivity. The evaluation criteria were as follows. '1' and '2' are levels without practical problems.

1: less than 40 $mJ/cm^2$
2: at least 40 $mJ/cm^2$ but less than 60 $mJ/cm^2$
3: at least 60 $mJ/cm^2$ but less than 80 $mJ/cm^2$
4: at least 80 $mJ/cm^2$ <Evaluation of Transparency>

After each photosensitive resin composition was applied onto a glass substrate (Corning 1737, 0.7 mm thick (Corning)) by slit coating, the solvent was removed by heating it on a hotplate at 90° C./120 sec., and a photosensitive resin composition layer having a film thickness of 3.0 μm was formed.

The photosensitive resin composition layer thus obtained was exposed at an integrated irradiance of 300 $mJ/cm^2$ (illumination intensity: 20 $mW/cm^2$, i-line) using a PLA-501F exposure device (super high pressure mercury lamp) manufactured by Canon Inc, and subsequently this substrate was heated in an oven at 230° C. for 1 hour, thus giving a cured film.

The light transmittance of the glass substrate having the cured film was measured using a Model 150-20 double beam spectrophotometer (Hitachi, Ltd.) at a wavelength in the range of 400 to 800 nm. The lowest light transmittance at this time was used for the evaluation of transparency and is shown in Table 2.

The evaluation criteria were as follows. '1' and '2' are levels without practical problems.

1: at least 95%
2: at least 90% but less than 95%
3: at least 88% but less than 90%
4: less than 88%<

<Evaluation of Development Latitude>

Each photosensitive resin composition was applied onto a glass substrate (Corning 1737, 0.7 mm thick (Corning)) using a spinner, and the solvent was then removed on a hotplate at 100° C./60 sec., thus forming a photosensitive resin composition layer having a film thickness of 3.0 μm.

Subsequently, the photosensitive resin composition layer thus obtained was exposed via a mask having a 10 μm square pattern opening at an exposure (illumination intensity: 20 mW/cm$^2$, i-line) that could give a 10 μm square contact hole pattern after developing at 23° C. for 60 sec with a 0.4 wt % tetramethylammonium hydroxide aqueous solution as a developer.

The exposed substrate was subjected to paddle development using a 0.4 wt % tetramethylammonium hydroxide aqueous solution as a developer at 23° C. for 40 sec. and 80 sec.

When the difference between the contact hole diameter at this time and 10 μm was less than 0.5 μm, it could be said that the development latitude at the time of development of the photosensitive resin composition was good.
1: less than 0.3 μm
2: at least 0.3 μm but less than 0.5 μm
3: at least 0.5 μm (Synthesis of Oxime Sulfonate Compound)
<Synthesis of A'-1>

Aluminum chloride (1.02 kg) and chloroacetyl chloride (0.86 kg) were added to a suspension of 2-naphthol (1 kg) in chlorobenzene (3 L), and a reaction was carried out by heating the mixture at 40° C. for 2 hours. The reaction mixture was poured into a 4N HCl aqueous solution (3 L), and subsequently ethyl acetate (3 L) was added and a separation was carried out. The organic layer was washed with saturated brine, potassium carbonate (1.92 g) and water (3 L) were then added thereto, and stirring was carried out at 40° C. for 30 min. The organic layer was separated and concentrated, following this methanol (3 L), acetic acid (1 kg), and a 50 wt % hydroxylamine aqueous solution (1 kg) were added, and the mixture was refluxed by heating. After leaving to cool, water (3 L) was added, and the crystals thus precipitated were collected by filtration, thus giving naphthofuranone oxime (1.07 kg).

p-Toluenesulfonyl chloride (1.1 kg) was added to a solution of the oxime compound (1 kg) thus obtained and triethy-

TABLE 2

| | Component A | Component B | Component B" | Solvent | Sensitizer | Adhesion improving agent | Surfactant | Cross Linking agent | Basic compound | Evaluation results | | | Development latitude | |
|---|---|---|---|---|---|---|---|---|---|---|---|---|---|---|
| | | | | | | | | | | Liquid storage stability | Sensitivity | Transparency | 40 sec. | 80 sec. |
| Ex. 1-1 | A-1 | B-1 | None | C-1 | D-1 | E-1 | F-1 | G-1 | 1-1, 1-2 | 1 | 1 | 1 | 1 | 1 |
| Ex. 1-2 | A-2 | B-2 | None | C-1:C-2 = 50:50 | D-2 | E-1 | F-2 | None | I-2 | 2 | 2 | 1 | 1 | 1 |
| Ex. 1-3 | A-1 | B-3 | None | C-1 | None | E-1 | F-1 | None | 1-1, 1-2 | 1 | 1 | 1 | 1 | 1 |
| Ex. 1-4 | A-3 | B-4 | None | C-1 | D-3 | E-1 | F-1 | G-1 | I-2 | 2 | 2 | 1 | 1 | 1 |
| Ex. 1-5 | A-5 | B-5 | None | C-1:C-2 = 60:40 | D-1 | E-1 | F-1 | G-1 | 1-1, 1-2 | 2 | 1 | 1 | 1 | 1 |
| Ex. 1-6 | A-1 | B-6 | None | C-1:C-2 = 70:30 | None | E-1 | F-1 | G-1 | None | 2 | 1 | 1 | 1 | 1 |
| Ex. 1-7 | A-4 | B-7 | None | C-1 | D-1 | E-1 | F-1 | None | 1-1, 1-2 | 1 | 2 | 1 | 1 | 1 |
| Ex. 1-8 | A-1 | B-8 | None | C-1:C-2 = 40:60 | None | E-1 | F-1 | G-1 | I-2 | 1 | 1 | 2 | 1 | 1 |
| Ex. 1-9 | A-4 | B-9 | None | C-1 | D-1 | E-1 | F-1 | G-1 | I-2 | 1 | 2 | 2 | 2 | 2 |
| Ex. 1-10 | A-1 | B-10 | None | C-1 | None | E-1 | F-1 | G-1 | I-2 | 1 | 1 | 2 | 2 | 2 |
| Ex. 1-11 | A-6 | B-1 | None | C-1 | None | E-1 | F-1 | G-1 | 1-1, 1-2 | 1 | 1 | 1 | 2 | 1 |
| Ex. 1-12 | A-6 | B-3 | None | C-1 | None | None | F-1 | G-1 | 1-1, 1-2 | 1 | 1 | 1 | 1 | 1 |
| Ex. 1-13 | A-7 | B-1 | None | C-1 | None | E-1 | F-1 | G-1 | 1-1, 1-2 | 1 | 1 | 1 | 1 | 1 |
| Ex. 1-14 | A-7 | B-3 | None | C-1 | None | E-1 | F-1 | G-1 | 1-1, 1-2 | 1 | 1 | 1 | 1 | 1 |
| Ex. 1-15 | A-1 | B-3 | B"-1 | C-1 | D-1 | E-1 | F-1 | G-1 | 1-1, 1-2 | 2 | 1 | 2 | 1 | 1 |
| Ex. 1-16 | A-1 | B-3 | B"-2 | C-1 | None | E-1 | F-1 | G-1 | 1-1, 1-2 | 1 | 1 | 1 | 2 | 1 |
| Ex. 1-17 | A-8 | B-3 | None | C-1:C-2 = 70:30 | None | E-1 | F-1 | G-1 | 1-1, 1-2 | 1 | 2 | 1 | 1 | 1 |
| Ex. 1-18 | A-9 | B-3 | None | C-1 | D-2 | E-1 | F-1 | G-1 | 1-1, 1-2 | 1 | 2 | 1 | 1 | 1 |
| Ex. 1-19 | A-10 | B-5 | None | C-1 | None | E-1 | F-1 | G-1 | 1-1, 1-2 | 1 | 1 | 1 | 1 | 1 |
| Ex. 1-20 | A-11 | B-3 | None | C-1 | None | E-1 | F-1 | G-1 | 1-1, 1-2 | 1 | 1 | 1 | 1 | 1 |
| Ex. 1-21 | A-12 | B-1 | None | C-1 | D-2 | E-1 | F-1 | G-1 | 1-1, 1-2 | 1 | 1 | 1 | 1 | 1 |
| Ex. 1-22 | A-13 | B-3 | None | C-1 | None | None | F-1 | G-1 | 1-1, 1-2 | 1 | 1 | 2 | 1 | 1 |
| Ex. 1-23 | A-14 | B-3 | None | C-1 | None | E-1 | F-1 | G-1 | 1-1, 1-2 | 2 | 1 | 2 | 1 | 1 |
| Ex. 1-24 | A-15 | B-3 | None | C-1 | None | E-1 | F-1 | G-1 | 1-1, 1-2 | 1 | 1 | 1 | 2 | 1 |
| Ex. 1-25 | A-16 | B-3 | None | C-1:C-2 = 60:40 | None | E-1 | F-1 | G-1 | 1-1, 1-2 | 2 | 1 | 1 | 1 | 1 |
| Ex. 1-26 | A-17 | B-3 | None | C-1 | D-2 | E-1 | F-1 | G-1 | 1-1, 1-2 | 1 | 1 | 2 | 1 | 1 |
| Ex. 1-27 | A-18 | B-3 | None | C-1 | D-3 | E-1 | F-1 | G-1 | 1-1, 1-2 | 1 | 1 | 1 | 1 | 1 |
| Ex. 1-28 | A-19 | B-3 | None | C-1 | None | E-1 | F-1 | G-1 | 1-1, 1-2 | 2 | 1 | 1 | 1 | 1 |
| Ex. 1-29 | A-20 | B-3 | None | C-1 | None | E-1 | F-1 | G-1 | 1-1, 1-2 | 1 | 1 | 1 | 1 | 1 |
| Ex. 1-30 | A-21 | B-3 | None | C-1 | None | E-1 | F-1 | G-1 | 1-1, 1-2 | 2 | 1 | 1 | 1 | 1 |
| Comp. Ex. 1-1 | AX-1 | B-8 | None | C-1:C-2 = 40:60 | None | E-1 | F-1 | G-1 | I-2 | 3 | 2 | 4 | 2 | 3 |
| Comp. Ex. 1-2 | AX-2 | B-9 | None | C-1 | D-1 | E-1 | F-1 | G-1 | I-2 | 3 | 2 | 4 | 3 | 2 |
| Comp. Ex. 1-3 | AX-3 | B-10 | None | C-1 | None | E-1 | F-1 | G-1 | I-2 | 2 | 4 | 3 | 2 | 3 |

As shown in Table 2, the photosensitive resin compositions of Examples 1-1 to 1-30 using the first composition of the present invention gave excellent results that, in contrast to the Comparative Examples, satisfied all of liquid storage stability, sensitivity, transparency, and development latitude.

lamine (0.6 kg) in acetone (3 L), after confirming that the reaction was completed water (2 L) was added, the crystals thus precipitated were collected by filtration, and the crystals thus obtained were washed with methanol (2 L), thus giving A'-1 (1.4 kg).

$^1$H-NMR spectrum (300 MHz, CDCl$_3$) of A'-1: δ=8.3 (d, 1H), 8.0 (d, 2H), 7.9 (d, 1H), 7.8 (d, 1H), 7.6 (dd, 1H), 7.4 (dd, 1H), 7.3 (d, 2H), 7.1 (d, 1H), 5.3 (s, 1H), 2.4 (s, 3H).

<Synthesis of A'-2>

A'-2 was synthesized in the same manner as for A'-1 except that o-toluenesulfonyl chloride was used instead of the p-toluenesulfonyl chloride used for A'-1.

$^1$H-NMR spectrum (300 MHz, CDCl$_3$) of A'-2: δ=8.2 (d, 1H), 8.1 (d, 1H), 7.9 (d, 1H), 7.8 (d, 1H), 7.6 (dd, 1H), 7.6 (dd, 1H), 7.4 (dd, 1H), 7.4 (dd, 1H), 7.3 (d, 1H), 7.1 (d, 1H), 5.3 (s, 2H), 2.7 (s, 3H).

<Synthesis of A'-3>

A'-3 was synthesized in the same manner as for A'-1 except that benzenesulfonyl chloride was used instead of the p-toluenesulfonyl chloride used for A'-1.

$^1$H-NMR spectrum (300 MHz, CDCl$_3$) of A'-3: δ=8.3 (d, 1H), 8.0 (d, 2H), 7.9 (d, 1H), 7.8 to 7.6 (m, 5H), 7.4 (dd, 1H), 7.1 (d, 1H), 5.3 (s, 2H).

<Synthesis of A'-4>

A'-4 was synthesized in the same manner as for A'-1 except that methanesulfonyl chloride was used instead of the p-toluenesulfonyl chloride used for A'-1.

$^1$H-NMR spectrum (300 MHz, CDCl$_3$) of A'-4: δ=8.4 (d, 1H), 8.0 (d, 1H), 7.9 (d, 1H), 7.7 (t, 5H), 7.5 (t, 1H), 7.2 (d, 1H), 5.4 (s, 2H), 3.3 (s, 3H).

<Synthesis of A'-5>

A'-5 was synthesized in the same manner as for A'-1 except that n-propanesulfonyl chloride was used instead of the p-toluenesulfonyl chloride used for A'-1.

$^1$H-NMR spectrum (300 MHz, CDCl$_3$) of A'-5: δ=8.4 (d, 1H), 8.0 (d, 1H), 7.9 (d, 1H), 7.7 (t, 5H), 7.5 (t, 1H), 7.2 (d, 1H), 5.4 (s, 2H), 3.5 (t, 2H), 2.0 (m, 2H), 0.9 (t, 3H).

<Synthesis of A'-6>

A'-6 was synthesized in the same manner as for A'-1 except that 2-mercaptonaphthalene was used instead of the 2-naphthol used for A'-1.

$^1$H-NMR spectrum (300 MHz, CDCl$_3$) of A'-6: δ=9.2 (d, 1H), 8.0 (d, 1H), 8.0 (d, 2H), 7.9 (d, 1H), 7.7 (t, 1H), 7.4 (d, 1H), 4.7 (s, 2H), 2.4 (s, 3H).

<Synthesis of A'-7>

A'-7 was synthesized in the same manner as for A'-6 except that trifluoromethanesulfonyl chloride was used instead of the p-toluenesulfonyl chloride used for A'-6.

$^1$H-NMR spectrum (300 MHz, CDCl$_3$) of A'-7: δ=9.2 (d, 1H), 8.0 (d, 1H), 7.9 (d, 1H), 7.7 (t, 1H), 7.4 (d, 1H), 7.3 (d, 2H), 4.7 (s, 2H).

<Synthesis of A'-8>

A'-8 was synthesized in the same manner as for A'-1 except that 1-naphthol was used instead of the 2-naphthol used for A'-1.

$^1$H-NMR spectrum (300 MHz, CDCl$_3$) of A'-8: δ=8.1 (d, 1H), 7.9 (d, 2H), 7.8 (d, 1H), 7.7 (dd, 1H), 7.6 (dd, 1H), 7.6 (d, 1H), 7.4 (d, 1H), 7.3 (d, 2H), 5.3 (s, 2H), 2.4 (s, 3H).

<Synthesis of A'-9>

A'-9 was synthesized in the same manner as for A'-8 except that methanesulfonyl chloride was used instead of the p-toluenesulfonyl chloride used for A'-8.

$^1$H-NMR spectrum (300 MHz, CDCl$_3$) of A'-9: δ=8.1 (d, 1H), 7.8 (d, 1H), 7.7 (d, 1H), 7.6 to 7.4 (m, 3H), 5.4 (s, 2H), 3.3 (s, 3H).

<Synthesis of A'-10>

A'-10 was synthesized in the same manner as for A'-1 except that phenol was used instead of the 2-naphthol used for A'-1.

$^1$H-NMR spectrum (300 MHz, CDCl$_3$) of A'-10: δ=7.9 (d, 2H), 7.6 (d, 1H), 7.4 (dd, 1H), 7.3 (d, 2H), 6.9 (dd, 1H), 6.8 (d, 2H), 6.1 (s, 2H), 2.4 (s, 3H).

<Synthesis of A'-11>

2-Naphthalaldehyde (47 g) and malonic acid (62.4 g) were dissolved in pyridine (300 mL), piperidine (18 mL) was added dropwise thereto, and a reaction was then carried out at 80° C. for 6 hours. After leaving to cool, the reaction mixture was poured into a 1N HCl aqueous solution (1 L), and the crystals thus precipitated were filtered and then recrystallized from methanol, thus giving an unsaturated carboxylic acid (50 g).

A 5% palladium/activated carbon catalyst (0.5 g) was added to a suspension of the unsaturated carboxylic acid (10 g) thus obtained in tetrahydrofuran (100 mL), hydrogen was added using a rubber balloon at normal pressure (1 atm), and a reaction was carried out for 10 hours. The reaction mixture was filtered using Celite and then concentrated, and the crystals thus obtained was reslurried using a mixed solvent of hexane/ethyl acetate, thus giving a saturated carboxylic acid (7.7 g).

The saturated carboxylic acid (7.6 g) thus obtained was dissolved in methanesulfonic acid (80 mL), and a reaction was carried out at 80° C. for 2 hours. The reaction mixture was poured into water (500 mL), and the crystals thus precipitated were filtered, washed with water, then reslurried with diisopropyl ether, filtered, and dried, thus giving a ketone compound (4.2 g).

The ketone compound (4.2 g) thus obtained was subjected to oximation and sulfonation in the same manner as for A'-1, thus synthesizing A'-11 (6.0 g).

$^1$H-NMR spectrum (300 MHz, CDCl$_3$) of A'-11: δ=8.7 (d, 1H), 8.1 (d, 2H), 7.9 (d, 1H), 7.8 (d, 1H), 7.7 (dd, 1H), 7.6 (dd, 1H), 7.4 (d, 1H), 7.3 (d, 2H), 2.7 to 2.6 (m, 4H), 2.4 (s, 3H).

<Synthesis of A'-12>

Triethylamine (4.9 g) and p-toluenesulfonyl chloride (7.8 g) were added to a solution of 1-indanoneoxime (5.0 g) in acetone (20 mL) under ice cooling, and a reaction was carried out at room temperature for 1 hour. Water (100 mL) was added thereto, and the crystals thus precipitated were filtered, then reslurried with cold methanol (50 mL), filtered, and dried, thus giving A'-12 (9.7 g).

$^1$H-NMR spectrum (300 MHz, CDCl$_3$) of A'-12: δ=7.9 (d, 2H), 7.7 (d, 2H), 7.4 (dd, 1H), 7.4 to 7.3 (m, 3H), 7.2 (d, 1H), 3.1 to 2.9 (m, 4H), 2.4 (s, 3H).

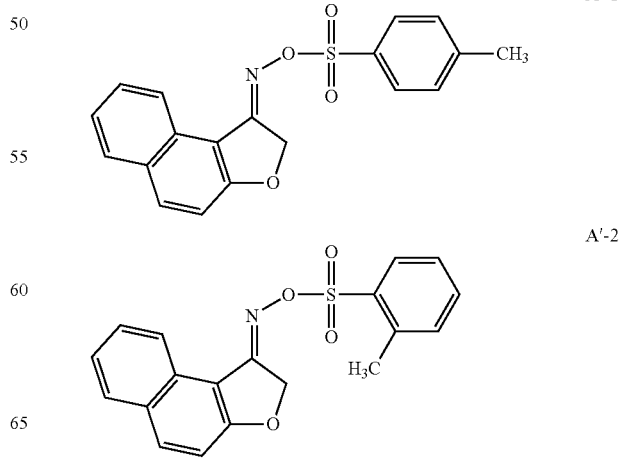

A'-3 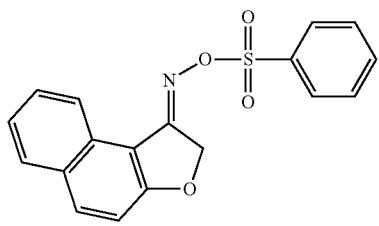

A'-4 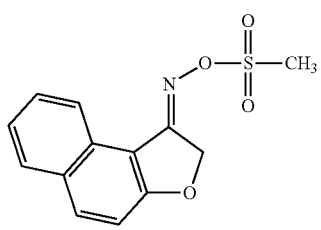

A'-5 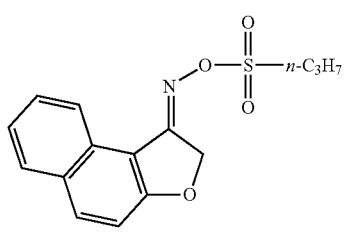

A'-6 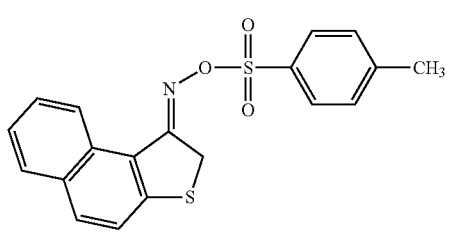

A'-7 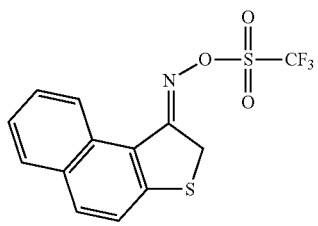

A'-8 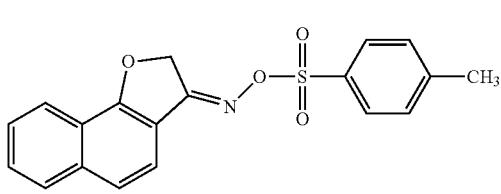

A'-9 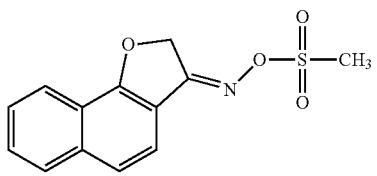

A'-10 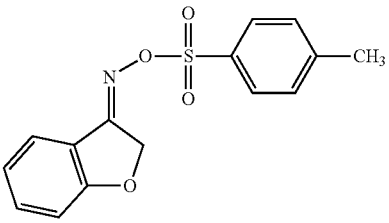

A'-11 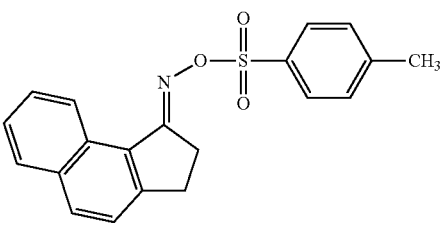

A'-12 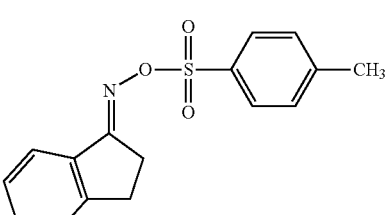

The following symbols denote the compounds in the Synthetic Examples below.

V-65: 2,2'-azobis(2,4-dimethylvaleronitrile)
GMA: glycidyl methacrylate
MAA: methacrylic acid
HEMA: 2-hydroxyethyl methacrylate
EDM: diethylene glycol ethyl methyl ether
PGMEA: propylene glycol monomethyl ether acetate <Synthesis of Copolymer B'-1>

Copolymer B'-1 was synthesized by the following method.

1-Ethoxyethyl methacrylate (MAEVE) was synthesized in the same manner as in the method described in <Synthesis of copolymer B-1> above.

A mixed solution of the MAEVE (63.28 parts (0.4 molar equivalents)) thus obtained, OXE-30 (55.27 parts (0.3 molar equivalents)), MAA (8.61 parts (0.1 molar equivalents)), HEMA (26.03 parts (0.2 molar equivalents)), and EDM (110.8 parts) was heated at 70° C. under a flow of nitrogen. While stirring, this mixed solution was added dropwise to a mixed solution of V-65 radical polymerization initiator (Wako Pure Chemical Industries, Ltd., 7 parts) and EDM (100.0 parts) over 2.5 hours. After the dropwise addition was completed, a reaction was carried out at 70° C. for 4 hours, thus giving an EDM solution of copolymer B-1 (solids content: 40%).

It was found by means of gel permeation chromatography (GPC) that the weight-average molecular weight (Mw) of the copolymer B'-1 thus obtained was 7,000.

<Synthesis of Copolymers B'-2 to B'-6>

Copolymers B'-2 to B'-6 were synthesized in the same manner as in the synthesis of copolymer B'-1 except that the monomers used and the amounts thereof used were changed as shown in Table 3 below.

The method for the synthesis of tetrahydrofuran-2-yl methacrylate (MATHF) was as described in <Synthesis of copolymers B-2 to B-10>.

TABLE 3

| Copolymer | Monomer having acid-decomposable group | | Other monomer 1 | | Other monomer 2 | | Other monomer 3 | | Mw |
|---|---|---|---|---|---|---|---|---|---|
| | Type | Molar equivalents | Type | Molar equivalents | Type | Molar equivalents | Type | Molar equivalents | |
| B'-1 | MAEVE | 0.4 | OXE-30 | 0.3 | MAA | 0.1 | HEMA | 0.2 | 7,000 |
| B'-2 | MAEVE | 0.4 | GMA | 0.3 | MAA | 0.1 | HEMA | 0.2 | 10,000 |
| B'-3 | MATHF | 0.4 | OXE-30 | 0.3 | MAA | 0.1 | HEMA | 0.2 | 17,000 |
| B'-4 | MATHF | 0.4 | GMA | 0.3 | MAA | 0.1 | HEMA | 0.2 | 12,000 |
| B'-5 | MATHF | 0.3 | OXE-30 | 0.5 | MAA | 0.2 | — | — | 11,000 |
| B'-6 | t-BMA | 0.3 | OXE-30 | 0.4 | MAA | 0.1 | HEMA | 0.2 | 7,000 |

In Table 3, the abbreviations are the same as those in Table 1.

Example 2-1

Components were dissolved and mixed so as to give the composition below, and filtered using a polytetrafluoroethylene filter having a pore size of 0.2 μm, thus giving a photosensitive resin composition of Example 2-1.

| | |
|---|---|
| Oxime sulfonate compound: A'-1 | 2.0 parts |
| Component B': polyethylene glycol methyl ether acetate (hereinafter, abbreviated to PGMEA) solution of copolymer B'-1 | 100.0 parts as solids content |
| Sensitizer: D-1 shown below | 2.0 parts |
| Adhesion improving agent: E-1 shown below | 0.5 parts |
| Surfactant: F-1 shown below | 0.02 parts |
| Crosslinking agent: G-1 shown below | 5.0 parts |
| Basic compound: I-1 shown below | 0.1 parts |

Examples 2-2 to 2-12, and Comparative Examples 2-1 to 2-7

Photosensitive resin compositions of Examples 2-2 to 2-12 and Comparative Examples 2-1 to 2-7 were prepared by dissolving and mixing the same amounts as those in Example 2-1 except that the compounds shown in Table 4 were used instead of the compounds used in Example 2-1.

Details of the abbreviations for the compounds used in Examples 2-1 to 2-12 and Comparative Examples 2-1 to 2-7 are as follows.

A'-13: CGI-1397 (structure shown below, Ciba Specialty Chemicals)
A'-14: PAI-101 (structure shown below, Midori Kagaku Co., Ltd)
A'-15: CGI-1906 (structure shown below, Ciba Specialty Chemicals)
B'-7: p-(1-ethoxyethoxy)styrene/p-hydroxystyrene copolymer; 1-ethoxyethoxy group degree of modification 40 mol %, Mw 9,500
B'-8: copolymer of (3-methacryloyloxypropyl) 4-(1-ethoxyethyloxy)benzoate/GMA/MAA/HEMA=40/30/10/20 (molar ratio), Mw 12,000
C-1: propylene glycol monomethyl ether acetate
C-2: diethylene glycol ethyl methyl ether
D-1: NBCA (10-butyl-2-chloroacridone, structure above, Kurogane Kasei Co., Ltd.)
D-2: DBA (9,10-dibutoxyanthracene, structure above, Kawasaki Kasei Chemicals Ltd.)
D-3: DETX (2,4-diethylthioxanthen-9-one, structure above, Tokyo Chemical Industry Co., Ltd.)
E-1: KBM-403 (3-glycidoxypropyltrimethoxysilane, structure above, Shin-Etsu Chemical Co., Ltd.)
F-1: perfluoroalkyl group-containing nonionic surfactant shown by Formula (W-3) above
F-2: PolyFox PF-6320 (fluorine-based surfactant, OMNOVA)
G-1: JER157S65 (crosslinking agent, Japan Epoxy Resins Co., Ltd)
I-1: 1,8-diazabicyclo[5.4.0]undecene-7 (Tokyo Chemical Industry Co., Ltd.)

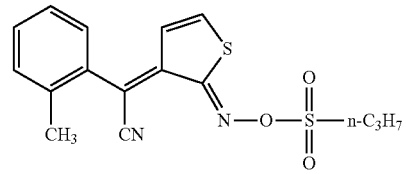

CGI-1397

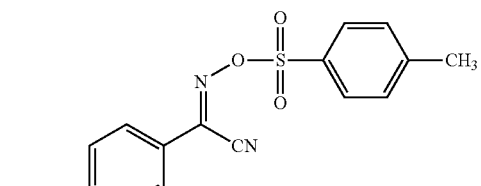

PAI-101

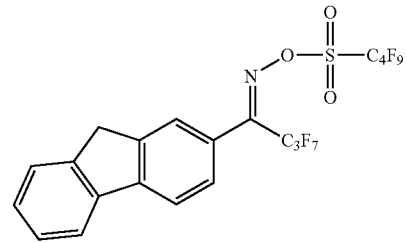

CGI-1906

The photosensitive resin compositions of Examples 2-1 to 2-12 and Comparative Examples 2-1 to 2-7 obtained above were subjected to the evaluations shown below. The evaluation results are shown in Table 4.

<Evaluation of Sensitivity>

After each photosensitive resin composition was applied onto a glass substrate (Corning 1737, 0.7 mm thick (Corning)) by slit coating, it was prebaked on a hotplate at 90° C./120 sec. to thus evaporate the solvent and form a photosensitive resin composition layer having a film thickness of 3.0 μm.

Subsequently, the photosensitive resin composition layer thus obtained was exposed via a predetermined mask using a PLA-501F exposure device (super high pressure mercury lamp) manufactured by Canon Inc. The exposed photosensitive composition layer was developed using an alkali developer (0.4 wt % tetramethylammonium hydroxide aqueous solution) at 23° C./60 sec. and then rinsed using ultrapure water for 20 sec.

The optimum i-line exposure (Eopt) when a 1:1 10 μm line and space pattern was resolved by the above operations was defined as the sensitivity. The evaluation criteria were as follows. '1' and '2' are levels without practical problems.
1: less than 40 mJ/cm$^2$
2: at least 40 mJ/cm$^2$ but less than 60 mJ/cm$^2$
3: at least 60 mJ/cm$^2$ but less than 80 mJ/cm$^2$
4: at least 80 mJ/cm$^2$ <Evaluation of Transparency>

After each photosensitive resin composition was applied onto a glass substrate (Corning 1737, 0.7 mm thick (Corning)) by slit coating, the solvent was removed by heating it on a hotplate at 90° C./120 sec., and a photosensitive resin composition layer having a film thickness of 3.0 μm was formed.

The photosensitive resin composition layer thus obtained was exposed at an integrated irradiance of 300 mJ/cm$^2$ (illumination intensity: 20 mW/cm$^2$, i-line) using a PLA-501F exposure device (super high pressure mercury lamp) manufactured by Canon Inc, and subsequently this substrate was heated in an oven at 230° C. for 1 hour, thus giving a cured film.

The light transmittance of the glass substrate having the cured film was measured using a Model 150-20 double beam spectrophotometer (Hitachi, Ltd.) at a wavelength in the range of 400 to 800 nm. The lowest light transmittance at this time was used for the evaluation of transparency and is shown in Table 4.

The evaluation criteria were as follows. '1' and '2' are levels without practical problems.
1: at least 92%
2: at least 90% but less than 92%
3: at least 88% but less than 90%
4: less than 88%

<Evaluation of Development Latitude>

Each photosensitive resin composition was applied onto a glass substrate (Corning 1737, 0.7 mm thick (Corning)) using a spinner, and the solvent was then removed on a hotplate at 100° C./60 sec., thus forming a photosensitive resin composition layer having a film thickness of 3.0 μm.

Subsequently, the photosensitive resin composition layer thus obtained was exposed via a mask having a 10 μm square pattern opening at an exposure (illumination intensity: 20 mW/cm$^2$, i-line) that could give a 10 μm square contact hole pattern after developing at 23° C. for 60 sec with a 0.4 wt % tetramethylammonium hydroxide aqueous solution as a developer.

The exposed substrate was subjected to paddle development using a 0.4 wt % tetramethylammonium hydroxide aqueous solution as a developer at 23° C. for 40 sec. and 80 sec.

When the difference between the contact hole diameter at this time and 10 μm was less than 0.5 μm, it could be said that the development latitude at the time of development of the photosensitive resin composition was good.
1: less than 0.3 μm
2: at least 0.3 μm but less than 0.5 μm
3: at least 0.5 μm

TABLE 4

| | | | | | | | | | | Evaluation results | |
|---|---|---|---|---|---|---|---|---|---|---|---|
| | Component A' | Component B' | Solvent | Sensitizer | Adhesion improving agent | Surfactant | Cross linking agent | Basic compound | Sensitivity | Transparency | Development latitude 40 sec. | Development latitude 80 sec. |
| Ex. 2-1 | A'-1 | B'-1 | C-1 | D-1 | E-1 | F-1 | G-1 | I-1 | 1 | 1 | 1 | 1 |
| Ex. 2-2 | A'-2 | B'-3 | C-1:C-2 = 50:50 | D-2 | E-1 | F-1 | None | I-1 | 1 | 1 | 1 | 1 |
| Ex. 2-3 | A'-3 | B'-2 | C-1:C-2 = 60:40 | D-3 | E-1 | F-1 | None | I-1 | 1 | 1 | 1 | 2 |
| Ex. 2-4 | A'-4 | B'-1 | C-1 | None | E-1 | F-1 | G-1 | I-1 | 1 | 1 | 1 | 2 |
| Ex. 2-5 | A'-5 | B'-4 | C-1:C-2 = 80:20 | D-1 | E-1 | F-1 | G-1 | I-1 | 1 | 1 | 1 | 1 |
| Ex. 2-6 | A'-6 | B'-3 | C-1 | D-1 | E-1 | F-1 | G-1 | I-1 | 1 | 1 | 1 | 1 |
| Ex. 2-7 | A'-7 | B'-1 | C-1:C-2 = 50:50 | D-1 | E-1 | F-1 | None | I-1 | 1 | 1 | 1 | 1 |
| Ex. 2-8 | A'-8 | B'-3 | C-1 | D-1 | E-1 | F-1 | G-1 | I-1 | 1 | 1 | 2 | 1 |
| Ex. 2-9 | A'-9 | B'-1 | C-1 | D-1 | E-1 | F-1 | G-1 | I-1 | 1 | 2 | 1 | 1 |
| Ex. 2-10 | A'-10 | B'-3 | C-1 | D-1 | E-1 | F-2 | G-1 | I-1 | 1 | 2 | 1 | 1 |
| Ex. 2-11 | A'-1 | B'-5 | C-1 | D-1 | E-1 | F-1 | G-1 | None | 1 | 1 | 1 | 2 |
| Ex. 2-12 | A'-1 | B'-6 | C-1 | D-1 | None | F-1 | G-1 | I-1 | 2 | 1 | 1 | 1 |
| Comp. Ex. 2-1 | A'-11 | B'-1 | C-1 | D-1 | E-1 | F-1 | G-1 | I-1 | 3 | 1 | 2 | 1 |
| Comp. Ex. 2-2 | A-12 | B'-1 | C-1 | D-1 | E-1 | F-1 | G-1 | I-1 | 4 | 1 | 2 | 1 |
| Comp. Ex. 2-3 | A'-13 | B'-1 | C-1 | D-1 | E-1 | F-1 | G-1 | I-1 | 2 | 2 | 2 | 3 |
| Comp. Ex. 2-4 | A'-14 | B'-1 | C-1 | D-1 | E-1 | F-1 | G-1 | I-1 | 1 | 1 | 3 | 2 |
| Comp. Ex. 2-5 | A'-15 | B'-1 | C-1 | D-1 | E-1 | F-1 | G-1 | I-1 | 1 | 4 | 2 | 1 |
| Comp. Ex. 2-6 | A'-1 | B'-7 | C-1 | D-1 | E-1 | F-1 | G-1 | I-1 | 2 | 4 | 2 | 3 |
| Comp. Ex. 2-7 | A'-1 | B'-8 | C-1 | D-1 | E-1 | F-1 | G-1 | I-1 | 1 | 3 | 3 | 2 |

As shown in Table 4, the photosensitive resin compositions of Example 2-1 to 2-12 using the second photosensitive resin composition of the present invention gave excellent results that, in contrast to the Comparative Examples, satisfied all of sensitivity, transparency, and development latitude (development margin).

<Preparation of Organic EL Display Device>

An organic EL display device equipped with a thin film transistor (TFT) was produced by the following method (see FIG. 1).

A bottom gate type TFT 1 was formed above a glass substrate 6, and an insulating film 3 formed from $Si_3N_4$ was formed so as to cover the TFT 1. Subsequently, after a contact hole, which is not illustrated in the figure, was formed in the insulating film 3, wiring 2 (height 1.0 μm) was formed above the insulating film 3, the wiring 2 being connected to the TFT 1 via the contact hole. This wiring 2 was provided in order to provide a connection between the TFTs 1 or between the TFT 1 and an organic EL element formed in a subsequent step.

Furthermore, in order to planarize asperities due to formation of the wiring 2, a planarization layer 4 was formed above the insulating film 3 so as to bury the asperities due to the wiring 2. Formation of the planarization film 4 above the insulating film 3 was carried out by applying the photosensitive resin composition of Example 3 onto the substrate by spin coating, prebaking it on a hotplate (90° C.×2 min.), then carrying out i-line (365 nm) irradiation at 30 mJ/cm² (illumination intensity 20 mW/cm²) above a mask using a high-pressure mercury lamp, then developing using an alkali aqueous solution to thus form a pattern, and carrying out a thermal treatment at 230° C. for 60 min. The coating properties when applying the photosensitive resin composition were good, and the cured film obtained after exposure, development, and baking did not show the occurrence of creases or cracking. Furthermore, the average height of the wiring 2 was 500 nm, and the film thickness of the planarization film 4 thus produced was 2,000 nm.

Subsequently, a bottom emission type organic EL element was formed above the planarization film 4 thus obtained. To start with, a first electrode 5 formed from ITO was formed above the planarization film 4 so as to be connected to the wiring 2 via a contact hole 7. Following this, coating with a resist, pre-baking, and development by exposing via a desired pattern mask were carried out. Patterning was carried out by wet etching using an ITO etchant with this resist pattern as a mask. Subsequently, the resist pattern was stripped off using a resist stripping liquid (mixed liquid of monoethanolamine and dimethyl sulfoxide (DMSO)). The first electrode 5 thus obtained corresponded to a positive electrode of the organic EL element.

Subsequently, an insulating film 8 in a shape that covered the periphery of the first electrode 5 was formed. The insulating film 8 was formed by the same method as above using the photosensitive resin composition of Example 7. Providing this insulating film 8 enabled a short circuit between the first electrode 5 and a second electrode that was formed subsequent to this step to be prevented.

Furthermore, vapor deposition of a positive hole transport layer, an organic light-emitting layer, and an electron transport layer were carried out in sequence via a desired pattern mask within a vacuum evaporator. Following this, the second electrode was formed from Al above the entire surface of the substrate. The substrate thus obtained was taken out of the evaporator and sealed by affixing to a sealing glass plate using a UV curing type epoxy resin.

As hereinbefore described, an active matrix type organic EL display device was obtained in which a TFT 1 was connected to each organic EL element in order to drive it. When a voltage was applied thereto via a drive circuit, it was found that the organic EL display device had good display properties and high reliability.

| Explanation of Reference Numerals and Symbols | |
|---|---|
| 1: | TFT (thin film transistor) |
| 2: | Wiring |
| 3: | Insulating film |
| 4: | Planarization film |
| 5: | First electrode |
| 6: | Glass substrate |
| 7: | Contact hole |
| 8: | Insulating film |
| 10: | Liquid crystal display device |
| 12: | Back light unit |
| 14, 15: | Glass substrate |
| 16: | TFT |
| 17: | Cured film |
| 18: | Contact hole |
| 19: | ITO transparent electrode |
| 20: | Liquid crystal |
| 22: | Color filter |

What is claimed is:

1. A photosensitive resin composition comprising:
   (Component A) an oxime sulfonate compound represented by Formula (1);
   (Component B) a resin comprising a constituent unit having an acid-decomposable group that is decomposed by an acid to form a carboxyl group or a phenolic hydroxy group; and
   (Component C) a solvent

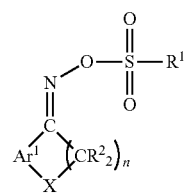

(1)

wherein in Formula (1) $R^1$ denotes an alkyl group, an aryl group, or a heteroaryl group, each $R^2$ independently denotes a hydrogen atom, an alkyl group, an aryl group, or a halogen atom, $Ar^1$ denotes an o-arylene group or an o-heteroarylene group, X denotes O or S, and n denotes 1 or 2, provided that of two or more $R^2$s present in the compound, at least one denotes an alkyl group, an aryl group, or a halogen atom.

2. The photosensitive resin composition according to claim 1, wherein Component B above further comprises a constituent unit derived from at least one compound selected from the group consisting of a styrene derivative, a maleimide derivative, (meth)acrylic acid, and a hydroxy group-containing (meth)acrylate compound.

3. The photosensitive resin composition according to claim 1, wherein Component B above further comprises a constituent unit having a functional group that can react with a carboxyl group or a phenolic hydroxy group to form a covalent bond.

4. The photosensitive resin composition according to claim 1, wherein the acid-decomposable group is a group represented by Formula (Ia), Formula (Ib), Formula (IIa), or Formula (IIb)

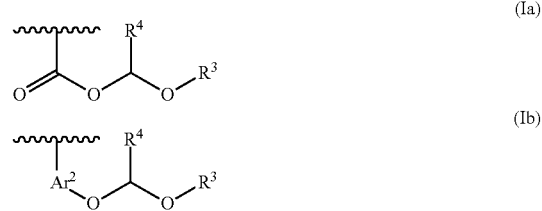

-continued

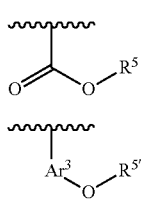
(IIa)

(IIb)

wherein in the Formulae R³ denotes an alkyl group or a cycloalkyl group, R⁴ denotes an alkyl group, R³ and R⁴ may form a ring, R⁵ denotes a tertiary alkyl group, R⁵' denotes a tertiary alkyl group or a tert-butoxycarbonyl group, Ar² and Ar³ independently denote a divalent aromatic group, and a wavy line portion denotes the position of bonding to another structure.

5. The photosensitive resin composition according to claim 1, wherein Component A above is an oxime sulfonate compound represented by Formula (2), Formula (3), or Formula (4)

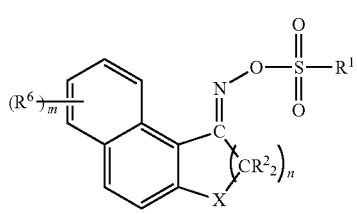
(2)

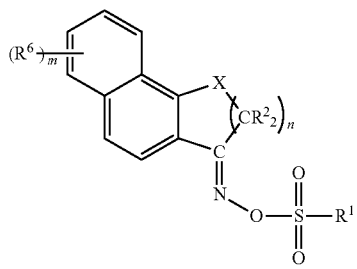
(3)

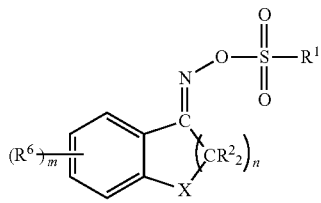
(4)

wherein in Formula (2) to Formula (4) R¹ denotes an alkyl group, an aryl group, or a heteroaryl group, each R² independently denotes a hydrogen atom, an alkyl group, an aryl group, or a halogen atom, each R⁶ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6, provided that of two or more R²s present in the compound, at least one is an alkyl group, an aryl group, or a halogen atom.

6. The photosensitive resin composition according to claim 1, wherein Component A above is an oxime sulfonate compound represented by any one of Formulae (5) to (10) below

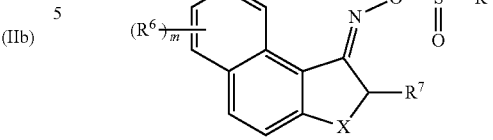
(5)

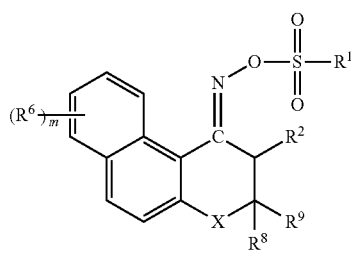
(6)

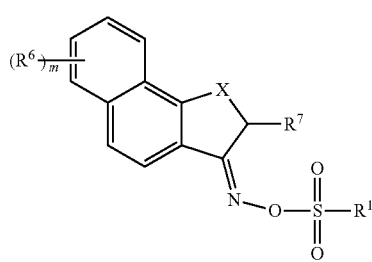
(7)

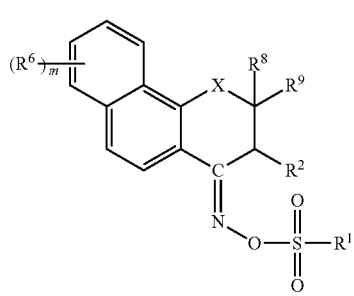
(8)

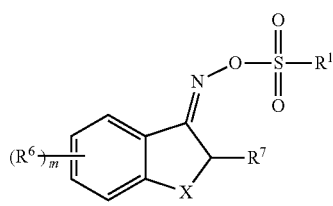
(9)

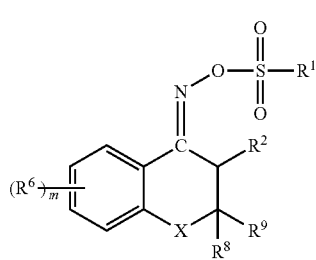
(10)

wherein in Formulae (5) to (10) R¹ denotes an alkyl group, an aryl group, or a heteroaryl group, R² denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, $R^7$ denotes an alkyl group, an aryl group, or a halogen atom, $R^8$ denotes a hydrogen atom or a methyl group, $R^9$ denotes a hydrogen atom, an alkyl group, or an aryl group, X denotes O or S, and m denotes an integer of 0 to 6, provided that in Formula (6), Formula (8), and Formula (10), not all of $R^2$, $R^8$, and $R^9$ are hydrogen atoms.

7. The photosensitive resin composition according to claim 1, wherein Component A above is an oxime sulfonate compound represented by any one of Formulae (11) to (16) below

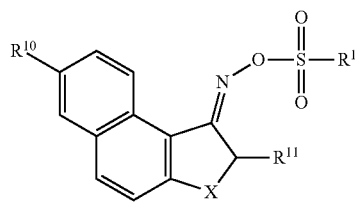 (11)

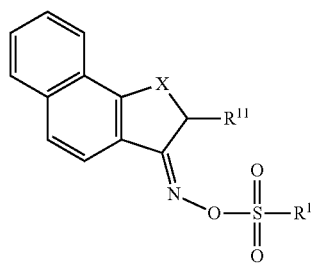 (12)

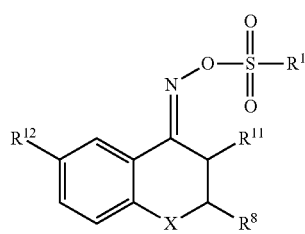 (13)

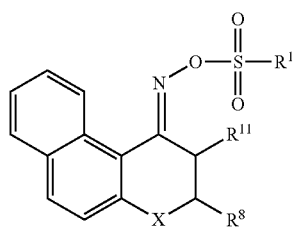 (14)

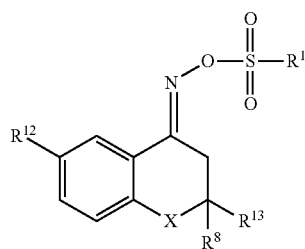 (15)

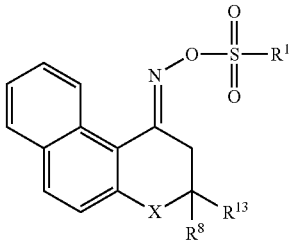 (16)

wherein in Formulae (11) to (16) $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, $R^{13}$ denotes an unsubstituted alkyl group having 1 to 8 carbons, a chloromethyl group, a bromomethyl group, a bromoethyl group, a methoxymethyl group, a phenyl group, or a chlorophenyl group, and X denotes O or S.

8. The photosensitive resin composition according to claim 1, wherein Component A above is an oxime sulfonate compound represented by any one of Formulae (17) to (22) below

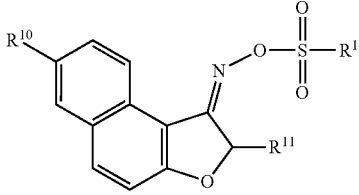 (17)

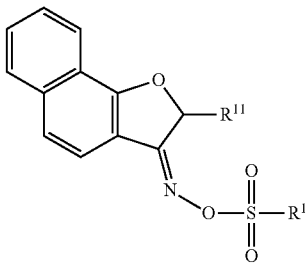 (18)

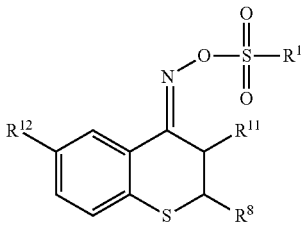 (19)

(20)

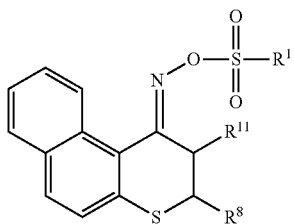

(21)

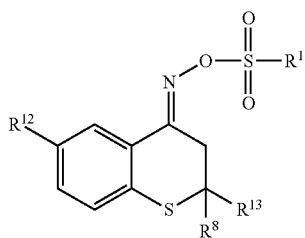

(22)

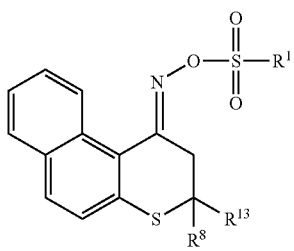

wherein in Formulae (17) to (22) R$^1$ denotes an alkyl group, an aryl group, or a heteroaryl group, R$^8$ denotes a hydrogen atom or a methyl group, R$^{10}$ denotes a hydrogen atom or a bromine atom, R$^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, R$^{12}$ denotes a hydrogen atom, a halogen atom, a methyl group, or a methoxy group, and R$^{13}$ denotes an unsubstituted alkyl group having 1 to 8 carbons, a chloromethyl group, a bromomethyl group, a bromoethyl group, a methoxymethyl group, a phenyl group, or a chlorophenyl group.

9. An oxime sulfonate compound represented by Formula (2), Formula (3), or Formula (4) below (2)

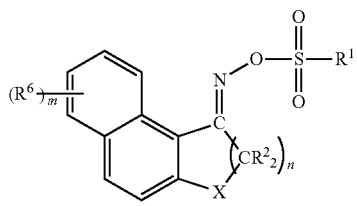

(3)

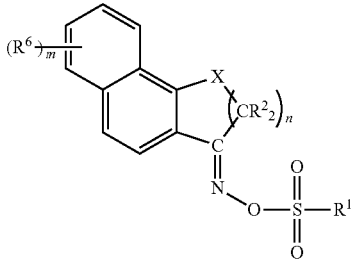

(4)

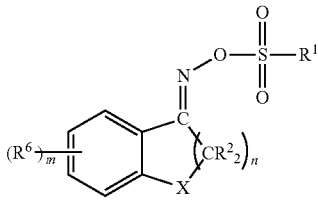

wherein in Formula (2) to Formula (4) R$^1$ denotes an alkyl group, an aryl group, or a heteroaryl group, each R$^2$ independently denotes a hydrogen atom, an alkyl group, an aryl group, or a halogen atom, each R$^6$ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6, provided that of two or more R$^2$s present in the compound, at least one is an alkyl group, an aryl group, or a halogen atom.

10. The oxime sulfonate compound according to claim 9, wherein it is represented by any one of Formulae (5) to (10) below (5)

(6)

(7)

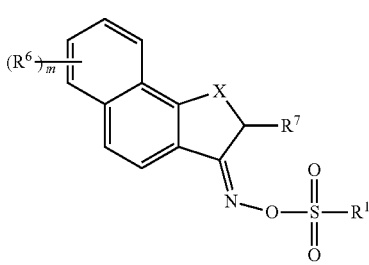

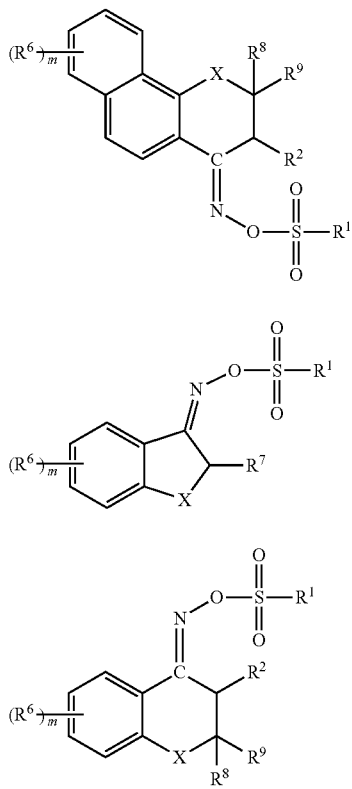

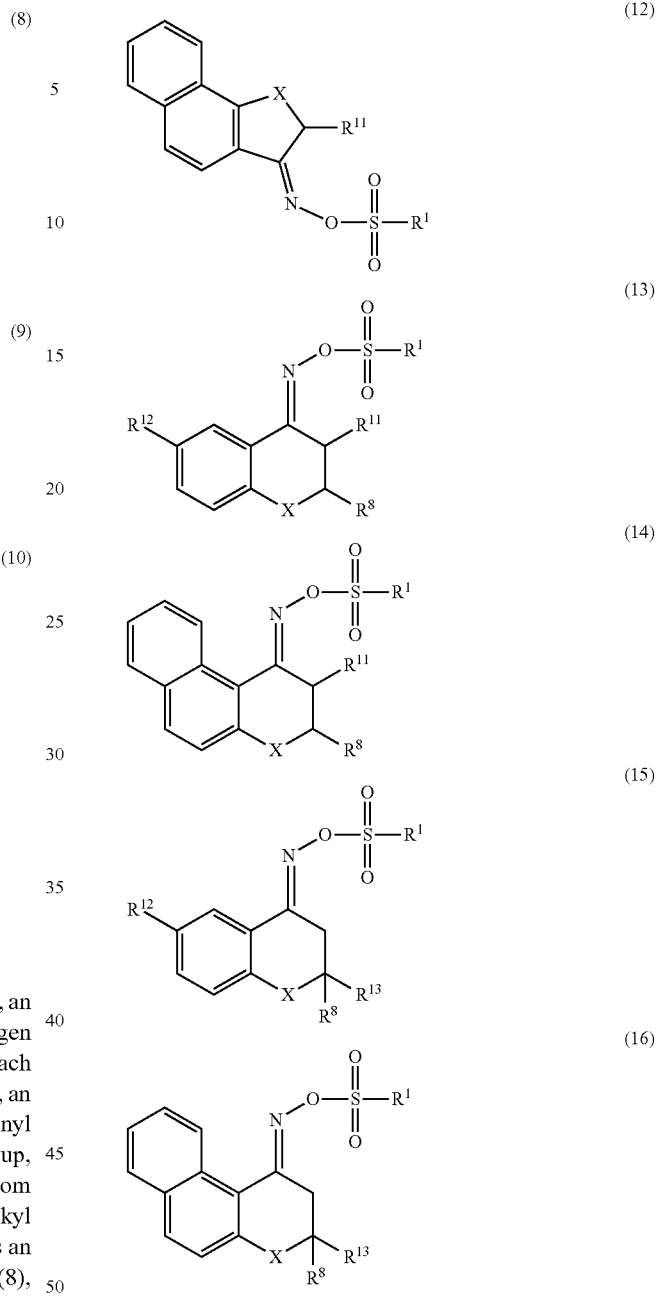

wherein in Formulae (5) to (10) $R^1$ denotes an alkyl group, an aryl group, or a heteroaryl group, $R^2$ denotes a hydrogen atom, an alkyl group, an aryl group, or a halogen atom, each $R^6$ independently denotes a halogen atom, an alkyl group, an alkyloxy group, a sulfonic acid group, an aminosulfonyl group, or an alkoxysulfonyl group, $R^7$ denotes an alkyl group, an aryl group, or a halogen atom, $R^8$ denotes a hydrogen atom or a methyl group, $R^9$ denotes a hydrogen atom, an alkyl group, or an aryl group, X denotes O or S, and m denotes an integer of 0 to 6, provided that in Formula (6), Formula (8), and Formula (10) not all of $R^2$, $R^8$, and $R^9$ are hydrogen atoms.

11. The oxime sulfonate compound according to claim 10, wherein it is represented by any one of Formulae (11) to (16) below

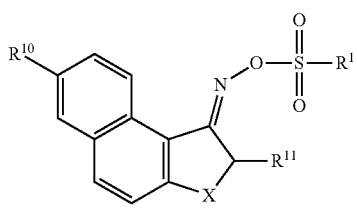

wherein in Formulae (11) to (16) $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a methoxy group, $R^{13}$ denotes an unsubstituted alkyl group having 1 to 8 carbons, a chloromethyl group, a bromomethyl group, a bromoethyl group, a methoxymethyl group, a phenyl group, or a chlorophenyl group, and X denotes O or S.

12. The oxime sulfonate compound according to claim 11, wherein it is represented by any one of Formulae (17) to (22) below

(17) 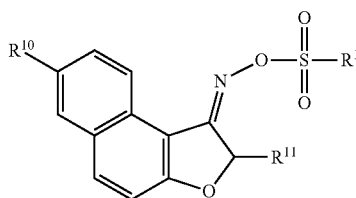

(18) 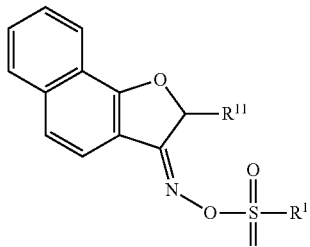

(19) 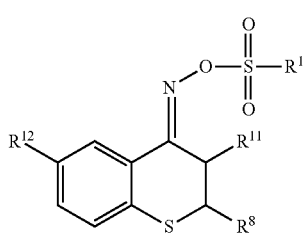

(20) 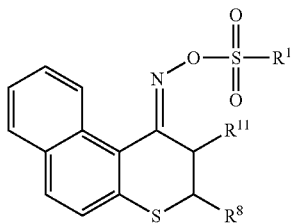

(21) 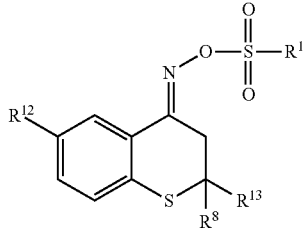

(22) 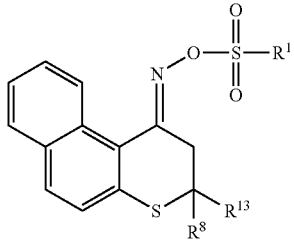

wherein in Formulae (17) to (22) $R^1$ denotes an alkyl group, an aryl group, or a heteroaryl group, $R^8$ denotes a hydrogen atom or a methyl group, $R^{10}$ denotes a hydrogen atom or a bromine atom, $R^{11}$ denotes an unsubstituted alkyl group having 1 to 8 carbons, a halogen atom, a chloromethyl group, a bromomethyl group, a bromoethyl group, a methoxymethyl group, a phenyl group, or a chlorophenyl group, $R^{12}$ denotes a hydrogen atom, a halogen atom, a methyl group, or a meth- oxy group, and $R^{13}$ denotes an unsubstituted alkyl group having 1 to 8 carbons, a chloromethyl group, a bromomethyl group, a bromoethyl group, a methoxymethyl group, a phenyl group, or a chlorophenyl group.

13. A photosensitive resin composition comprising:
(Component A') an oxime sulfonate compound represented by Formula (1');
(Component B') a (meth)acrylic copolymer comprising a constituent unit having an acid-decomposable group that is decomposed by an acid to form a carboxyl group, and
(Component C) a solvent (1') 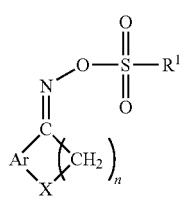

wherein in Formula (1') $R^1$ denotes an alkyl group, an aryl group, or a heteroaryl group, Ar denotes an o-arylene group or an o-heteroarylene group, X denotes O or S, and n denotes 1 or 2.

14. The photosensitive resin composition according to claim 13, wherein Component B' above is a (meth)acrylic copolymer comprising a constituent unit having a carboxyl group that is protected by an acetal group.

15. The photosensitive resin composition according to claim 13, wherein Component A' above is an oxime sulfonate compound represented by Formula (2'), Formula (3'), or Formula (4')

(2') 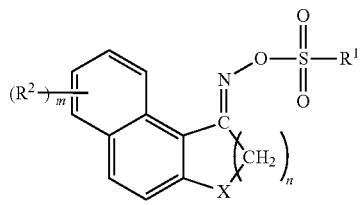

(3') 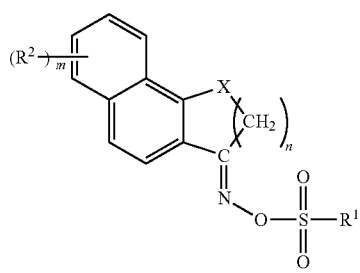

(4') 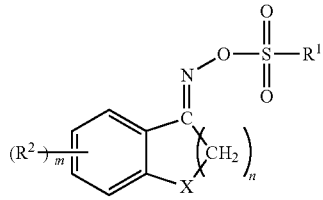

wherein in Formula (2') to Formula (4') $R^1$ denotes an alkyl group, an aryl group, or a heteroaryl group, each $R^2$ independently denotes a halogen atom, an alkyl group, an alkyloxy group, a sulfonic acid group, an aminosulfonyl group, or an alkoxysulfonyl group, X denotes O or S, n denotes 1 or 2, and m denotes an integer of 0 to 6.

16. The photosensitive resin composition according to claim 13, wherein Component B' above further comprises a constituent unit having a functional group that can react with a carboxyl group to form a covalent bond.

17. A method for forming a cured film, the method comprising:
   (1) an application step of applying the photosensitive resin composition according to claim 1 onto a substrate;
   (2) a solvent removal step of removing the solvent from the photosensitive resin composition that has been applied;
   (3) an exposure step of exposing to actinic radiation the photosensitive resin composition that has been applied;
   (4) a development step of developing the exposed photosensitive resin composition by means of an aqueous developer; and
   (5) a post-baking step of thermally curing the developed photosensitive resin composition.

18. A cured film formed by applying at least one of light and heat to the photosensitive resin composition according to any one of claim 1.

19. The cured film according to claim 18, wherein it is an interlayer insulating film.

20. An organic EL display device comprising the cured film according to claim 18.

21. A liquid crystal display device comprising the cured film according to claim 18.

* * * * *